United States Patent
Foster et al.

(10) Patent No.: US 7,387,780 B2
(45) Date of Patent: Jun. 17, 2008

(54) SOLUBLE INTERLEUKIN-20 RECEPTOR

(75) Inventors: Donald C. Foster, Lake Forest Park, WA (US); Wenfeng Xu, Seattle, WA (US); Karen L. Madden, Bellevue, WA (US); James D. Kelly, Mercer Island, WA (US); Cindy A. Sprecher, Patagonia, AZ (US); Cameron S. Brandt, Seattle, WA (US); Mark W. Rixon, Issaquah, WA (US); Scott R. Presnell, Tacoma, WA (US); Brian A. Fox, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 11/458,360

(22) Filed: Jul. 18, 2006

(65) Prior Publication Data
US 2006/0263850 A1    Nov. 23, 2006

Related U.S. Application Data

(63) Continuation of application No. 09/745,792, filed on Dec. 22, 2000, now Pat. No. 7,122,632.

(60) Provisional application No. 60/171,966, filed on Dec. 23, 1999, provisional application No. 60/213,416, filed on Jun. 22, 2000.

(51) Int. Cl.
*C07K 14/705* (2006.01)
*C12P 21/02* (2006.01)

(52) U.S. Cl. .................. 424/185.1; 530/350; 435/69.1; 536/23.5

(58) Field of Classification Search ...................... None
See application file for complete search history.

(56) References Cited

U.S. PATENT DOCUMENTS 5,945,511 A    8/1999    Lok et al.
6,020,163 A    2/2000    Conklin

FOREIGN PATENT DOCUMENTS

| WO | 99/03982 | 1/1999 |
|---|---|---|
| WO | WO99/07740 | 2/1999 |
| WO | 99/37772 | 7/1999 |
| WO | 99/46281 | 9/1999 |
| WO | WO99/46379 | 9/1999 |
| WO | 99/61630 | 12/1999 |
| WO | WO00/39161 | 7/2000 |
| WO | 00/73454 | 12/2000 |
| WO | 01/46232 | 6/2001 |
| WO | 01/46261 | 6/2001 |

OTHER PUBLICATIONS

Blumberg, H. et al., Cell 104:9-19, 2001.
Rich, B.E. and Kupper, T.S., Current Biol. 11: R531-R534, 2001.
Rose-John, S., Acta biochemical Polonica 50(3): 603-611, 2003.
Robinson et al., PNAS 95: 5929-5934, May 1998.
Parrish-Novak J et al: "Interleukins 19, 20, and 24 Signal Through Two Distinct Receptor Complexes", Journal of Biological Chemistry, American Society of Biolochemical Biologists, Birmingham, US, vol. 277, No. 49, pp. 47517-47523, XP001167074 ISSN: 0021-9258, Dec. 6, 2002.

*Primary Examiner*—Manjunath Rao
*Assistant Examiner*—Fozia Hamud
(74) *Attorney, Agent, or Firm*—Aaron A. Schützer; Shelby J. Walker

(57) ABSTRACT

A soluble receptor to IL-20 having two polypeptide subunits, IL-20RA (formerly called ZcytoR7) and IL-20RB (formerly called DIRS1). The two subunits are preferably linked together. In one embodiment one subunit is fused to the constant region of the light chain of an immunoglobulin, and the other subunit is fused to the constant region of the heavy chain of the immunoglobulin. The light chain and the heavy chain are connected via a disulfide bond.

7 Claims, 8 Drawing Sheets

SEQUENCE LISTING

<160> NUMBER OF SEQ ID NOS: 72

<210> SEQ ID NO 1
<211> LENGTH: 176
<212> TYPE: PRT
<213> ORGANISM: Homo sapiens

<400> SEQUENCE: 1

```
Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Asp
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175
```

<210> SEQ ID NO 2
<211> LENGTH: 152
<212> TYPE: PRT
<213> ORGANISM: Homo sapiens

<400> SEQUENCE: 2

```
Leu Lys Thr Leu Asn Leu Gly Ser Cys Val Ile Ala Thr Asn Leu Gln
 1               5                  10                  15

Glu Ile Arg Asn Gly Phe Ser Asp Ile Arg Gly Ser Val Gln Ala Lys
             20                  25                  30

Asp Gly Asn Ile Asp Ile Arg Ile Leu Arg Arg Thr Glu Ser Leu Gln
         35                  40                  45

Asp Thr Lys Pro Ala Asn Arg Cys Cys Leu Leu Arg His Leu Leu Arg
 50                  55                  60

Leu Tyr Leu Asp Arg Val Phe Lys Asn Tyr Gln Thr Pro Asp His Tyr
 65                  70                  75                  80

Thr Leu Arg Lys Ile Ser Ser Leu Ala Asn Ser Phe Leu Thr Ile Lys
                 85                  90                  95

Lys Asp Leu Arg Leu Cys His Ala His Met Thr Cys His Cys Gly Glu
            100                 105                 110

Glu Ala Met Lys Lys Tyr Ser Gln Ile Leu Ser His Phe Glu Lys Leu
            115                 120                 125

Glu Pro Gln Ala Ala Val Val Lys Ala Leu Gly Glu Leu Asp Ile Leu
        130                 135                 140

Leu Gln Trp Met Glu Glu Thr Glu
145                 150
```

<210> SEQ ID NO 3
<211> LENGTH: 151
<212> TYPE: PRT
<213> ORGANISM: Homo sapiens

<400> SEQUENCE: 3

```
Met Lys Ala Ser Ser Leu Ala Phe Ser Leu Leu Ser Ala Ala Phe Tyr
 1               5                  10                  15

Leu Leu Trp Thr Pro Ser Thr Gly Leu Lys Thr Leu Asn Leu Gly Ser
             20                  25                  30

Cys Val Ile Ala Thr Asn Leu Gln Glu Ile Arg Asn Gly Phe Ser Asp
         35                  40                  45

Ile Arg Gly Ser Val Gln Ala Lys Asp Gly Asn Ile Asp Ile Arg Ile
 50                  55                  60

Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
                 85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys Leu Glu
            115                 120                 125

Pro Gln Ala Ala Val Val Lys Ala Leu Gly Glu Leu Asp Ile Leu Leu
        130                 135                 140

Gln Trp Met Glu Glu Thr Glu
145                 150
```

<210> SEQ ID NO 4
<211> LENGTH: 127
<212> TYPE: PRT
<213> ORGANISM: Homo sapiens

<400> SEQUENCE: 4

Leu Lys Thr Leu Asn Leu Gly Ser Cys Val Ile Ala Thr Asn Leu Gln
1               5                   10                  15

Glu Ile Arg Asn Gly Phe Ser Asp Ile Arg Gly Ser Val Gln Ala Lys
            20                  25                  30

Asp Gly Asn Ile Asp Ile Arg Ile Leu Arg Arg Thr Glu Ser Leu Gln
        35                  40                  45

Asp Thr Lys Pro Ala Asn Arg Cys Cys Leu Leu Arg His Leu Leu Arg
50                  55                  60

Leu Tyr Leu Asp Arg Val Phe Lys Asn Tyr Gln Thr Pro Asp His Tyr
65                  70                  75                  80

Thr Leu Arg Lys Ile Ser Ser Leu Ala Asn Ser Phe Leu Thr Ile Lys
                85                  90                  95

Lys Asp Leu Arg Leu Cys Leu Glu Pro Gln Ala Ala Val Val Lys Ala
            100                 105                 110

Leu Gly Glu Leu Asp Ile Leu Leu Gln Trp Met Glu Glu Thr Glu
        115                 120                 125

<210> SEQ ID NO 5
<211> LENGTH: 176
<212> TYPE: PRT
<213> ORGANISM: Mus musculis

<400> SEQUENCE: 5

Met Lys Gly Phe Gly Leu Ala Phe Gly Leu Phe Ser Ala Val Gly Phe
1               5                   10                  15

Leu Leu Trp Thr Pro Leu Thr Gly Leu Lys Thr Leu His Leu Gly Ser
            20                  25                  30

Cys Val Ile Thr Ala Asn Leu Gln Ala Ile Gln Lys Glu Phe Ser Glu
        35                  40                  45

Ile Arg Asp Ser Val Gln Ala Glu Asp Thr Asn Ile Asp Ile Arg Ile
    50                  55                  60

Leu Arg Thr Thr Glu Ser Leu Lys Asp Ile Lys Ser Leu Asp Arg Cys
65                  70                  75                  80

Cys Phe Leu Arg His Leu Val Arg Phe Tyr Leu Asp Arg Val Phe Lys
                85                  90                  95

Val Tyr Gln Thr Pro Asp His His Thr Leu Arg Lys Ile Ser Ser Leu
            100                 105                 110

Ala Asn Ser Phe Leu Ile Ile Lys Lys Asp Leu Ser Val Cys His Ser
        115                 120                 125

His Met Ala Cys His Cys Gly Glu Glu Ala Met Glu Lys Tyr Asn Gln
    130                 135                 140

Ile Leu Ser His Phe Ile Glu Leu Glu Leu Gln Ala Ala Val Val Lys
145                 150                 155                 160

Ala Leu Gly Glu Leu Gly Ile Leu Leu Arg Trp Met Glu Glu Met Leu
                165                 170                 175

<210> SEQ ID NO 6
<211> LENGTH: 152
<212> TYPE: PRT
<213> ORGANISM: Mus musculis

<400> SEQUENCE: 6

Leu Lys Thr Leu His Leu Gly Ser Cys Val Ile Thr Ala Asn Leu Gln
1               5                   10                  15

Ala Ile Gln Lys Glu Phe Ser Glu Ile Arg Asp Ser Val Gln Ala Glu
            20                  25                  30

```
Asp Thr Asn Ile Asp Ile Arg Ile Leu Arg Thr Thr Glu Ser Leu Lys
            35                  40                  45

Asp Ile Lys Ser Leu Asp Arg Cys Cys Phe Leu Arg His Leu Val Arg
     50                  55                  60

Phe Tyr Leu Asp Arg Val Phe Lys Val Tyr Gln Thr Pro Asp His His
 65                  70                  75                  80

Thr Leu Arg Lys Ile Ser Ser Leu Ala Asn Ser Phe Leu Ile Ile Lys
                 85                  90                  95

Lys Asp Leu Ser Val Cys His Ser His Met Ala Cys His Cys Gly Glu
            100                 105                 110

Glu Ala Met Glu Lys Tyr Asn Gln Ile Leu Ser His Phe Ile Glu Leu
        115                 120                 125

Glu Leu Gln Ala Ala Val Val Lys Ala Leu Gly Glu Leu Gly Ile Leu
    130                 135                 140

Leu Arg Trp Met Glu Met Leu
145                 150

<210> SEQ ID NO 7
<211> LENGTH: 144
<212> TYPE: PRT
<213> ORGANISM: Mus musculis

<400> SEQUENCE: 7

Cys Val Ile Thr Ala Asn Leu Gln Ala Ile Gln Lys Glu Phe Ser Glu
  1               5                  10                  15

Ile Arg Asp Ser Val Gln Ala Glu Asp Thr Asn Ile Asp Ile Arg Ile
             20                  25                  30

Leu Arg Thr Thr Glu Ser Leu Lys Asp Ile Lys Ser Leu Asp Arg Cys
         35                  40                  45

Cys Phe Leu Arg His Leu Val Arg Phe Tyr Leu Asp Arg Val Phe Lys
     50                  55                  60

Val Tyr Gln Thr Pro Asp His His Thr Leu Arg Lys Ile Ser Ser Leu
 65                  70                  75                  80

Ala Asn Ser Phe Leu Ile Ile Lys Lys Asp Leu Ser Val Cys His Ser
                 85                  90                  95

His Met Ala Cys His Cys Gly Glu Glu Ala Met Glu Lys Tyr Asn Gln
            100                 105                 110

Ile Leu Ser His Phe Ile Glu Leu Glu Leu Gln Ala Ala Val Val Lys
        115                 120                 125

Ala Leu Gly Glu Leu Gly Ile Leu Leu Arg Trp Met Glu Met Leu
    130                 135                 140

<210> SEQ ID NO 8
<211> LENGTH: 154
<212> TYPE: PRT
<213> ORGANISM: Mus musculis

<400> SEQUENCE: 8

Met Lys Gly Phe Gly Leu Ala Phe Gly Leu Phe Ser Ala Val Gly Phe
  1               5                  10                  15

Leu Leu Trp Thr Pro Leu Thr Gly Leu Lys Thr Leu His Leu Gly Ser
             20                  25                  30

Cys Val Ile Thr Ala Asn Leu Gln Ala Ile Gln Lys Glu Phe Ser Glu
         35                  40                  45

Ile Arg Asp Ser Val Ser Leu Asp Arg Cys Cys Phe Leu Arg His Leu
     50                  55                  60
```

```
Val Arg Phe Tyr Leu Asp Arg Val Phe Lys Val Tyr Gln Thr Pro Asp
 65                  70                  75                  80

His His Thr Leu Arg Lys Ile Ser Ser Leu Ala Asn Ser Phe Leu Ile
                 85                  90                  95

Ile Lys Lys Asp Leu Ser Val Cys His Ser His Met Ala Cys His Cys
            100                 105                 110

Gly Glu Glu Ala Met Glu Lys Tyr Asn Gln Ile Leu Ser His Phe Ile
        115                 120                 125

Glu Leu Glu Leu Gln Ala Ala Val Val Lys Ala Leu Gly Glu Leu Gly
    130                 135                 140

Ile Leu Leu Arg Trp Met Glu Glu Met Leu
145                 150
```

<210> SEQ ID NO 9
<211> LENGTH: 130
<212> TYPE: PRT
<213> ORGANISM: Homo sapiens

<400> SEQUENCE: 9

```
Leu Lys Thr Leu His Leu Gly Ser Cys Val Ile Thr Ala Asn Leu Gln
  1               5                  10                  15

Ala Ile Gln Lys Glu Phe Ser Glu Ile Arg Asp Ser Val Ser Leu Asp
             20                  25                  30

Arg Cys Cys Phe Leu Arg His Leu Val Arg Phe Tyr Leu Asp Arg Val
         35                  40                  45

Phe Lys Val Tyr Gln Thr Pro Asp His His Thr Leu Arg Lys Ile Ser
     50                  55                  60

Ser Leu Ala Asn Ser Phe Leu Ile Ile Lys Lys Asp Leu Ser Val Cys
 65                  70                  75                  80

His Ser His Met Ala Cys His Cys Gly Glu Glu Ala Met Glu Lys Tyr
                 85                  90                  95

Asn Gln Ile Leu Ser His Phe Ile Glu Leu Glu Leu Gln Ala Ala Val
            100                 105                 110

Val Lys Ala Leu Gly Glu Leu Gly Ile Leu Leu Arg Trp Met Glu Glu
        115                 120                 125

Met Leu
    130
```

<210> SEQ ID NO 10
<211> LENGTH: 3516
<212> TYPE: DNA
<213> ORGANISM: Homo sapiens
<220> FEATURE:
<221> NAME/KEY: CDS
<222> LOCATION: (237)...(1895)

<400> SEQUENCE: 10

```
tccagctggg tagccggggg agcgcgcgtg ggggctccgc gagtcgctcg cccttggttt      60
ctggggaagc ctgggggacg cggctgtggc ggaggcgccc tgggactcag gtcgcctgga    120
gcgtggcacg cagagcccca ggcgcggagc tgaggccgcg cggccgcgct ggccccagc     180 gggcgtggga ctgagcagtc tgctgccccc cgacatgtga cccagccccg ccgccc atg    239
                                                             Met
                                                               1 cgg gct ccc ggc cgc ccg gcc ctg cgg ccg ctg ccg ctg ccg ccg ctg      287
Arg Ala Pro Gly Arg Pro Ala Leu Arg Pro Leu Pro Leu Pro Pro Leu
             5                  10                  15 ctg ctg ttg ctc ctg gcg gcg cct tgg gga cgg gca gtt ccc tgt gtc      335
```

```
                                                        -continued

Leu Leu Leu Leu Leu Ala Ala Pro Trp Gly Arg Ala Val Pro Cys Val
         20                  25                  30 tct ggt ggt ttg cct aaa cct gca aac atc acc ttc tta tcc atc aac       383
Ser Gly Gly Leu Pro Lys Pro Ala Asn Ile Thr Phe Leu Ser Ile Asn
         35                  40                  45 atg aag aat gtc cta caa tgg act cca cca gag ggt ctt caa gga gtt       431
Met Lys Asn Val Leu Gln Trp Thr Pro Pro Glu Gly Leu Gln Gly Val
 50              55                  60                  65 aaa gtt act tac act gtg cag tat ttc ata tat ggg caa aag aaa tgg       479
Lys Val Thr Tyr Thr Val Gln Tyr Phe Ile Tyr Gly Gln Lys Lys Trp
                     70                  75                  80 ctg aat aaa tca gaa tgc aga aat atc aat aga acc tac tgt gat ctt       527
Leu Asn Lys Ser Glu Cys Arg Asn Ile Asn Arg Thr Tyr Cys Asp Leu
             85                  90                  95 tct gct gaa act tct gac tac gaa cac cag tat tat gcc aaa gtt aag       575
Ser Ala Glu Thr Ser Asp Tyr Glu His Gln Tyr Tyr Ala Lys Val Lys
        100                 105                 110 gcc att tgg gga aca aag tgt tcc aaa tgg gct gaa agt gga cgg ttc       623
Ala Ile Trp Gly Thr Lys Cys Ser Lys Trp Ala Glu Ser Gly Arg Phe
    115                 120                 125 tat cct ttt tta gaa aca caa att ggc cca cca gag gtg gca ctg act       671
Tyr Pro Phe Leu Glu Thr Gln Ile Gly Pro Pro Glu Val Ala Leu Thr
130                 135                 140                 145 aca gat gag aag tcc att tct gtt gtc ctg aca gct cca gag aag tgg       719
Thr Asp Glu Lys Ser Ile Ser Val Val Leu Thr Ala Pro Glu Lys Trp
                150                 155                 160 aag aga aat cca gaa gac ctt cct gtt tcc atg caa caa ata tac tcc       767
Lys Arg Asn Pro Glu Asp Leu Pro Val Ser Met Gln Gln Ile Tyr Ser
            165                 170                 175 aat ctg aag tat aac gtg tct gtg ttg aat act aaa tca aac aga acg       815
Asn Leu Lys Tyr Asn Val Ser Val Leu Asn Thr Lys Ser Asn Arg Thr
        180                 185                 190 tgg tcc cag tgt gtg acc aac cac acg ctg gtg ctc acc tgg ctg gag       863
Trp Ser Gln Cys Val Thr Asn His Thr Leu Val Leu Thr Trp Leu Glu
    195                 200                 205 ccg aac act ctt tac tgc gta cac gtg gag tcc ttc gtc cca ggg ccc       911
Pro Asn Thr Leu Tyr Cys Val His Val Glu Ser Phe Val Pro Gly Pro
210                 215                 220                 225 cct cgc cgt gct cag cct tct gag aag cag tgt gcc agg act ttg aaa       959
Pro Arg Arg Ala Gln Pro Ser Glu Lys Gln Cys Ala Arg Thr Leu Lys
                230                 235                 240 gat caa tca tca gag ttc aag gct aaa atc atc ttc tgg tat gtt ttg      1007
Asp Gln Ser Ser Glu Phe Lys Ala Lys Ile Ile Phe Trp Tyr Val Leu
            245                 250                 255 ccc ata tct att acc gtg ttt ctt ttt tct gtg atg ggc tat tcc atc      1055
Pro Ile Ser Ile Thr Val Phe Leu Phe Ser Val Met Gly Tyr Ser Ile
        260                 265                 270 tac cga tat atc cac gtt ggc aaa gag aaa cac cca gca aat ttg att      1103
Tyr Arg Tyr Ile His Val Gly Lys Glu Lys His Pro Ala Asn Leu Ile
    275                 280                 285 ttg att tat gga aat gaa ttt gac aaa aga ttc ttt gtg cct gct gaa      1151
Leu Ile Tyr Gly Asn Glu Phe Asp Lys Arg Phe Phe Val Pro Ala Glu
290                 295                 300                 305 aaa atc gtg att aac ttt atc acc ctc aat atc tcg gat gat tct aaa      1199
Lys Ile Val Ile Asn Phe Ile Thr Leu Asn Ile Ser Asp Asp Ser Lys
                310                 315                 320 att tct cat cag gat atg agt tta ctg gga aaa agc agt gat gta tcc      1247
Ile Ser His Gln Asp Met Ser Leu Leu Gly Lys Ser Ser Asp Val Ser
            325                 330                 335
```

```
agc ctt aat gat cct cag ccc agc ggg aac ctg agg ccc cct cag gag    1295
Ser Leu Asn Asp Pro Gln Pro Ser Gly Asn Leu Arg Pro Pro Gln Glu
        340                 345                 350 gaa gag gag gtg aaa cat tta ggg tat gct tcg cat ttg atg gaa att    1343
Glu Glu Glu Val Lys His Leu Gly Tyr Ala Ser His Leu Met Glu Ile
    355                 360                 365 ttt tgt gac tct gaa gaa aac acg gaa ggt act tct ttc acc cag caa    1391
Phe Cys Asp Ser Glu Glu Asn Thr Glu Gly Thr Ser Phe Thr Gln Gln
370                 375                 380                 385 gag tcc ctc agc aga aca ata ccc ccg gat aaa aca gtc att gaa tat    1439
Glu Ser Leu Ser Arg Thr Ile Pro Pro Asp Lys Thr Val Ile Glu Tyr
                390                 395                 400 gaa tat gat gtc aga acc act gac att tgt gcg ggg cct gaa gag cag    1487
Glu Tyr Asp Val Arg Thr Thr Asp Ile Cys Ala Gly Pro Glu Glu Gln
            405                 410                 415 gag ctc agt ttg cag gag gag gtg tcc aca caa gga aca tta ttg gag    1535
Glu Leu Ser Leu Gln Glu Glu Val Ser Thr Gln Gly Thr Leu Leu Glu
        420                 425                 430 tcg cag gca gcg ttg gca gtc ttg ggc ccg caa acg tta cag tac tca    1583
Ser Gln Ala Ala Leu Ala Val Leu Gly Pro Gln Thr Leu Gln Tyr Ser
    435                 440                 445 tac acc cct cag ctc caa gac tta gac ccc ctg gcg cag gag cac aca    1631
Tyr Thr Pro Gln Leu Gln Asp Leu Asp Pro Leu Ala Gln Glu His Thr
450                 455                 460                 465 gac tcg gag gag ggg ccg gag gaa gag cca tcg acg acc ctg gtc gac    1679
Asp Ser Glu Glu Gly Pro Glu Glu Glu Pro Ser Thr Thr Leu Val Asp
                470                 475                 480 tgg gat ccc caa act ggc agg ctg tgt att cct tcg ctg tcc agc ttc    1727
Trp Asp Pro Gln Thr Gly Arg Leu Cys Ile Pro Ser Leu Ser Ser Phe
            485                 490                 495 gac cag gat tca gag ggc tgc gag cct tct gag ggg gat ggg ctc gga    1775
Asp Gln Asp Ser Glu Gly Cys Glu Pro Ser Glu Gly Asp Gly Leu Gly
        500                 505                 510 gag gag ggt ctt cta tct aga ctc tat gag gag ccg gct cca gac agg    1823
Glu Glu Gly Leu Leu Ser Arg Leu Tyr Glu Glu Pro Ala Pro Asp Arg
    515                 520                 525 cca cca gga gaa aat gaa acc tat ctc atg caa ttc atg gag gaa tgg    1871
Pro Pro Gly Glu Asn Glu Thr Tyr Leu Met Gln Phe Met Glu Glu Trp
530                 535                 540                 545 ggg tta tat gtg cag atg gaa aac tgatgccaac acttcctttt gccttttgtt    1925
Gly Leu Tyr Val Gln Met Glu Asn
                550 tcctgtgcaa acaagtgagt caccccttg atcccagcca taaagtacct gggatgaaag    1985 aagttttttc cagtttgtca gtgtctgtga gaattactta tttcttttct ctattctcat    2045 agcacgtgtg tgattggttc atgcatgtag gtctcttaac aatgatggtg ggcctctgga    2105 gtccaggggc tggccggttg ttctatgcag agaaagcagt caataaatgt ttgccagact    2165 gggtgcagaa tttattcagg tgggtgtact ctggcctctt ggttcattat tttcaaacaa    2225 gcacacttgt acaattattt tctgggtact tcccatatgc acatagcact gtaaaaaata    2285 tttcccaaag atcactcatt ttataaatac cacttttttca gaattgggtt tattgcgagc    2345 aggaggagat acttaaaaca tgcacatata ccaggttggt ggtaagttgg tcacatgtga    2405 aaacctcaac tatttaatca tcatgattca tattttgagt gaatacatca ggcacagacc    2465 ttcatgatat cacacactct tggctacttt aagaggccat ctttaatact ttatgagtag    2525 ttctggagtg taaacataaa cgagtattct tttgtagtca gaaagtgtc ctctcaataa    2585 tttagtaggg gctattgtc tctcaaaact aacctaaaag aaaatgacac atttttataat    2645
```

-continued

```
agaatattac atttatttct ggaagtgtgt tttcaaaaag atatttacat agtctgtaaa    2705
ctagaaagtg ttaggtaaag ctctaggtta ctgtgttact attataatat taaacattcg    2765
aataggcagt cgttcaaaga ctctttggaa tatctatgaa tgaatatcct ctattcttat    2825
aatattaaaa cccataagta aatataggac atacaagaga aatgagttaa atgactatgt    2885
aagggagagt ttattaaaat ttgatgaaat ttactgtagg aactaaacta tgccataaaa    2945
caatagcttt ctagttcatt tccagtaact gttcccatct cctttaccac ttgttaagaa    3005
aattaaattc ttcagtcacg ctgctttaaa atgggacaaa atctattaag ttgaaccata    3065
tataattgtg gatatttggc tgttttttaat ctgacaagca gtaacttcat atggtttgcc    3125
ttaatatata tttgttttag tcatgaactc ataatccatt gatgctcttt catgagaaga    3185
gatatgaccc atatttcctt attgatatta ttggtacagg cagacaaccc tggtaggaga    3245
gatggattct ggggtcatga cctttcgtga ttatccgcaa atgcaaacag tttcagatct    3305
aatggtttaa tttagggagt aattatatta atcagagtgt tctgttattc tcaatcttta    3365
tagaaacgat tctgctggtt ttgaagaaca gatgtattac actaactgta aaagtagttc    3425
aagagtgaga aagaataaat tgttattaag agcaaaagaa aaataaagtg attgatgata    3485
aaaaaaaaaa aaaaaaagcg gccgcctcga g                                   3516
```

```
<210> SEQ ID NO 11
<211> LENGTH: 553
<212> TYPE: PRT
<213> ORGANISM: Homo sapiens

<400> SEQUENCE: 11
```

Met Arg Ala Pro Gly Arg Pro Ala Leu Arg Pro Leu Pro Leu Pro Pro
1               5                   10                  15

Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
        35                  40                  45

Asn Met Lys Asn Val Leu Gln Trp Thr Pro Pro Glu Gly Leu Gln Gly
    50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
        115                 120                 125

Phe Tyr Pro Phe Leu Glu Thr Gln Ile Gly Pro Pro Glu Val Ala Leu
    130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly

```
             210                 215                 220
Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
                260                 265                 270

Ile Tyr Arg Tyr Ile His Val Gly Lys Glu Lys His Pro Ala Asn Leu
                275                 280                 285

Ile Leu Ile Tyr Gly Asn Glu Phe Asp Lys Arg Phe Phe Val Pro Ala
290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
                340                 345                 350

Glu Glu Glu Glu Val Lys His Leu Gly Tyr Ala Ser His Leu Met Glu
                355                 360                 365

Ile Phe Cys Asp Ser Glu Glu Asn Thr Glu Gly Thr Ser Phe Thr Gln
370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
                420                 425                 430

Glu Ser Gln Ala Ala Leu Ala Val Leu Gly Pro Gln Thr Leu Gln Tyr
                435                 440                 445

Ser Tyr Thr Pro Gln Leu Gln Asp Leu Asp Pro Leu Ala Gln Glu His
                450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
                500                 505                 510

Gly Glu Glu Gly Leu Leu Ser Arg Leu Tyr Glu Pro Ala Pro Asp
                515                 520                 525

Arg Pro Pro Gly Glu Asn Glu Thr Tyr Leu Met Gln Phe Met Glu Glu
530                 535                 540

Trp Gly Leu Tyr Val Gln Met Glu Asn
545                 550

<210> SEQ ID NO 12
<211> LENGTH: 221
<212> TYPE: PRT
<213> ORGANISM: Homo sapiens

<400> SEQUENCE: 12

Val Pro Cys Val Ser Gly Gly Leu Pro Lys Pro Ala Asn Ile Thr Phe
1               5                   10                  15

Leu Ser Ile Asn Met Lys Asn Val Leu Gln Trp Thr Pro Pro Glu Gly
                20                  25                  30
```

```
Leu Gln Gly Val Lys Val Thr Tyr Thr Val Gln Tyr Phe Ile Tyr Gly
            35                  40                  45

Gln Lys Lys Trp Leu Asn Lys Ser Glu Cys Arg Asn Ile Asn Arg Thr
        50                  55                  60

Tyr Cys Asp Leu Ser Ala Glu Thr Ser Asp Tyr Glu His Gln Tyr Tyr
 65                 70                  75                  80

Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
                100                 105                 110

Val Ala Leu Thr Thr Asp Glu Lys Ser Ile Ser Val Leu Thr Ala
                115                 120                 125

Pro Glu Lys Trp Lys Arg Asn Pro Glu Asp Leu Pro Val Ser Met Gln
        130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
                180                 185                 190

Val Pro Gly Pro Pro Arg Arg Ala Gln Pro Ser Glu Lys Gln Cys Ala
                195                 200                 205

Arg Thr Leu Lys Asp Gln Ser Ser Glu Phe Lys Ala Lys
        210                 215                 220

<210> SEQ ID NO 13
<211> LENGTH: 971
<212> TYPE: DNA
<213> ORGANISM: Homo sapiens
<220> FEATURE:
<221> NAME/KEY: CDS
<222> LOCATION: (18)...(950)

<400> SEQUENCE: 13
gaattcgagt ctaccaa atg cag act ttc aca atg gtt cta gaa gaa atc          50
                   Met Gln Thr Phe Thr Met Val Leu Glu Glu Ile
                    1               5                   10 tgg aca agt ctt ttc atg tgg ttt ttc tac gca ttg att cca tgt ttg         98
Trp Thr Ser Leu Phe Met Trp Phe Phe Tyr Ala Leu Ile Pro Cys Leu
         15                  20                  25 ctc aca gat gaa gtg gcc att ctg cct gcc cct cag aac ctc tct gta        146
Leu Thr Asp Glu Val Ala Ile Leu Pro Ala Pro Gln Asn Leu Ser Val
         30                  35                  40 ctc tca acc aac atg aag cat ctc ttg atg tgg agc cca gtg atc gcg        194
Leu Ser Thr Asn Met Lys His Leu Leu Met Trp Ser Pro Val Ile Ala
     45                  50                  55 cct gga gaa aca gtg tac tat tct gtc gaa tac cag ggg gag tac gag        242
Pro Gly Glu Thr Val Tyr Tyr Ser Val Glu Tyr Gln Gly Glu Tyr Glu
 60                  65                  70                  75 agc ctg tac acg agc cac atc tgg atc ccc agc agc tgg tgc tca ctc        290
Ser Leu Tyr Thr Ser His Ile Trp Ile Pro Ser Ser Trp Cys Ser Leu
                 80                  85                  90 act gaa ggt cct gag tgt gat gtc act gat gac atc acg gcc act gtg        338
Thr Glu Gly Pro Glu Cys Asp Val Thr Asp Asp Ile Thr Ala Thr Val
             95                 100                 105 cca tac aac ctt cgt gtc agg gcc aca ttg ggc tca cag acc tca gcc        386
Pro Tyr Asn Leu Arg Val Arg Ala Thr Leu Gly Ser Gln Thr Ser Ala
        110                 115                 120
```

| | | |
|---|---|---|
| tgg agc atc ctg aag cat ccc ttt aat aga aac tca acc atc ctt acc<br>Trp Ser Ile Leu Lys His Pro Phe Asn Arg Asn Ser Thr Ile Leu Thr<br>    125                      130                      135 | 434 |
| cga cct ggg atg gag atc acc aaa gat ggc ttc cac ctg gtt att gag<br>Arg Pro Gly Met Glu Ile Thr Lys Asp Gly Phe His Leu Val Ile Glu<br>140                    145                    150                    155 | 482 |
| ctg gag gac ctg ggg ccc cag ttt gag ttc ctt gtg gcc tac tgg agg<br>Leu Glu Asp Leu Gly Pro Gln Phe Glu Phe Leu Val Ala Tyr Trp Arg<br>                  160                    165                    170 | 530 |
| agg gag cct ggt gcc gag gaa cat gtc aaa atg gtg agg agt ggg ggt<br>Arg Glu Pro Gly Ala Glu Glu His Val Lys Met Val Arg Ser Gly Gly<br>              175                    180                    185 | 578 |
| att cca gtg cac cta gaa acc atg gag cca ggg gct gca tac tgt gtg<br>Ile Pro Val His Leu Glu Thr Met Glu Pro Gly Ala Ala Tyr Cys Val<br>            190                    195                    200 | 626 |
| aag gcc cag aca ttc gtg aag gcc att ggg agg tac agc gcc ttc agc<br>Lys Ala Gln Thr Phe Val Lys Ala Ile Gly Arg Tyr Ser Ala Phe Ser<br>205                    210                    215 | 674 |
| cag aca gaa tgt gtg gag gtg caa gga gag gcc att ccc ctg gta ctg<br>Gln Thr Glu Cys Val Glu Val Gln Gly Glu Ala Ile Pro Leu Val Leu<br>220                    225                    230                    235 | 722 |
| gcc ctg ttt gcc ttt gtt ggc ttc atg ctg atc ctt gtg gtc gtg cca<br>Ala Leu Phe Ala Phe Val Gly Phe Met Leu Ile Leu Val Val Val Pro<br>                  240                    245                    250 | 770 |
| ctg ttc gtc tgg aaa atg ggc cgg ctg ctc cag tac tcc tgt tgc ccc<br>Leu Phe Val Trp Lys Met Gly Arg Leu Leu Gln Tyr Ser Cys Cys Pro<br>                  255                    260                    265 | 818 |
| gtg gtg gtc ctc cca gac acc ttg aaa ata acc aat tca ccc cag aag<br>Val Val Val Leu Pro Asp Thr Leu Lys Ile Thr Asn Ser Pro Gln Lys<br>                    270                    275                    280 | 866 |
| tta atc agc tgc aga agg gag gag gtg gat gcc tgt gcc acg gct gtg<br>Leu Ile Ser Cys Arg Arg Glu Glu Val Asp Ala Cys Ala Thr Ala Val<br>285                    290                    295 | 914 |
| atg tct cct gag gaa ctc ctc agg gcc tgg atc tca taggtttgcg<br>Met Ser Pro Glu Glu Leu Leu Arg Ala Trp Ile Ser<br>300                    305                    310 | 960 |
| gaaggctcga g | 971 |

<210> SEQ ID NO 14
<211> LENGTH: 311
<212> TYPE: PRT
<213> ORGANISM: Homo sapiens

<400> SEQUENCE: 14

Met Gln Thr Phe Thr Met Val Leu Glu Glu Ile Trp Thr Ser Leu Phe
 1               5                  10                  15

Met Trp Phe Phe Tyr Ala Leu Ile Pro Cys Leu Leu Thr Asp Glu Val
                20                  25                  30

Ala Ile Leu Pro Ala Pro Gln Asn Leu Ser Val Leu Ser Thr Asn Met
            35                  40                  45

Lys His Leu Leu Met Trp Ser Pro Val Ile Ala Pro Gly Glu Thr Val
        50                  55                  60

Tyr Tyr Ser Val Glu Tyr Gln Gly Glu Tyr Glu Ser Leu Tyr Thr Ser
 65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

```
Val Arg Ala Thr Leu Gly Ser Gln Thr Ser Ala Trp Ser Ile Leu Lys
            115                 120                 125

His Pro Phe Asn Arg Asn Ser Thr Ile Leu Thr Arg Pro Gly Met Glu
        130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
210                 215                 220

Glu Val Gln Gly Glu Ala Ile Pro Leu Val Leu Ala Leu Phe Ala Phe
225                 230                 235                 240

Val Gly Phe Met Leu Ile Leu Val Val Pro Leu Phe Val Trp Lys
                245                 250                 255

Met Gly Arg Leu Leu Gln Tyr Ser Cys Cys Pro Val Val Val Leu Pro
            260                 265                 270

Asp Thr Leu Lys Ile Thr Asn Ser Pro Gln Lys Leu Ile Ser Cys Arg
        275                 280                 285

Arg Glu Glu Val Asp Ala Cys Ala Thr Ala Val Met Ser Pro Glu Glu
    290                 295                 300

Leu Leu Arg Ala Trp Ile Ser
305                 310

<210> SEQ ID NO 15
<211> LENGTH: 203
<212> TYPE: PRT
<213> ORGANISM: Homo sapiens

<400> SEQUENCE: 15

Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
        35                  40                  45

Tyr Thr Ser His Ile Trp Ile Pro Ser Ser Trp Cys Ser Leu Thr Glu
    50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
            100                 105                 110

Gly Met Glu Ile Thr Lys Asp Gly Phe His Leu Val Ile Glu Leu Glu
        115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175
```

```
Gln Thr Phe Val Lys Ala Ile Gly Arg Tyr Ser Ala Phe Ser Gln Thr
            180                 185                 190

Glu Cys Val Glu Val Gln Gly Glu Ala Ile Pro
        195                 200

<210> SEQ ID NO 16
<211> LENGTH: 33
<212> TYPE: DNA
<213> ORGANISM: Homo sapiens

<400> SEQUENCE: 16
gcgaattcga gtctaccaaa tgcagacttt cac                                    33

<210> SEQ ID NO 17
<211> LENGTH: 32
<212> TYPE: DNA
<213> ORGANISM: Homo sapiens

<400> SEQUENCE: 17
cgctcgagcc ttccgcaaac ctatgagatc ca                                     32

<210> SEQ ID NO 18
<211> LENGTH: 1382
<212> TYPE: DNA
<213> ORGANISM: Homo sapiens
<220> FEATURE:
<221> NAME/KEY: CDS
<222> LOCATION: (132)...(1034)

<400> SEQUENCE: 18
tcgacccacg cgtccgcgct gcgactcaga cctcagctcc aacatatgca ttctgaagaa       60
agatggctga gatggacaga atgctttatt ttggaaagaa acaatgttct aggtcaaact      120
gagtctacca a atg cag act ttc aca atg gtt cta gaa gaa atc tgg aca       170
              Met Gln Thr Phe Thr Met Val Leu Glu Glu Ile Trp Thr
                1               5                  10 agt ctt ttc atg tgg ttt ttc tac gca ttg att cca tgt ttg ctc aca        218
Ser Leu Phe Met Trp Phe Phe Tyr Ala Leu Ile Pro Cys Leu Leu Thr
 15                  20                  25 gat gaa gtg gcc att ctg cct gcc cct cag aac ctc tct gta ctc tca        266
Asp Glu Val Ala Ile Leu Pro Ala Pro Gln Asn Leu Ser Val Leu Ser
 30                  35                  40                  45 acc aac atg aag cat ctc ttg atg tgg agc cca gtg atc gcg cct gga        314
Thr Asn Met Lys His Leu Leu Met Trp Ser Pro Val Ile Ala Pro Gly
                 50                  55                  60 gaa aca gtg tac tat tct gtc gaa tac cag ggg gag tac gag agc ctg        362
Glu Thr Val Tyr Tyr Ser Val Glu Tyr Gln Gly Glu Tyr Glu Ser Leu
             65                  70                  75 tac acg agc cac atc tgg atc ccc agc agc tgg tgc tca ctc act gaa        410
Tyr Thr Ser His Ile Trp Ile Pro Ser Ser Trp Cys Ser Leu Thr Glu
         80                  85                  90 ggt cct gag tgt gat gtc act gat gac atc acg gcc act gtg cca tac        458
Gly Pro Glu Cys Asp Val Thr Asp Asp Ile Thr Ala Thr Val Pro Tyr
     95                 100                 105 aac ctt cgt gtc agg gcc aca ttg ggc tca cag acc tca gcc tgg agc        506
Asn Leu Arg Val Arg Ala Thr Leu Gly Ser Gln Thr Ser Ala Trp Ser
110                 115                 120                 125 atc ctg aag cat ccc ttt aat aga aac tca acc atc ctt acc cga cct        554
Ile Leu Lys His Pro Phe Asn Arg Asn Ser Thr Ile Leu Thr Arg Pro
                130                 135                 140 ggg atg gag atc ccc aaa cat ggc ttc cac ctg gtt att gag ctg gag        602
```

-continued

```
Gly Met Glu Ile Pro Lys His Gly Phe His Leu Val Ile Glu Leu Glu
            145                 150                 155 gac ctg ggg ccc cag ttt gag ttc ctt gtg gcc tac tgg acg agg gag       650
Asp Leu Gly Pro Gln Phe Glu Phe Leu Val Ala Tyr Trp Thr Arg Glu
        160                 165                 170 cct ggt gcc gag gaa cat gtc aaa atg gtg agg agt ggg ggt att cca       698
Pro Gly Ala Glu Glu His Val Lys Met Val Arg Ser Gly Gly Ile Pro
    175                 180                 185 gtg cac cta gaa acc atg gag cca ggg gct gca tac tgt gtg aag gcc       746
Val His Leu Glu Thr Met Glu Pro Gly Ala Ala Tyr Cys Val Lys Ala
190                 195                 200                 205 cag aca ttc gtg aag gcc att ggg agg tac agc gcc ttc agc cag aca       794
Gln Thr Phe Val Lys Ala Ile Gly Arg Tyr Ser Ala Phe Ser Gln Thr
                210                 215                 220 gaa tgt gtg gag gtg caa gga gag gcc att ccc ctg gta ctg gcc ctg       842
Glu Cys Val Glu Val Gln Gly Glu Ala Ile Pro Leu Val Leu Ala Leu
            225                 230                 235 ttt gcc ttt gtt ggc ttc atg ctg atc ctt gtg gtg cca ctg ttc           890
Phe Ala Phe Val Gly Phe Met Leu Ile Leu Val Val Pro Leu Phe
        240                 245                 250 gtc tgg aaa atg ggc cgg ctg ctc cag tac tcc tgt tgc ccc gtg gtg       938
Val Trp Lys Met Gly Arg Leu Leu Gln Tyr Ser Cys Cys Pro Val Val
    255                 260                 265 gtc ctc cca gac acc ttg aaa ata acc aat tca ccc cag gtt aat cag       986
Val Leu Pro Asp Thr Leu Lys Ile Thr Asn Ser Pro Gln Val Asn Gln
270                 275                 280                 285 ctg cag aag gga gga ggt gga tgc ctg tgc cac ggc tgt gat gtc tcc      1034
Leu Gln Lys Gly Gly Gly Gly Cys Leu Cys His Gly Cys Asp Val Ser
                290                 295                 300 tgaggaactc ctcagggcct ggatctcata tcaggtttgc ggaagggccc aggtgaagcc    1094
gagaacctgg tctgcatgac atggaaacca tgagggggaca gttgtgtttt ctgttttccg   1154
ccacggacaa gggatgagag aagtaggaag agcctgttgt ctacaagtct agaagcaacc    1214
atcagaggca gggtggtttg tctaacagaa caactgactg aggctatggg ggttgtgacc    1274
tctagacttt gggcttccac ttgcttggct gagcaaccct gggaaaagtg acttcatccc    1334
ttcggtccca agttttctca tctgtaatgg gggatcccta caaaactg                 1382
```

<210> SEQ ID NO 19
<211> LENGTH: 301
<212> TYPE: PRT
<213> ORGANISM: Homo sapiens

<400> SEQUENCE: 19

```
Met Gln Thr Phe Thr Met Val Leu Glu Glu Ile Trp Thr Ser Leu Phe
  1               5                  10                  15

Met Trp Phe Phe Tyr Ala Leu Ile Pro Cys Leu Leu Thr Asp Glu Val
                 20                  25                  30

Ala Ile Leu Pro Ala Pro Gln Asn Leu Ser Val Leu Ser Thr Asn Met
             35                  40                  45

Lys His Leu Leu Met Trp Ser Pro Val Ile Ala Pro Gly Glu Thr Val
         50                  55                  60

Tyr Tyr Ser Val Glu Tyr Gln Gly Glu Tyr Glu Ser Leu Tyr Thr Ser
 65                  70                  75                  80

His Ile Trp Ile Pro Ser Ser Trp Cys Ser Leu Thr Glu Gly Pro Glu
                 85                  90                  95

Cys Asp Val Thr Asp Asp Ile Thr Ala Thr Val Pro Tyr Asn Leu Arg
            100                 105                 110
```

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Pro Lys His Gly Phe His Leu Val Ile Glu Leu Glu Asp Leu Gly
145                 150                 155                 160

Pro Gln Phe Glu Phe Leu Val Ala Tyr Trp Thr Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Ile Pro Leu Val Leu Ala Leu Phe Ala Phe
225                 230                 235                 240

Val Gly Phe Met Leu Ile Leu Val Val Val Pro Leu Phe Val Trp Lys
                245                 250                 255

Met Gly Arg Leu Leu Gln Tyr Ser Cys Cys Pro Val Val Leu Pro
            260                 265                 270

Asp Thr Leu Lys Ile Thr Asn Ser Pro Gln Val Asn Gln Leu Gln Lys
        275                 280                 285

Gly Gly Gly Gly Cys Leu Cys His Gly Cys Asp Val Ser
    290                 295                 300

<210> SEQ ID NO 20
<211> LENGTH: 1081
<212> TYPE: DNA
<213> ORGANISM: Homo sapiens
<220> FEATURE:
<221> NAME/KEY: CDS
<222> LOCATION: (9)...(1067)

<400> SEQUENCE: 20

```
ggccggcc atg cag act ttc aca atg gtt cta gaa gaa atc tgg aca agt        50
         Met Gln Thr Phe Thr Met Val Leu Glu Glu Ile Trp Thr Ser
           1               5                  10 ctt ttc atg tgg ttt ttc tac gca ttg att cca tgt ttg ctc aca gat        98
Leu Phe Met Trp Phe Phe Tyr Ala Leu Ile Pro Cys Leu Leu Thr Asp
 15             20                  25                  30 gaa gtg gcc att ctg cct gcc cct cag aac ctc tct gta ctc tca acc       146
Glu Val Ala Ile Leu Pro Ala Pro Gln Asn Leu Ser Val Leu Ser Thr
             35                  40                  45 aac atg aag cat ctc ttg atg tgg agc cca gtg atc gcg cct gga gaa       194
Asn Met Lys His Leu Leu Met Trp Ser Pro Val Ile Ala Pro Gly Glu
         50                  55                  60 aca gtg tac tat tct gtc gaa tac cag ggg gag tac gag agc ctg tac       242
Thr Val Tyr Tyr Ser Val Glu Tyr Gln Gly Glu Tyr Glu Ser Leu Tyr
     65                  70                  75 acg agc cac atc tgg atc ccc agc agc tgg tgc tca ctc act gaa ggt       290
Thr Ser His Ile Trp Ile Pro Ser Ser Trp Cys Ser Leu Thr Glu Gly
 80                  85                  90 cct gag tgt gat gtc act gat gac atc acg gcc act gtg cca tac aac       338
Pro Glu Cys Asp Val Thr Asp Asp Ile Thr Ala Thr Val Pro Tyr Asn
 95                 100                 105                 110 ctt cgt gtc agg gcc aca ttg ggc tca cag acc tca gcc tgg agc atc       386
Leu Arg Val Arg Ala Thr Leu Gly Ser Gln Thr Ser Ala Trp Ser Ile
            115                 120                 125
```

```
ctg aag cat ccc ttt aat aga aac tca acc atc ctt acc cga cct ggg      434
Leu Lys His Pro Phe Asn Arg Asn Ser Thr Ile Leu Thr Arg Pro Gly
        130                 135                 140 atg gag atc ccc aaa cat ggc ttc cac ctg gtt att gag ctg gag gac      482
Met Glu Ile Pro Lys His Gly Phe His Leu Val Ile Glu Leu Glu Asp
145                 150                 155 ctg ggg ccc cag ttt gag ttc ctt gtg gcc tac tgg acg agg gag cct      530
Leu Gly Pro Gln Phe Glu Phe Leu Val Ala Tyr Trp Thr Arg Glu Pro
    160                 165                 170 ggt gcc gag gaa cat gtc aaa atg gtg agg agt ggg ggt att cca gtg      578
Gly Ala Glu Glu His Val Lys Met Val Arg Ser Gly Gly Ile Pro Val
175                 180                 185                 190 cac cta gaa acc atg gag cca ggg gct gca tac tgt gtg aag gcc cag      626
His Leu Glu Thr Met Glu Pro Gly Ala Ala Tyr Cys Val Lys Ala Gln
                195                 200                 205 aca ttc gtg aag gcc att ggg agg tac agc gcc ttc agc cag aca gaa      674
Thr Phe Val Lys Ala Ile Gly Arg Tyr Ser Ala Phe Ser Gln Thr Glu
            210                 215                 220 tgt gtg gag gtg caa gga gag gcc gga ggt ggt ggc agt gga ggc ggc      722
Cys Val Glu Val Gln Gly Glu Ala Gly Gly Gly Gly Ser Gly Gly Gly
225                 230                 235 ggt agc gga ggc ggt ggc agt cga act gtg gct gca cca tct gtc ttc      770
Gly Ser Gly Gly Gly Gly Ser Arg Thr Val Ala Ala Pro Ser Val Phe
    240                 245                 250 atc ttc ccg cca tct gat gag cag ttg aaa tct gga act gcc tct gtt      818
Ile Phe Pro Pro Ser Asp Glu Gln Leu Lys Ser Gly Thr Ala Ser Val
255                 260                 265                 270 gtg tgc ctg ctg aat aac ttc tat ccc aga gag gcc aaa gta cag tgg      866
Val Cys Leu Leu Asn Asn Phe Tyr Pro Arg Glu Ala Lys Val Gln Trp
                275                 280                 285 aag gtg gat aac gcc ctc caa tcg ggt aac tcc cag gag agt gtc aca      914
Lys Val Asp Asn Ala Leu Gln Ser Gly Asn Ser Gln Glu Ser Val Thr
            290                 295                 300 gag cag gac agc aag gac agc acc tac agc ctc agc agc acc ctg acg      962
Glu Gln Asp Ser Lys Asp Ser Thr Tyr Ser Leu Ser Ser Thr Leu Thr
305                 310                 315 ctg agc aaa gca gac tac gag aaa cac aaa gtc tac gcc tgc gaa gtc     1010
Leu Ser Lys Ala Asp Tyr Glu Lys His Lys Val Tyr Ala Cys Glu Val
    320                 325                 330 acc cat cag ggc ctg agc tcg ccc gtc aca aag agc ttc aac agg gga     1058
Thr His Gln Gly Leu Ser Ser Pro Val Thr Lys Ser Phe Asn Arg Gly
335                 340                 345                 350 gag tgt taa tctagaggcg cgcc                                         1081
Glu Cys *

<210> SEQ ID NO 21
<211> LENGTH: 352
<212> TYPE: PRT
<213> ORGANISM: Homo sapiens

<400> SEQUENCE: 21

Met Gln Thr Phe Thr Met Val Leu Glu Glu Ile Trp Thr Ser Leu Phe
1               5                   10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60
```

-continued

```
Tyr Tyr Ser Val Glu Tyr Gln Gly Tyr Glu Ser Leu Tyr Thr Ser
 65                  70                  75                  80

His Ile Trp Ile Pro Ser Ser Trp Cys Ser Leu Thr Glu Gly Pro Glu
                 85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Pro Lys His Gly Phe His Leu Val Ile Glu Leu Glu Asp Leu Gly
145                 150                 155                 160

Pro Gln Phe Glu Phe Leu Val Ala Tyr Trp Thr Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Gly Gly Gly Ser Gly Gly Gly Gly Ser
225                 230                 235                 240

Gly Gly Gly Gly Ser Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285

Asp Asn Ala Leu Gln Ser Gly Asn Ser Gln Glu Ser Val Thr Glu Gln
    290                 295                 300

Asp Ser Lys Asp Ser Thr Tyr Ser Leu Ser Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Cys
            340                 345                 350

<210> SEQ ID NO 22
<211> LENGTH: 1801
<212> TYPE: DNA
<213> ORGANISM: Homo sapiens
<220> FEATURE:
<221> NAME/KEY: CDS
<222> LOCATION: (8)...(1789)

<400> SEQUENCE: 22 gtcgacc atg gat gca atg aag aga ggg ctc tgc tgt gtg ctg ctg ctg      49
        Met Asp Ala Met Lys Arg Gly Leu Cys Cys Val Leu Leu Leu
          1               5                  10 tgt ggc gcc gtc ttc gtt tcg ctc agc cag gaa atc cat gcc gag ttg      97
Cys Gly Ala Val Phe Val Ser Leu Ser Gln Glu Ile His Ala Glu Leu
 15                  20                  25                  30 aga cgc ttc cgt aga gtt ccc tgt gtc tct ggt ggt ttg cct aaa cct     145
Arg Arg Phe Arg Arg Val Pro Cys Val Ser Gly Gly Leu Pro Lys Pro
                 35                  40                  45 gca aac atc acc ttc tta tcc atc aac atg aag aat gtc cta caa tgg     193
```

```
Ala Asn Ile Thr Phe Leu Ser Ile Asn Met Lys Asn Val Leu Gln Trp
            50                  55                  60 act cca cca gag ggt ctt caa gga gtt aaa gtt act tac act gtg cag      241
Thr Pro Pro Glu Gly Leu Gln Gly Val Lys Val Thr Tyr Thr Val Gln
            65                  70                  75 tat ttc ata tat ggg caa aag aaa tgg ctg aat aaa tca gaa tgc aga      289
Tyr Phe Ile Tyr Gly Gln Lys Lys Trp Leu Asn Lys Ser Glu Cys Arg
        80                  85                  90 aat atc aat aga acc tac tgt gat ctt tct gct gaa act tct gac tac      337
Asn Ile Asn Arg Thr Tyr Cys Asp Leu Ser Ala Glu Thr Ser Asp Tyr
 95                 100                 105                 110 gaa cac cag tat tat gcc aaa gtt aag gcc att tgg gga aca aag tgt      385
Glu His Gln Tyr Tyr Ala Lys Val Lys Ala Ile Trp Gly Thr Lys Cys
                115                 120                 125 tcc aaa tgg gct gaa agt gga cgg ttc tat cct ttt tta gaa aca caa      433
Ser Lys Trp Ala Glu Ser Gly Arg Phe Tyr Pro Phe Leu Glu Thr Gln
            130                 135                 140 att ggc cca cca gag gtg gca ctg act aca gat gag aag tcc att tct      481
Ile Gly Pro Pro Glu Val Ala Leu Thr Thr Asp Glu Lys Ser Ile Ser
            145                 150                 155 gtt gtc ctg aca gct cca gag aag tgg aag aga aat cca gaa gac ctt      529
Val Val Leu Thr Ala Pro Glu Lys Trp Lys Arg Asn Pro Glu Asp Leu
            160                 165                 170 cct gtt tcc atg caa caa ata tac tcc aat ctg aag tat aac gtg tct      577
Pro Val Ser Met Gln Gln Ile Tyr Ser Asn Leu Lys Tyr Asn Val Ser
175                 180                 185                 190 gtg ttg aat act aaa tca aac aga acg tgg tcc cag tgt gtg acc aac      625
Val Leu Asn Thr Lys Ser Asn Arg Thr Trp Ser Gln Cys Val Thr Asn
                195                 200                 205 cac acg ctg gtg ctc acc tgg ctg gag ccg aac act ctt tac tgc gta      673
His Thr Leu Val Leu Thr Trp Leu Glu Pro Asn Thr Leu Tyr Cys Val
                210                 215                 220 cac gtg gag tcc ttc gtc cca ggg ccc cct cgc cgt gct cag cct tct      721
His Val Glu Ser Phe Val Pro Gly Pro Pro Arg Arg Ala Gln Pro Ser
            225                 230                 235 gag aag cag tgt gcc agg act ttg aaa gat caa ggt gga ggc ggt tca      769
Glu Lys Gln Cys Ala Arg Thr Leu Lys Asp Gln Gly Gly Gly Gly Ser
240                 245                 250 ggc gga ggt ggc tct ggc ggt ggc gga tcg gcc tcc acc aag ggc cca      817
Gly Gly Gly Gly Ser Gly Gly Gly Gly Ser Ala Ser Thr Lys Gly Pro
255                 260                 265                 270 tcg gtc ttc ccc ctg gca ccc tcc tcc aag agc acc tct ggg ggc aca      865
Ser Val Phe Pro Leu Ala Pro Ser Ser Lys Ser Thr Ser Gly Gly Thr
            275                 280                 285 gcg gcc ctg ggc tgc ctg gtc aag gac tac ttc ccc gaa ccg gtg acg      913
Ala Ala Leu Gly Cys Leu Val Lys Asp Tyr Phe Pro Glu Pro Val Thr
            290                 295                 300 gtg tcg tgg aac tca ggc gcc ctg acc agc ggc gtg cac acc ttc ccg      961
Val Ser Trp Asn Ser Gly Ala Leu Thr Ser Gly Val His Thr Phe Pro
            305                 310                 315 gct gtc cta cag tcc tca gga ctc tac tcc ctc agc agc gtg gtg acc     1009
Ala Val Leu Gln Ser Ser Gly Leu Tyr Ser Leu Ser Ser Val Val Thr
            320                 325                 330 gtg ccc tcc agc agc ttg ggc acc cag acc tac atc tgc aac gtg aat     1057
Val Pro Ser Ser Ser Leu Gly Thr Gln Thr Tyr Ile Cys Asn Val Asn
335                 340                 345                 350 cac aag ccc agc aac acc aag gtg gac aag aaa gtt gag ccc aaa tct     1105
His Lys Pro Ser Asn Thr Lys Val Asp Lys Lys Val Glu Pro Lys Ser
                355                 360                 365
```

```
tgt gac aaa act cac aca tgc cca ccg tgc cca gca cct gaa gcc gag      1153
Cys Asp Lys Thr His Thr Cys Pro Pro Cys Pro Ala Pro Glu Ala Glu
            370                 375                 380 ggg gca ccg tca gtc ttc ctc ttc ccc cca aaa ccc aag gac acc ctc      1201
Gly Ala Pro Ser Val Phe Leu Phe Pro Pro Lys Pro Lys Asp Thr Leu
    385                 390                 395 atg atc tcc cgg acc cct gag gtc aca tgc gtg gtg gtg gac gtg agc      1249
Met Ile Ser Arg Thr Pro Glu Val Thr Cys Val Val Val Asp Val Ser
400                 405                 410 cac gaa gac cct gag gtc aag ttc aac tgg tac gtg gac ggc gtg gag      1297
His Glu Asp Pro Glu Val Lys Phe Asn Trp Tyr Val Asp Gly Val Glu
415                 420                 425                 430 gtg cat aat gcc aag aca aag ccg cgg gag gag cag tac aac agc acg      1345
Val His Asn Ala Lys Thr Lys Pro Arg Glu Glu Gln Tyr Asn Ser Thr
                435                 440                 445 tac cgt gtg gtc agc gtc ctc acc gtc ctg cac cag gac tgg ctg aat      1393
Tyr Arg Val Val Ser Val Leu Thr Val Leu His Gln Asp Trp Leu Asn
            450                 455                 460 ggc aag gag tac aag tgc aag gtc tcc aac aaa gcc ctc cca tcc tcc      1441
Gly Lys Glu Tyr Lys Cys Lys Val Ser Asn Lys Ala Leu Pro Ser Ser
465                 470                 475 atc gag aaa acc atc tcc aaa gcc aaa ggg cag ccc cga gaa cca cag      1489
Ile Glu Lys Thr Ile Ser Lys Ala Lys Gly Gln Pro Arg Glu Pro Gln
480                 485                 490 gtg tac acc ctg ccc cca tcc cgg gat gag ctg acc aag aac cag gtc      1537
Val Tyr Thr Leu Pro Pro Ser Arg Asp Glu Leu Thr Lys Asn Gln Val
495                 500                 505                 510 agc ctg acc tgc ctg gtc aaa ggc ttc tat ccc agc gac atc gcc gtg      1585
Ser Leu Thr Cys Leu Val Lys Gly Phe Tyr Pro Ser Asp Ile Ala Val
                515                 520                 525 gag tgg gag agc aat ggg cag ccg gag aac aac tac aag acc acg cct      1633
Glu Trp Glu Ser Asn Gly Gln Pro Glu Asn Asn Tyr Lys Thr Thr Pro
            530                 535                 540 ccc gtg ctg gac tcc gac ggc tcc ttc ttc ctc tac agc aag ctc acc      1681
Pro Val Leu Asp Ser Asp Gly Ser Phe Phe Leu Tyr Ser Lys Leu Thr
545                 550                 555 gtg gac aag agc agg tgg cag cag ggg aac gtc ttc tca tgc tcc gtg      1729
Val Asp Lys Ser Arg Trp Gln Gln Gly Asn Val Phe Ser Cys Ser Val
            560                 565                 570 atg cat gag gct ctg cac aac cac tac acg cag aag agc ctc tcc ctg      1777
Met His Glu Ala Leu His Asn His Tyr Thr Gln Lys Ser Leu Ser Leu
575                 580                 585                 590 tct ccg ggt aaa taatctagat ct                                        1801
Ser Pro Gly Lys <210> SEQ ID NO 23
<211> LENGTH: 594
<212> TYPE: PRT
<213> ORGANISM: Homo sapiens

<400> SEQUENCE: 23

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Val Pro Cys Val Ser Gly Gly Leu Pro Lys Pro Ala Asn
        35                  40                  45

Ile Thr Phe Leu Ser Ile Asn Met Lys Asn Val Leu Gln Trp Thr Pro
    50                  55                  60
```

```
Pro Glu Gly Leu Gln Gly Val Lys Val Thr Tyr Thr Val Gln Tyr Phe
65                  70                  75                  80

Ile Tyr Gly Gln Lys Lys Trp Leu Asn Lys Ser Glu Cys Arg Asn Ile
                85                  90                  95

Asn Arg Thr Tyr Cys Asp Leu Ser Ala Glu Thr Ser Asp Tyr Glu His
            100                 105                 110

Gln Tyr Tyr Ala Lys Val Lys Ala Ile Trp Gly Thr Lys Cys Ser Lys
        115                 120                 125

Trp Ala Glu Ser Gly Arg Phe Tyr Pro Phe Leu Glu Thr Gln Ile Gly
    130                 135                 140

Pro Pro Glu Val Ala Leu Thr Thr Asp Glu Lys Ser Ile Ser Val Val
145                 150                 155                 160

Leu Thr Ala Pro Glu Lys Trp Lys Arg Asn Pro Glu Asp Leu Pro Val
                165                 170                 175

Ser Met Gln Gln Ile Tyr Ser Asn Leu Lys Tyr Asn Val Ser Val Leu
            180                 185                 190

Asn Thr Lys Ser Asn Arg Thr Trp Ser Gln Cys Val Thr Asn His Thr
        195                 200                 205

Leu Val Leu Thr Trp Leu Glu Pro Asn Thr Leu Tyr Cys Val His Val
    210                 215                 220

Glu Ser Phe Val Pro Gly Pro Pro Arg Arg Ala Gln Pro Ser Glu Lys
225                 230                 235                 240

Gln Cys Ala Arg Thr Leu Lys Asp Gln Gly Gly Gly Ser Gly Gly Gly
                245                 250                 255

Gly Gly Ser Gly Gly Gly Ser Ala Ser Thr Lys Gly Pro Ser Val
            260                 265                 270

Phe Pro Leu Ala Pro Ser Ser Lys Ser Thr Ser Gly Gly Thr Ala Ala
        275                 280                 285

Leu Gly Cys Leu Val Lys Asp Tyr Phe Pro Glu Pro Val Thr Val Ser
    290                 295                 300

Trp Asn Ser Gly Ala Leu Thr Ser Gly Val His Thr Phe Pro Ala Val
305                 310                 315                 320

Leu Gln Ser Ser Gly Leu Tyr Ser Leu Ser Ser Val Val Thr Val Pro
                325                 330                 335

Ser Ser Ser Leu Gly Thr Gln Thr Tyr Ile Cys Asn Val Asn His Lys
            340                 345                 350

Pro Ser Asn Thr Lys Val Asp Lys Lys Val Glu Pro Lys Ser Cys Asp
        355                 360                 365

Lys Thr His Thr Cys Pro Pro Cys Pro Ala Pro Glu Ala Glu Gly Ala
    370                 375                 380

Pro Ser Val Phe Leu Phe Pro Pro Lys Pro Lys Asp Thr Leu Met Ile
385                 390                 395                 400

Ser Arg Thr Pro Glu Val Thr Cys Val Val Val Asp Val Ser His Glu
                405                 410                 415

Asp Pro Glu Val Lys Phe Asn Trp Tyr Val Asp Gly Val Glu Val His
            420                 425                 430

Asn Ala Lys Thr Lys Pro Arg Glu Glu Gln Tyr Asn Ser Thr Tyr Arg
        435                 440                 445

Val Val Ser Val Leu Thr Val Leu His Gln Asp Trp Leu Asn Gly Lys
    450                 455                 460

Glu Tyr Lys Cys Lys Val Ser Asn Lys Ala Leu Pro Ser Ser Ile Glu
465                 470                 475                 480

Lys Thr Ile Ser Lys Ala Lys Gly Gln Pro Arg Glu Pro Gln Val Tyr
```

-continued

```
                      485                 490                 495
Thr Leu Pro Pro Ser Arg Asp Glu Leu Thr Lys Asn Gln Val Ser Leu
            500                 505                 510
Thr Cys Leu Val Lys Gly Phe Tyr Pro Ser Asp Ile Ala Val Glu Trp
        515                 520                 525
Glu Ser Asn Gly Gln Pro Glu Asn Asn Tyr Lys Thr Thr Pro Pro Val
    530                 535                 540
Leu Asp Ser Asp Gly Ser Phe Phe Leu Tyr Ser Lys Leu Thr Val Asp
545                 550                 555                 560
Lys Ser Arg Trp Gln Gln Gly Asn Val Phe Ser Cys Ser Val Met His
                565                 570                 575
Glu Ala Leu His Asn His Tyr Thr Gln Lys Ser Leu Ser Leu Ser Pro
            580                 585                 590
Gly Lys

<210> SEQ ID NO 24
<211> LENGTH: 29
<212> TYPE: DNA
<213> ORGANISM: Homo sapiens

<400> SEQUENCE: 24
ggccggccat gcagactttc acaatggtt                                      29

<210> SEQ ID NO 25
<211> LENGTH: 52
<212> TYPE: DNA
<213> ORGANISM: homo sapiens

<400> SEQUENCE: 25
tccgctaccg ccgcctccac tgccaccacc tccggcctct ccttgcacct cc            52

<210> SEQ ID NO 26
<211> LENGTH: 53
<212> TYPE: DNA
<213> ORGANISM: Homo sapiens

<400> SEQUENCE: 26
gtggaggcgg cggtagcgga ggcggtggca gtcgaactgt ggctgcacca tct           53

<210> SEQ ID NO 27
<211> LENGTH: 38
<212> TYPE: DNA
<213> ORGANISM: Homo sapiens

<400> SEQUENCE: 27
ggcgcgcctc tagattaaca ctctcccctg ttgaagct                            38

<210> SEQ ID NO 28
<211> LENGTH: 30
<212> TYPE: DNA
<213> ORGANISM: Homo sapiens

<400> SEQUENCE: 28
gtcgaccatg gatgcaatga agagagggct                                     30

<210> SEQ ID NO 29
<211> LENGTH: 30
<212> TYPE: DNA
<213> ORGANISM: Homo sapiens

<400> SEQUENCE: 29
```
cacagggaac tctacggaag cgtctcaact                                          30

<210> SEQ ID NO 30
<211> LENGTH: 33
<212> TYPE: DNA
<213> ORGANISM: Homo sapiens

<400> SEQUENCE: 30
cttccgtaga gttccctgtg tctctggtgg ttt                                      33

<210> SEQ ID NO 31
<211> LENGTH: 53
<212> TYPE: DNA
<213> ORGANISM: Homo sapiens

<400> SEQUENCE: 31
gccagagcca cctccgcctg aaccgcctcc accttgatct ttcaaagtcc tgg                53

<210> SEQ ID NO 32
<211> LENGTH: 51
<212> TYPE: DNA
<213> ORGANISM: Homo sapiens

<400> SEQUENCE: 32
caggcggagg tggctctggc ggtggcggat cggcctccac caagggccca t                  51

<210> SEQ ID NO 33
<211> LENGTH: 20
<212> TYPE: DNA
<213> ORGANISM: Homo sapiens

<400> SEQUENCE: 33
ctgggcacgg tgggcatgtg                                                     20

<210> SEQ ID NO 34
<211> LENGTH: 20
<212> TYPE: DNA
<213> ORGANISM: Homo sapiens

<400> SEQUENCE: 34
cacatgccca ccgtgcccag                                                     20

<210> SEQ ID NO 35
<211> LENGTH: 31
<212> TYPE: DNA
<213> ORGANISM: Homo sapiens

<400> SEQUENCE: 35
agatctagat tatttacccg gagacaggga g                                        31

<210> SEQ ID NO 36
<211> LENGTH: 1806
<212> TYPE: DNA
<213> ORGANISM: Mus musculus
<220> FEATURE:
<221> NAME/KEY: CDS
<222> LOCATION: (38)...(1675)

<400> SEQUENCE: 36
cgccgcgttc ccgagatgtg acccgaactg acagccc atg cac act ccc ggg acc         55
                                        Met His Thr Pro Gly Thr
                                        1               5 ccg gcg ccg ggc cac ccg gac ccg ccg cca ctg ttg ctg ctc acg ctg          103

```
                Pro Ala Pro Gly His Pro Asp Pro Pro Leu Leu Leu Leu Thr Leu
                        10              15                  20 ctt ctg ctg ctg gcc gct tcg gga cgc gca gtt cct tgt gtc ttc tgt            151
Leu Leu Leu Leu Ala Ala Ser Gly Arg Ala Val Pro Cys Val Phe Cys
            25                  30                  35 ggt ttg cct aaa cct aca aat atc acc ttc tta tcc atc aac atg aag            199
Gly Leu Pro Lys Pro Thr Asn Ile Thr Phe Leu Ser Ile Asn Met Lys
        40                  45                  50 aat gtc ctg cat tgg aat cca cca gag agt cta cac gga gtt gaa gtc            247
Asn Val Leu His Trp Asn Pro Pro Glu Ser Leu His Gly Val Glu Val
55                  60                  65                  70 aca tac act gtg caa tat ttc ata tat ggg cag aag aaa tgg ctg aat            295
Thr Tyr Thr Val Gln Tyr Phe Ile Tyr Gly Gln Lys Lys Trp Leu Asn
                75                  80                  85 gcc tct aaa tgc ggg agt atc aac agg acc tac tgt gac ctt tct gtt            343
Ala Ser Lys Cys Gly Ser Ile Asn Arg Thr Tyr Cys Asp Leu Ser Val
            90                  95                  100 gag acc tca gac tat gaa cac cag ttc tat gcc aaa gtg aag gcc att            391
Glu Thr Ser Asp Tyr Glu His Gln Phe Tyr Ala Lys Val Lys Ala Ile
        105                 110                 115 tgg gaa gcc agg tgc tcc gaa tgg gcc gag acg gaa cgc ttc tat cct            439
Trp Glu Ala Arg Cys Ser Glu Trp Ala Glu Thr Glu Arg Phe Tyr Pro
    120                 125                 130 ttc ttg gaa act caa gtc agc cca cca gag att gcc ctg aca act ggc            487
Phe Leu Glu Thr Gln Val Ser Pro Pro Glu Ile Ala Leu Thr Thr Gly
135                 140                 145                 150 gag aag tcc atc tct att gcc ctg aca gca cca gag aag tgg aaa aga            535
Glu Lys Ser Ile Ser Ile Ala Leu Thr Ala Pro Glu Lys Trp Lys Arg
                155                 160                 165 aat cca caa gac cac act gtt tct atg caa cag ata tac ccc aat ttg            583
Asn Pro Gln Asp His Thr Val Ser Met Gln Gln Ile Tyr Pro Asn Leu
            170                 175                 180 aag tac aat gtg tct gtg tat aac act aag tcg aga aga acg tgg tcc            631
Lys Tyr Asn Val Ser Val Tyr Asn Thr Lys Ser Arg Arg Thr Trp Ser
        185                 190                 195 cag tgt gtc acc aac agc aca ctg gtc ctc agc tgg ctg gag ccc aac            679
Gln Cys Val Thr Asn Ser Thr Leu Val Leu Ser Trp Leu Glu Pro Asn
    200                 205                 210 act ctg tat tgt gtc cac gtg gag tcc ctt gtc cca ggg ccc cct cgc            727
Thr Leu Tyr Cys Val His Val Glu Ser Leu Val Pro Gly Pro Pro Arg
215                 220                 225                 230 ctc ccg atg cct tct cag aag cag tgc atc agt act ttg gaa gtt caa            775
Leu Pro Met Pro Ser Gln Lys Gln Cys Ile Ser Thr Leu Glu Val Gln
                235                 240                 245 aca tca gca tgg aag gct aaa gtc atc ttc tgg tat gtc ttc ctc aca            823
Thr Ser Ala Trp Lys Ala Lys Val Ile Phe Trp Tyr Val Phe Leu Thr
            250                 255                 260 tct gtt atc gtg ttt ctt ttc tcc gca att ggc tac ttg gtt tac cgt            871
Ser Val Ile Val Phe Leu Phe Ser Ala Ile Gly Tyr Leu Val Tyr Arg
        265                 270                 275 tac atc cat gtt ggc aag gaa aaa cac cca gca aat ttg gta ctg att            919
Tyr Ile His Val Gly Lys Glu Lys His Pro Ala Asn Leu Val Leu Ile
    280                 285                 290 tat aga aat gaa att ggc aca aga gtc ttt gaa cct act gaa aca atc            967
Tyr Arg Asn Glu Ile Gly Thr Arg Val Phe Glu Pro Thr Glu Thr Ile
295                 300                 305                 310 aca ctt aat ttt atc acc ttc agt atg ttg gat gat act aaa att tct           1015
Thr Leu Asn Phe Ile Thr Phe Ser Met Leu Asp Asp Thr Lys Ile Ser
                315                 320                 325
```

-continued

```
cca aag gat atg aat tta ctg gac aaa agc agt gat gac atc agt gtt      1063
Pro Lys Asp Met Asn Leu Leu Asp Lys Ser Ser Asp Asp Ile Ser Val
            330                 335                 340 aat gac cct gag cac aat gag gcc tgg gag ccg cac tgg gag gag gtg      1111
Asn Asp Pro Glu His Asn Glu Ala Trp Glu Pro His Trp Glu Glu Val
345                 350                 355 gag ggg caa cat tta gga tgc tct tcg cat ttg atg gac gct gtc tgt      1159
Glu Gly Gln His Leu Gly Cys Ser Ser His Leu Met Asp Ala Val Cys
        360                 365                 370 ggt gct gag caa aga gac gga gac acc tcc cta acc cag cat ggg tgg      1207
Gly Ala Glu Gln Arg Asp Gly Asp Thr Ser Leu Thr Gln His Gly Trp
375                 380                 385                 390 ctt aac agc acc atc ccc aca gga gag aca gac act gag cct caa tac      1255
Leu Asn Ser Thr Ile Pro Thr Gly Glu Thr Asp Thr Glu Pro Gln Tyr
                395                 400                 405 aaa gtc cta agt gac ttc tac ggg gag ggt gaa atc caa ctg tcc tgt      1303
Lys Val Leu Ser Asp Phe Tyr Gly Glu Gly Glu Ile Gln Leu Ser Cys
            410                 415                 420 gag ccg gaa gag gcg gcc aga aca gag aaa ata tct gag cca ctg gtg      1351
Glu Pro Glu Glu Ala Ala Arg Thr Glu Lys Ile Ser Glu Pro Leu Val
425                 430                 435 act tca gca aac ttg gac cca cag ctt gaa gac cta cat cac ctg ggt      1399
Thr Ser Ala Asn Leu Asp Pro Gln Leu Glu Asp Leu His His Leu Gly
        440                 445                 450 cag gag cat act gtc tcc gag gat ggg cca gag gaa gag aca tct ata      1447
Gln Glu His Thr Val Ser Glu Asp Gly Pro Glu Glu Glu Thr Ser Ile
455                 460                 465                 470 aca gta gtg gat tgg gac cct caa act ggc agg ctg tgt atc cct tcc      1495
Thr Val Val Asp Trp Asp Pro Gln Thr Gly Arg Leu Cys Ile Pro Ser
                475                 480                 485 tta cct atc ttt ggc cgt gat cct gag aac tat ggt cat tat gag aga      1543
Leu Pro Ile Phe Gly Arg Asp Pro Glu Asn Tyr Gly His Tyr Glu Arg
            490                 495                 500 gac cag ctc tta gag ggt ggc ctt ttg tct aga ctc tat gag aac cag      1591
Asp Gln Leu Leu Glu Gly Gly Leu Leu Ser Arg Leu Tyr Glu Asn Gln
505                 510                 515 gca cct gac aag cca gag aaa gaa aat gaa aac tgt ctc aca cgg ttt      1639
Ala Pro Asp Lys Pro Glu Lys Glu Asn Glu Asn Cys Leu Thr Arg Phe
        520                 525                 530 atg gag gaa tgg ggg tta cat gta caa atg gaa agc tagtgccagg           1685
Met Glu Glu Trp Gly Leu His Val Gln Met Glu Ser
535                 540                 545 ctttctgttg actgccaaca aatgaaggaa ccatcccagg gggtgaacag tgttcaggtt    1745
atcagtgtca gcaatgagac tgttctctct gttcatgaac tttgtcagcc ctgcctcatc    1805
c                                                                    1806

<210> SEQ ID NO 37
<211> LENGTH: 546
<212> TYPE: PRT
<213> ORGANISM: Mus musculus

<400> SEQUENCE: 37

Met His Thr Pro Gly Thr Pro Ala Pro Gly His Pro Asp Pro Pro
1               5                   10                  15

Leu Leu Leu Leu Thr Leu Leu Leu Leu Ala Ala Ser Gly Arg Ala
                20                  25                  30

Val Pro Cys Val Phe Cys Gly Leu Pro Lys Pro Thr Asn Ile Thr Phe
            35                  40                  45
```

-continued

```
Leu Ser Ile Asn Met Lys Asn Val Leu His Trp Asn Pro Pro Glu Ser
 50                  55                  60

Leu His Gly Val Glu Val Thr Tyr Thr Val Gln Tyr Phe Ile Tyr Gly
 65                  70                  75                  80

Gln Lys Lys Trp Leu Asn Ala Ser Lys Cys Gly Ser Ile Asn Arg Thr
                 85                  90                  95

Tyr Cys Asp Leu Ser Val Glu Thr Ser Asp Tyr Glu His Gln Phe Tyr
                100                 105                 110

Ala Lys Val Lys Ala Ile Trp Glu Ala Arg Cys Ser Glu Trp Ala Glu
                115                 120                 125

Thr Glu Arg Phe Tyr Pro Phe Leu Glu Thr Gln Val Ser Pro Pro Glu
130                 135                 140

Ile Ala Leu Thr Thr Gly Glu Lys Ser Ile Ser Ile Ala Leu Thr Ala
145                 150                 155                 160

Pro Glu Lys Trp Lys Arg Asn Pro Gln Asp His Thr Val Ser Met Gln
                165                 170                 175

Gln Ile Tyr Pro Asn Leu Lys Tyr Asn Val Ser Val Tyr Asn Thr Lys
                180                 185                 190

Ser Arg Arg Thr Trp Ser Gln Cys Val Thr Asn Ser Thr Leu Val Leu
                195                 200                 205

Ser Trp Leu Glu Pro Asn Thr Leu Tyr Cys Val His Val Glu Ser Leu
210                 215                 220

Val Pro Gly Pro Pro Arg Leu Pro Met Pro Ser Gln Lys Gln Cys Ile
225                 230                 235                 240

Ser Thr Leu Glu Val Gln Thr Ser Ala Trp Lys Ala Lys Val Ile Phe
                245                 250                 255

Trp Tyr Val Phe Leu Thr Ser Val Ile Val Phe Leu Phe Ser Ala Ile
                260                 265                 270

Gly Tyr Leu Val Tyr Arg Tyr Ile His Val Gly Lys Glu Lys His Pro
                275                 280                 285

Ala Asn Leu Val Leu Ile Tyr Arg Asn Glu Ile Gly Thr Arg Val Phe
290                 295                 300

Glu Pro Thr Glu Thr Ile Thr Leu Asn Phe Ile Thr Phe Ser Met Leu
305                 310                 315                 320

Asp Asp Thr Lys Ile Ser Pro Lys Asp Met Asn Leu Leu Asp Lys Ser
                325                 330                 335

Ser Asp Asp Ile Ser Val Asn Asp Pro Glu His Asn Glu Ala Trp Glu
                340                 345                 350

Pro His Trp Glu Glu Val Glu Gly Gln His Leu Gly Cys Ser Ser His
                355                 360                 365

Leu Met Asp Ala Val Cys Gly Ala Glu Gln Arg Asp Gly Asp Thr Ser
370                 375                 380

Leu Thr Gln His Gly Trp Leu Asn Ser Thr Ile Pro Thr Gly Glu Thr
385                 390                 395                 400

Asp Thr Glu Pro Gln Tyr Lys Val Leu Ser Asp Phe Tyr Gly Glu Gly
                405                 410                 415

Glu Ile Gln Leu Ser Cys Glu Pro Glu Ala Ala Arg Thr Glu Lys
                420                 425                 430

Ile Ser Glu Pro Leu Val Thr Ser Ala Asn Leu Asp Pro Gln Leu Glu
                435                 440                 445

Asp Leu His His Leu Gly Gln Glu His Thr Val Ser Glu Asp Gly Pro
450                 455                 460

Glu Glu Glu Thr Ser Ile Thr Val Val Asp Trp Asp Pro Gln Thr Gly
```

```
                465                 470                 475                 480
Arg Leu Cys Ile Pro Ser Leu Pro Ile Phe Gly Arg Asp Pro Glu Asn
                    485                 490                 495

Tyr Gly His Tyr Glu Arg Asp Gln Leu Leu Glu Gly Gly Leu Leu Ser
                500                 505                 510

Arg Leu Tyr Glu Asn Gln Ala Pro Asp Lys Pro Glu Lys Glu Asn Glu
                515                 520                 525

Asn Cys Leu Thr Arg Phe Met Glu Glu Trp Gly Leu His Val Gln Met
                530                 535                 540

Glu Ser
545

<210> SEQ ID NO 38
<211> LENGTH: 217
<212> TYPE: PRT
<213> ORGANISM: Mus musculus

<400> SEQUENCE: 38

Val Pro Cys Val Phe Cys Gly Leu Pro Lys Pro Thr Asn Ile Thr Phe
1               5                   10                  15

Leu Ser Ile Asn Met Lys Asn Val Leu His Trp Asn Pro Pro Glu Ser
                20                  25                  30

Leu His Gly Val Glu Val Thr Tyr Thr Val Gln Tyr Phe Ile Tyr Gly
            35                  40                  45

Gln Lys Lys Trp Leu Asn Ala Ser Lys Cys Gly Ser Ile Asn Arg Thr
        50                  55                  60

Tyr Cys Asp Leu Ser Val Glu Thr Ser Asp Tyr Glu His Gln Phe Tyr
65                  70                  75                  80

Ala Lys Val Lys Ala Ile Trp Glu Ala Arg Cys Ser Glu Trp Ala Glu
                85                  90                  95

Thr Glu Arg Phe Tyr Pro Phe Leu Glu Thr Gln Val Ser Pro Pro Glu
            100                 105                 110

Ile Ala Leu Thr Thr Gly Glu Lys Ser Ile Ser Ile Ala Leu Thr Ala
        115                 120                 125

Pro Glu Lys Trp Lys Arg Asn Pro Gln Asp His Thr Val Ser Met Gln
130                 135                 140

Gln Ile Tyr Pro Asn Leu Lys Tyr Asn Val Ser Val Tyr Asn Thr Lys
145                 150                 155                 160

Ser Arg Arg Thr Trp Ser Gln Cys Val Thr Asn Ser Thr Leu Val Leu
                165                 170                 175

Ser Trp Leu Glu Pro Asn Thr Leu Tyr Cys Val His Val Glu Ser Leu
            180                 185                 190

Val Pro Gly Pro Pro Arg Leu Pro Met Pro Ser Gln Lys Gln Cys Ile
        195                 200                 205

Ser Thr Leu Glu Val Gln Thr Ser Ala
    210                 215

<210> SEQ ID NO 39
<211> LENGTH: 514
<212> TYPE: PRT
<213> ORGANISM: Mus musculus

<400> SEQUENCE: 39

Val Pro Cys Val Phe Cys Gly Leu Pro Lys Pro Thr Asn Ile Thr Phe
1               5                   10                  15

Leu Ser Ile Asn Met Lys Asn Val Leu His Trp Asn Pro Pro Glu Ser
```

-continued

```
            20                  25                  30
Leu His Gly Val Glu Val Thr Tyr Thr Val Gln Tyr Phe Ile Tyr Gly
            35                  40                  45
Gln Lys Lys Trp Leu Asn Ala Ser Lys Cys Gly Ser Ile Asn Arg Thr
    50                  55                  60
Tyr Cys Asp Leu Ser Val Glu Thr Ser Asp Tyr Glu His Gln Phe Tyr
65                  70                  75                  80
Ala Lys Val Lys Ala Ile Trp Glu Ala Arg Cys Ser Glu Trp Ala Glu
                85                  90                  95
Thr Glu Arg Phe Tyr Pro Phe Leu Glu Thr Gln Val Ser Pro Pro Glu
            100                 105                 110
Ile Ala Leu Thr Thr Gly Glu Lys Ser Ile Ser Ile Ala Leu Thr Ala
            115                 120                 125
Pro Glu Lys Trp Lys Arg Asn Pro Gln Asp His Thr Val Ser Met Gln
            130                 135                 140
Gln Ile Tyr Pro Asn Leu Lys Tyr Asn Val Ser Val Tyr Asn Thr Lys
145                 150                 155                 160
Ser Arg Arg Thr Trp Ser Gln Cys Val Thr Asn Ser Thr Leu Val Leu
                165                 170                 175
Ser Trp Leu Glu Pro Asn Thr Leu Tyr Cys Val His Val Glu Ser Leu
                180                 185                 190
Val Pro Gly Pro Pro Arg Leu Pro Met Pro Ser Gln Lys Gln Cys Ile
            195                 200                 205
Ser Thr Leu Glu Val Gln Thr Ser Ala Trp Lys Ala Lys Val Ile Phe
            210                 215                 220
Trp Tyr Val Phe Leu Thr Ser Val Ile Val Phe Leu Phe Ser Ala Ile
225                 230                 235                 240
Gly Tyr Leu Val Tyr Arg Tyr Ile His Val Gly Lys Glu Lys His Pro
                245                 250                 255
Ala Asn Leu Val Leu Ile Tyr Arg Asn Glu Ile Gly Thr Arg Val Phe
            260                 265                 270
Glu Pro Thr Glu Thr Ile Thr Leu Asn Phe Ile Thr Phe Ser Met Leu
            275                 280                 285
Asp Asp Thr Lys Ile Ser Pro Lys Asp Met Asn Leu Leu Asp Lys Ser
            290                 295                 300
Ser Asp Asp Ile Ser Val Asn Asp Pro Glu His Asn Glu Ala Trp Glu
305                 310                 315                 320
Pro His Trp Glu Glu Val Glu Gly Gln His Leu Gly Cys Ser Ser His
                325                 330                 335
Leu Met Asp Ala Val Cys Gly Ala Glu Gln Arg Asp Gly Asp Thr Ser
                340                 345                 350
Leu Thr Gln His Gly Trp Leu Asn Ser Thr Ile Pro Thr Gly Glu Thr
            355                 360                 365
Asp Thr Glu Pro Gln Tyr Lys Val Leu Ser Asp Phe Tyr Gly Glu Gly
            370                 375                 380
Glu Ile Gln Leu Ser Cys Glu Pro Glu Glu Ala Ala Arg Thr Glu Lys
385                 390                 395                 400
Ile Ser Glu Pro Leu Val Thr Ser Ala Asn Leu Asp Pro Gln Leu Glu
                405                 410                 415
Asp Leu His His Leu Gly Gln Glu His Thr Val Ser Glu Asp Gly Pro
            420                 425                 430
Glu Glu Glu Thr Ser Ile Thr Val Val Asp Trp Asp Pro Gln Thr Gly
            435                 440                 445
```

Arg Leu Cys Ile Pro Ser Leu Pro Ile Phe Gly Arg Asp Pro Glu Asn
           450                 455                 460

Tyr Gly His Tyr Glu Arg Asp Gln Leu Leu Glu Gly Gly Leu Leu Ser
465                 470                 475                 480

Arg Leu Tyr Glu Asn Gln Ala Pro Asp Lys Pro Glu Lys Glu Asn Glu
                485                 490                 495

Asn Cys Leu Thr Arg Phe Met Glu Glu Trp Gly Leu His Val Gln Met
            500                 505                 510

Glu Ser

<210> SEQ ID NO 40
<211> LENGTH: 18
<212> TYPE: DNA
<213> ORGANISM: Mus musculus

<400> SEQUENCE: 40
cgccgcgttc ccgagatg                                             18

<210> SEQ ID NO 41
<211> LENGTH: 24
<212> TYPE: DNA
<213> ORGANISM: Mus musculus

<400> SEQUENCE: 41
ggatgaggca gggctgacaa agtt                                      24

<210> SEQ ID NO 42
<211> LENGTH: 36
<212> TYPE: DNA
<213> ORGANISM: Homo sapiens

<400> SEQUENCE: 42
acttgtggaa ttcgctagca ccaagggccc atcggt                         36

<210> SEQ ID NO 43
<211> LENGTH: 32
<212> TYPE: DNA
<213> ORGANISM: Homo sapiens

<400> SEQUENCE: 43
gcctagaacg cgttcattta cccggagaca gg                             32

<210> SEQ ID NO 44
<211> LENGTH: 8
<212> TYPE: DNA
<213> ORGANISM: Homo sapiens

<400> SEQUENCE: 44 aattgaga                                                         8

<210> SEQ ID NO 45
<211> LENGTH: 8
<212> TYPE: DNA
<213> ORGANISM: Homo sapiens

<400> SEQUENCE: 45 cgcgtctc                                                         8

<210> SEQ ID NO 46
<211> LENGTH: 37
<212> TYPE: DNA

```
<213> ORGANISM: Homo sapiens

<400> SEQUENCE: 46
gtcacttgaa ttcggtaccg cctctgttgt gtgcctg                              37

<210> SEQ ID NO 47
<211> LENGTH: 32
<212> TYPE: DNA
<213> ORGANISM: Homo sapiens

<400> SEQUENCE: 47
gacctgaacg cgtctaacac tctcccctgt tg                                   32

<210> SEQ ID NO 48
<211> LENGTH: 38
<212> TYPE: DNA
<213> ORGANISM: Homo sapiens

<400> SEQUENCE: 48
tcagtcggaa ttcgcagaag ccatgcgggc tcccggcc                             38

<210> SEQ ID NO 49
<211> LENGTH: 35
<212> TYPE: DNA
<213> ORGANISM: Homo sapiens

<400> SEQUENCE: 49
ctgtgacgct agcctctgat gattgatctt tcaaa                                35

<210> SEQ ID NO 50
<211> LENGTH: 43
<212> TYPE: DNA
<213> ORGANISM: Homo sapiens

<400> SEQUENCE: 50
gatgtctgaa ttcgcagaag ccatgcagac tttcacaatg gtt                       43

<210> SEQ ID NO 51
<211> LENGTH: 86
<212> TYPE: DNA
<213> ORGANISM: Homo sapiens

<400> SEQUENCE: 51
aagacggtac cagatttcaa ctgctcatca gatggcggga agatgaagac agatggtgca     60
gccacagtgg cctctccttg cacctc                                          86

<210> SEQ ID NO 52
<211> LENGTH: 1720
<212> TYPE: DNA
<213> ORGANISM: Homo sapiens
<220> FEATURE:
<221> NAME/KEY: CDS
<222> LOCATION: (1)...(1713)

<400> SEQUENCE: 52
```

| | | | | | | | | | | | | | | | | |
|---|---|---|---|---|---|---|---|---|---|---|---|---|---|---|---|---|
| atg | cgg | gct | ccc | ggc | cgc | ccg | gcc | ctg | cgg | ccg | ctg | ctg | ctg | ttg | ctc | 48 |
| Met | Arg | Ala | Pro | Gly | Arg | Pro | Ala | Leu | Arg | Pro | Leu | Leu | Leu | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctg | gcg | gcg | cct | tgg | gga | cgg | gca | gtt | ccc | tgt | gtc | tct | ggt | ggt | ttg | 96 |
| Leu | Ala | Ala | Pro | Trp | Gly | Arg | Ala | Val | Pro | Cys | Val | Ser | Gly | Gly | Leu | |
| | | 20 | | | | | 25 | | | | | 30 | | | | |

| | | | | | | | | | | | | | | | |
|---|---|---|---|---|---|---|---|---|---|---|---|---|---|---|---|
| cct | aaa | cct | gca | aac | atc | acc | ttc | tta | tcc | atc | aac | atg | aag | aat | gtc | 144 |
| Pro | Lys | Pro | Ala | Asn | Ile | Thr | Phe | Leu | Ser | Ile | Asn | Met | Lys | Asn | Val | |

-continued

|  |  |  |  |  |  |  |  |  |  |  |  |  |  |  |  |
|---|---|---|---|---|---|---|---|---|---|---|---|---|---|---|---|
|  |  |  | 35 |  |  |  | 40 |  |  |  | 45 |  |  |  |  |

```
cta caa tgg act cca cca gag ggt ctt caa gga gtt aaa gtt act tac      192
Leu Gln Trp Thr Pro Pro Glu Gly Leu Gln Gly Val Lys Val Thr Tyr
     50                  55                  60 act gtg cag tat ttc ata tat ggg caa aag aaa tgg ctg aat aaa tca      240
Thr Val Gln Tyr Phe Ile Tyr Gly Gln Lys Lys Trp Leu Asn Lys Ser
 65                  70                  75                  80 gaa tgc aga aat atc aat aga acc tac tgt gat ctt tct gct gaa act      288
Glu Cys Arg Asn Ile Asn Arg Thr Tyr Cys Asp Leu Ser Ala Glu Thr
             85                  90                  95 tct gac tac gaa cac cag tat tat gcc aaa gtt aag gcc att tgg gga      336
Ser Asp Tyr Glu His Gln Tyr Tyr Ala Lys Val Lys Ala Ile Trp Gly
                100                 105                 110 aca aag tgt tcc aaa tgg gct gaa agt gga cgg ttc tat cct ttt tta      384
Thr Lys Cys Ser Lys Trp Ala Glu Ser Gly Arg Phe Tyr Pro Phe Leu
            115                 120                 125 gaa aca caa att ggc cca cca gag gtg gca ctg act aca gat gag aag      432
Glu Thr Gln Ile Gly Pro Pro Glu Val Ala Leu Thr Thr Asp Glu Lys
        130                 135                 140 tcc att tct gtt gtc ctg aca gct cca gag aag tgg aag aga aat cca      480
Ser Ile Ser Val Val Leu Thr Ala Pro Glu Lys Trp Lys Arg Asn Pro
145                 150                 155                 160 gaa gac ctt cct gtt tcc atg caa caa ata tac tcc aat ctg aag tat      528
Glu Asp Leu Pro Val Ser Met Gln Gln Ile Tyr Ser Asn Leu Lys Tyr
                165                 170                 175 aac gtg tct gtg ttg aat act aaa tca aac aga acg tgg tcc cag tgt      576
Asn Val Ser Val Leu Asn Thr Lys Ser Asn Arg Thr Trp Ser Gln Cys
            180                 185                 190 gtg acc aac cac acg ctg gtg ctc acc tgg ctg gag ccg aac act ctt      624
Val Thr Asn His Thr Leu Val Leu Thr Trp Leu Glu Pro Asn Thr Leu
        195                 200                 205 tac tgc gta cac gtg gag tcc ttc gtc cca ggg ccc cct cgc cgt gct      672
Tyr Cys Val His Val Glu Ser Phe Val Pro Gly Pro Pro Arg Arg Ala
210                 215                 220 cag cct tct gag aag cag tgt gcc agg act ttg aaa gat caa tca tca      720
Gln Pro Ser Glu Lys Gln Cys Ala Arg Thr Leu Lys Asp Gln Ser Ser
225                 230                 235                 240 gag gct agc acc aag ggc cca tcg gtc ttc ccc ctg gca ccc tcc tcc      768
Glu Ala Ser Thr Lys Gly Pro Ser Val Phe Pro Leu Ala Pro Ser Ser
                245                 250                 255 aag agc acc tct ggg ggc aca gcg gcc ctg ggc tgc ctg gtc aag gac      816
Lys Ser Thr Ser Gly Gly Thr Ala Ala Leu Gly Cys Leu Val Lys Asp
            260                 265                 270 tac ttc ccc gaa ccg gtg acg gtg tcg tgg aac tca ggc gcc ctg acc      864
Tyr Phe Pro Glu Pro Val Thr Val Ser Trp Asn Ser Gly Ala Leu Thr
        275                 280                 285 agc ggc gtg cac acc ttc ccg gct gtc cta cag tcc tca gga ctc tac      912
Ser Gly Val His Thr Phe Pro Ala Val Leu Gln Ser Ser Gly Leu Tyr
    290                 295                 300 tcc ctc agc agc gtg gtg acc gtg ccc tcc agc agc ttg ggc acc cag      960
Ser Leu Ser Ser Val Val Thr Val Pro Ser Ser Ser Leu Gly Thr Gln
305                 310                 315                 320 acc tac atc tgc aac gtg aat cac aag ccc agc aac acc aag gtg gac     1008
Thr Tyr Ile Cys Asn Val Asn His Lys Pro Ser Asn Thr Lys Val Asp
                325                 330                 335 aag aaa gtt gag ccc aaa tct tgt gac aaa act cac aca tgc cca ccg     1056
Lys Lys Val Glu Pro Lys Ser Cys Asp Lys Thr His Thr Cys Pro Pro
            340                 345                 350 tgc cca gca cct gaa ctc ctg ggg gga ccg tca gtc ttc ctc ttc ccc     1104
```

```
                Cys Pro Ala Pro Glu Leu Leu Gly Gly Pro Ser Val Phe Leu Phe Pro
                            355                 360                 365 cca aaa ccc aag gac acc ctc atg atc tcc cgg acc cct gag gtc aca          1152
Pro Lys Pro Lys Asp Thr Leu Met Ile Ser Arg Thr Pro Glu Val Thr
        370                 375                 380 tgc gtg gtg gtg gac gtg agc cac gaa gac cct gag gtc aag ttc aac          1200
Cys Val Val Val Asp Val Ser His Glu Asp Pro Glu Val Lys Phe Asn
385                 390                 395                 400 tgg tac gtg gac ggc gtg gag gtg cat aat gcc aag aca aag ccg cgg          1248
Trp Tyr Val Asp Gly Val Glu Val His Asn Ala Lys Thr Lys Pro Arg
                405                 410                 415 gag gag cag tac aac agc acg tac cgt gtg gtc agc gtc ctc acc gtc          1296
Glu Glu Gln Tyr Asn Ser Thr Tyr Arg Val Val Ser Val Leu Thr Val
            420                 425                 430 ctg cac cag gac tgg ctg aat ggc aag gag tac aag tgc aag gtc tcc          1344
Leu His Gln Asp Trp Leu Asn Gly Lys Glu Tyr Lys Cys Lys Val Ser
        435                 440                 445 aac aaa gcc ctc cca gcc ccc atc gag aaa acc atc tcc aaa gcc aaa          1392
Asn Lys Ala Leu Pro Ala Pro Ile Glu Lys Thr Ile Ser Lys Ala Lys
    450                 455                 460 ggg cag ccc cga gaa cca cag gtg tac acc ctg ccc cca tcc cgg gat          1440
Gly Gln Pro Arg Glu Pro Gln Val Tyr Thr Leu Pro Pro Ser Arg Asp
465                 470                 475                 480 gag ctg acc aag aac cag gtc agc ctg acc tgc ctg gtc aaa ggc ttc          1488
Glu Leu Thr Lys Asn Gln Val Ser Leu Thr Cys Leu Val Lys Gly Phe
                485                 490                 495 tat ccc agc gac atc gcc gtg gag tgg gag agc aat ggg cag ccg gag          1536
Tyr Pro Ser Asp Ile Ala Val Glu Trp Glu Ser Asn Gly Gln Pro Glu
            500                 505                 510 aac aac tac aag acc acg cct ccc gtg ctg gac tcc gac ggc tcc ttc          1584
Asn Asn Tyr Lys Thr Thr Pro Pro Val Leu Asp Ser Asp Gly Ser Phe
        515                 520                 525 ttc ctc tac agc aag ctc acc gtg gac aag agc agg tgg cag cag ggg          1632
Phe Leu Tyr Ser Lys Leu Thr Val Asp Lys Ser Arg Trp Gln Gln Gly
    530                 535                 540 aac gtc ttc tca tgc tcc gtg atg cat gag gct ctg cac aac cac tac          1680
Asn Val Phe Ser Cys Ser Val Met His Glu Ala Leu His Asn His Tyr
545                 550                 555                 560 acg cag aag agc ctc tcc ctg tct ccg ggt aaa tgacgcg                      1720
Thr Gln Lys Ser Leu Ser Leu Ser Pro Gly Lys
                565                 570

<210> SEQ ID NO 53
<211> LENGTH: 571
<212> TYPE: PRT
<213> ORGANISM: Homo sapiens

<400> SEQUENCE: 53

Met Arg Ala Pro Gly Arg Pro Ala Leu Arg Pro Leu Leu Leu Leu
 1               5                  10                  15

Leu Ala Ala Pro Trp Gly Arg Ala Val Pro Cys Val Ser Gly Gly Leu
                20                  25                  30

Pro Lys Pro Ala Asn Ile Thr Phe Leu Ser Ile Asn Met Lys Asn Val
            35                  40                  45

Leu Gln Trp Thr Pro Pro Glu Gly Leu Gln Gly Val Lys Val Thr Tyr
        50                  55                  60

Thr Val Gln Tyr Phe Ile Tyr Gly Gln Lys Lys Trp Leu Asn Lys Ser
65                  70                  75                  80

Glu Cys Arg Asn Ile Asn Arg Thr Tyr Cys Asp Leu Ser Ala Glu Thr
```

-continued

```
                85                  90                  95
Ser Asp Tyr Glu His Gln Tyr Ala Lys Val Lys Ala Ile Trp Gly
            100                 105                 110

Thr Lys Cys Ser Lys Trp Ala Glu Ser Gly Arg Phe Tyr Pro Phe Leu
            115                 120                 125

Glu Thr Gln Ile Gly Pro Pro Glu Val Ala Leu Thr Thr Asp Glu Lys
            130                 135                 140

Ser Ile Ser Val Val Leu Thr Ala Pro Glu Lys Trp Lys Arg Asn Pro
145                 150                 155                 160

Glu Asp Leu Pro Val Ser Met Gln Gln Ile Tyr Ser Asn Leu Lys Tyr
                165                 170                 175

Asn Val Ser Val Leu Asn Thr Lys Ser Asn Arg Thr Trp Ser Gln Cys
                180                 185                 190

Val Thr Asn His Thr Leu Val Leu Thr Trp Leu Glu Pro Asn Thr Leu
                195                 200                 205

Tyr Cys Val His Val Glu Ser Phe Val Pro Gly Pro Pro Arg Arg Ala
                210                 215                 220

Gln Pro Ser Glu Lys Gln Cys Ala Arg Thr Leu Lys Asp Gln Ser Ser
225                 230                 235                 240

Glu Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
                260                 265                 270

Tyr Phe Pro Glu Pro Val Thr Val Ser Trp Asn Ser Gly Ala Leu Thr
                275                 280                 285

Ser Gly Val His Thr Phe Pro Ala Val Leu Gln Ser Ser Gly Leu Tyr
                290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro
                340                 345                 350

Cys Pro Ala Pro Glu Leu Leu Gly Gly Pro Ser Val Phe Leu Phe Pro
                355                 360                 365

Pro Lys Pro Lys Asp Thr Leu Met Ile Ser Arg Thr Pro Glu Val Thr
                370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
                420                 425                 430

Leu His Gln Asp Trp Leu Asn Gly Lys Glu Tyr Lys Cys Lys Val Ser
                435                 440                 445

Asn Lys Ala Leu Pro Ala Pro Ile Glu Lys Thr Ile Ser Lys Ala Lys
                450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
                500                 505                 510
```

```
Asn Asn Tyr Lys Thr Thr Pro Pro Val Leu Asp Ser Asp Gly Ser Phe
            515                 520                 525

Phe Leu Tyr Ser Lys Leu Thr Val Asp Lys Ser Arg Trp Gln Gln Gly
        530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
            565                 570

<210> SEQ ID NO 54
<211> LENGTH: 547
<212> TYPE: PRT
<213> ORGANISM: Homo sapiens

<400> SEQUENCE: 54

Val Pro Cys Val Ser Gly Gly Leu Pro Lys Pro Ala Asn Ile Thr Phe
1               5                   10                  15

Leu Ser Ile Asn Met Lys Asn Val Leu Gln Trp Thr Pro Pro Glu Gly
            20                  25                  30

Leu Gln Gly Val Lys Val Thr Tyr Thr Val Gln Tyr Phe Ile Tyr Gly
        35                  40                  45

Gln Lys Lys Trp Leu Asn Lys Ser Glu Cys Arg Asn Ile Asn Arg Thr
    50                  55                  60

Tyr Cys Asp Leu Ser Ala Glu Thr Ser Asp Tyr Glu His Gln Tyr Tyr
65                  70                  75                  80

Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Val Leu Thr Ala
        115                 120                 125

Pro Glu Lys Trp Lys Arg Asn Pro Glu Asp Leu Pro Val Ser Met Gln
    130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
        195                 200                 205

Arg Thr Leu Lys Asp Gln Ser Ser Glu Ala Ser Thr Lys Gly Pro Ser
    210                 215                 220

Val Phe Pro Leu Ala Pro Ser Ser Lys Ser Thr Ser Gly Gly Thr Ala
225                 230                 235                 240

Ala Leu Gly Cys Leu Val Lys Asp Tyr Phe Pro Glu Pro Val Thr Val
                245                 250                 255

Ser Trp Asn Ser Gly Ala Leu Thr Ser Gly Val His Thr Phe Pro Ala
            260                 265                 270

Val Leu Gln Ser Ser Gly Leu Tyr Ser Leu Ser Ser Val Val Thr Val
        275                 280                 285

Pro Ser Ser Ser Leu Gly Thr Gln Thr Tyr Ile Cys Asn Val Asn His
    290                 295                 300

Lys Pro Ser Asn Thr Lys Val Asp Lys Lys Val Glu Pro Lys Ser Cys
```

```
                305                 310                 315                 320
Asp Lys Thr His Thr Cys Pro Pro Cys Pro Ala Pro Glu Leu Leu Gly
                325                 330                 335

Gly Pro Ser Val Phe Leu Phe Pro Pro Lys Pro Lys Asp Thr Leu Met
                340                 345                 350

Ile Ser Arg Thr Pro Glu Val Thr Cys Val Val Val Asp Val Ser His
                355                 360                 365

Glu Asp Pro Glu Val Lys Phe Asn Trp Tyr Val Asp Gly Val Glu Val
            370                 375                 380

His Asn Ala Lys Thr Lys Pro Arg Glu Glu Gln Tyr Asn Ser Thr Tyr
385                 390                 395                 400

Arg Val Val Ser Val Leu Thr Val Leu His Gln Asp Trp Leu Asn Gly
                405                 410                 415

Lys Glu Tyr Lys Cys Lys Val Ser Asn Lys Ala Leu Pro Ala Pro Ile
                420                 425                 430

Glu Lys Thr Ile Ser Lys Ala Lys Gly Gln Pro Arg Glu Pro Gln Val
                435                 440                 445

Tyr Thr Leu Pro Pro Ser Arg Asp Glu Leu Thr Lys Asn Gln Val Ser
            450                 455                 460

Leu Thr Cys Leu Val Lys Gly Phe Tyr Pro Ser Asp Ile Ala Val Glu
465                 470                 475                 480

Trp Glu Ser Asn Gly Gln Pro Glu Asn Asn Tyr Lys Thr Thr Pro Pro
                485                 490                 495

Val Leu Asp Ser Asp Gly Ser Phe Phe Leu Tyr Ser Lys Leu Thr Val
                500                 505                 510

Asp Lys Ser Arg Trp Gln Gln Gly Asn Val Phe Ser Cys Ser Val Met
                515                 520                 525

His Glu Ala Leu His Asn His Tyr Thr Gln Lys Ser Leu Ser Leu Ser
            530                 535                 540

Pro Gly Lys
545

<210> SEQ ID NO 55
<211> LENGTH: 217
<212> TYPE: PRT
<213> ORGANISM: Homo sapiens

<400> SEQUENCE: 55

Val Pro Cys Val Ser Gly Gly Leu Pro Lys Pro Ala Asn Ile Thr Phe
1               5                   10                  15

Leu Ser Ile Asn Met Lys Asn Val Leu Gln Trp Thr Pro Pro Glu Gly
                20                  25                  30

Leu Gln Gly Val Lys Val Thr Tyr Thr Val Gln Tyr Phe Ile Tyr Gly
            35                  40                  45

Gln Lys Lys Trp Leu Asn Lys Ser Glu Cys Arg Asn Ile Asn Arg Thr
        50                  55                  60

Tyr Cys Asp Leu Ser Ala Glu Thr Ser Asp Tyr Glu His Gln Tyr Tyr
65                  70                  75                  80

Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
                100                 105                 110

Val Ala Leu Thr Thr Asp Glu Lys Ser Ile Ser Val Val Leu Thr Ala
                115                 120                 125
```

```
Pro Glu Lys Trp Lys Arg Asn Pro Glu Asp Leu Pro Val Ser Met Gln
    130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
        195                 200                 205

Arg Thr Leu Lys Asp Gln Ser Ser Glu
    210                 215

<210> SEQ ID NO 56
<211> LENGTH: 1011
<212> TYPE: DNA
<213> ORGANISM: Homo sapiens
<220> FEATURE:
<221> NAME/KEY: CDS
<222> LOCATION: (1)...(1008)

<400> SEQUENCE: 56 atg cag act ttc aca atg gtt cta gaa gaa atc tgg aca agt ctt ttc      48
Met Gln Thr Phe Thr Met Val Leu Glu Glu Ile Trp Thr Ser Leu Phe
1               5                   10                  15 atg tgg ttt ttc tac gca ttg att cca tgt ttg ctc aca gat gaa gtg      96
Met Trp Phe Phe Tyr Ala Leu Ile Pro Cys Leu Leu Thr Asp Glu Val
                20                  25                  30 gcc att ctg cct gcc cct cag aac ctc tct gta ctc tca acc aac atg     144
Ala Ile Leu Pro Ala Pro Gln Asn Leu Ser Val Leu Ser Thr Asn Met
            35                  40                  45 aag cat ctc ttg atg tgg agc cca gtg atc gcg cct gga gaa aca gtg     192
Lys His Leu Leu Met Trp Ser Pro Val Ile Ala Pro Gly Glu Thr Val
        50                  55                  60 tac tat tct gtc gaa tac cag ggg gag tac gag agc ctg tac acg agc     240
Tyr Tyr Ser Val Glu Tyr Gln Gly Glu Tyr Glu Ser Leu Tyr Thr Ser
65                  70                  75                  80 cac atc tgg atc ccc agc agc tgg tgc tca ctc act gaa ggt cct gag     288
His Ile Trp Ile Pro Ser Ser Trp Cys Ser Leu Thr Glu Gly Pro Glu
                85                  90                  95 tgt gat gtc act gat gac atc acg gcc act gtg cca tac aac ctt cgt     336
Cys Asp Val Thr Asp Asp Ile Thr Ala Thr Val Pro Tyr Asn Leu Arg
            100                 105                 110 gtc agg gcc aca ttg ggc tca cag acc tca gcc tgg agc atc ctg aag     384
Val Arg Ala Thr Leu Gly Ser Gln Thr Ser Ala Trp Ser Ile Leu Lys
        115                 120                 125 cat ccc ttt aat aga aac tca acc atc ctt acc cga cct ggg atg gag     432
His Pro Phe Asn Arg Asn Ser Thr Ile Leu Thr Arg Pro Gly Met Glu
    130                 135                 140 atc acc aaa gat ggc ttc cac ctg gtt att gag ctg gag gac ctg ggg     480
Ile Thr Lys Asp Gly Phe His Leu Val Ile Glu Leu Glu Asp Leu Gly
145                 150                 155                 160 ccc cag ttt gag ttc ctt gtg gcc tac tgg agg agg gag cct ggt gcc     528
Pro Gln Phe Glu Phe Leu Val Ala Tyr Trp Arg Arg Glu Pro Gly Ala
                165                 170                 175 gag gaa cat gtc aaa atg gtg agg agt ggg ggt att cca gtg cac cta     576
Glu Glu His Val Lys Met Val Arg Ser Gly Gly Ile Pro Val His Leu
            180                 185                 190 gaa acc atg gag cca ggg gct gca tac tgt gtg aag gcc cag aca ttc     624
Glu Thr Met Glu Pro Gly Ala Ala Tyr Cys Val Lys Ala Gln Thr Phe
```

```
              195                 200                 205
gtg aag gcc att ggg agg tac agc gcc ttc agc cag aca gaa tgt gtg        672
Val Lys Ala Ile Gly Arg Tyr Ser Ala Phe Ser Gln Thr Glu Cys Val
    210                 215                 220 gag gtg caa gga gag gcc act gtg gct gca cca tct gtc ttc atc ttc        720
Glu Val Gln Gly Glu Ala Thr Val Ala Ala Pro Ser Val Phe Ile Phe
225                 230                 235                 240 ccg cca tct gat gag cag ttg aaa tct ggt acc gcc tct gtt gtg tgc        768
Pro Pro Ser Asp Glu Gln Leu Lys Ser Gly Thr Ala Ser Val Val Cys
                245                 250                 255 ctg ctg aat aac ttc tat ccc aga gag gcc aaa gta cag tgg aag gtg        816
Leu Leu Asn Asn Phe Tyr Pro Arg Glu Ala Lys Val Gln Trp Lys Val
            260                 265                 270 gat aac gcc ctc caa tcg ggt aac tcc cag gag agt gtc aca gag cag        864
Asp Asn Ala Leu Gln Ser Gly Asn Ser Gln Glu Ser Val Thr Glu Gln
        275                 280                 285 gac agc aag gac agc acc tac agc ctc agc agc acc ctg acg ctg agc        912
Asp Ser Lys Asp Ser Thr Tyr Ser Leu Ser Ser Thr Leu Thr Leu Ser
    290                 295                 300 aaa gca gac tac gag aaa cac aaa gtc tac gcc tgc gaa gtc acc cat        960
Lys Ala Asp Tyr Glu Lys His Lys Val Tyr Ala Cys Glu Val Thr His
305                 310                 315                 320 cag ggc ctg agc tcg ccc gtc aca aag agc ttc aac agg gga gag tgt       1008
Gln Gly Leu Ser Ser Pro Val Thr Lys Ser Phe Asn Arg Gly Glu Cys
                325                 330                 335 tag                                                                    1011

<210> SEQ ID NO 57
<211> LENGTH: 336
<212> TYPE: PRT
<213> ORGANISM: Homo sapiens

<400> SEQUENCE: 57

Met Gln Thr Phe Thr Met Val Leu Glu Glu Ile Trp Thr Ser Leu Phe
1               5                   10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190
```

```
Glu Thr Met Glu Pro Gly Ala Ala Tyr Cys Val Lys Ala Gln Thr Phe
            195                 200                 205

Val Lys Ala Ile Gly Arg Tyr Ser Ala Phe Ser Gln Thr Glu Cys Val
    210                 215                 220

Glu Val Gln Gly Glu Ala Thr Val Ala Ala Pro Ser Val Phe Ile Phe
225                 230                 235                 240

Pro Pro Ser Asp Glu Gln Leu Lys Ser Gly Thr Ala Ser Val Val Cys
                245                 250                 255

Leu Leu Asn Asn Phe Tyr Pro Arg Glu Ala Lys Val Gln Trp Lys Val
            260                 265                 270

Asp Asn Ala Leu Gln Ser Gly Asn Ser Gln Glu Ser Val Thr Glu Gln
        275                 280                 285

Asp Ser Lys Asp Ser Thr Tyr Ser Leu Ser Ser Thr Leu Thr Leu Ser
    290                 295                 300

Lys Ala Asp Tyr Glu Lys His Lys Val Tyr Ala Cys Glu Val Thr His
305                 310                 315                 320

Gln Gly Leu Ser Ser Pro Val Thr Lys Ser Phe Asn Arg Gly Glu Cys
                325                 330                 335

<210> SEQ ID NO 58
<211> LENGTH: 307
<212> TYPE: PRT
<213> ORGANISM: Homo sapiens

<400> SEQUENCE: 58

Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
        35                  40                  45

Tyr Thr Ser His Ile Trp Ile Pro Ser Ser Trp Cys Ser Leu Thr Glu
    50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
            100                 105                 110

Gly Met Glu Ile Thr Lys Asp Gly Phe His Leu Val Ile Glu Leu Glu
        115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala Thr Val Ala Ala Pro Ser Val
        195                 200                 205

Phe Ile Phe Pro Pro Ser Asp Glu Gln Leu Lys Ser Gly Thr Ala Ser
    210                 215                 220

Val Val Cys Leu Leu Asn Asn Phe Tyr Pro Arg Glu Ala Lys Val Gln
```

```
                225                 230                 235                 240
Trp Lys Val Asp Asn Ala Leu Gln Ser Gly Asn Ser Gln Glu Ser Val
                    245                 250                 255
Thr Glu Gln Asp Ser Lys Asp Ser Thr Tyr Ser Leu Ser Ser Thr Leu
                260                 265                 270
Thr Leu Ser Lys Ala Asp Tyr Glu Lys His Lys Val Tyr Ala Cys Glu
            275                 280                 285
Val Thr His Gln Gly Leu Ser Ser Pro Val Thr Lys Ser Phe Asn Arg
    290                 295                 300
Gly Glu Cys
305

<210> SEQ ID NO 59
<211> LENGTH: 201
<212> TYPE: PRT
<213> ORGANISM: Homo sapiens

<400> SEQUENCE: 59

Asp Glu Val Ala Ile Leu Pro Ala Pro Gln Asn Leu Ser Val Leu Ser
1               5                   10                  15
Thr Asn Met Lys His Leu Leu Met Trp Ser Pro Val Ile Ala Pro Gly
                20                  25                  30
Glu Thr Val Tyr Tyr Ser Val Glu Tyr Gln Gly Glu Tyr Glu Ser Leu
            35                  40                  45
Tyr Thr Ser His Ile Trp Ile Pro Ser Ser Trp Cys Ser Leu Thr Glu
        50                  55                  60
Gly Pro Glu Cys Asp Val Thr Asp Asp Ile Thr Ala Thr Val Pro Tyr
65                  70                  75                  80
Asn Leu Arg Val Arg Ala Thr Leu Gly Ser Gln Thr Ser Ala Trp Ser
                85                  90                  95
Ile Leu Lys His Pro Phe Asn Arg Asn Ser Thr Ile Leu Thr Arg Pro
            100                 105                 110
Gly Met Glu Ile Thr Lys Asp Gly Phe His Leu Val Ile Glu Leu Glu
        115                 120                 125
Asp Leu Gly Pro Gln Phe Glu Phe Leu Val Ala Tyr Trp Arg Arg Glu
    130                 135                 140
Pro Gly Ala Glu Glu His Val Lys Met Val Arg Ser Gly Gly Ile Pro
145                 150                 155                 160
Val His Leu Glu Thr Met Glu Pro Gly Ala Ala Tyr Cys Val Lys Ala
                165                 170                 175
Gln Thr Phe Val Lys Ala Ile Gly Arg Tyr Ser Ala Phe Ser Gln Thr
            180                 185                 190
Glu Cys Val Glu Val Gln Gly Glu Ala
        195                 200

<210> SEQ ID NO 60
<211> LENGTH: 323
<212> TYPE: PRT
<213> ORGANISM: Homo sapiens

<400> SEQUENCE: 60

Asp Glu Val Ala Ile Leu Pro Ala Pro Gln Asn Leu Ser Val Leu Ser
1               5                   10                  15
Thr Asn Met Lys His Leu Leu Met Trp Ser Pro Val Ile Ala Pro Gly
                20                  25                  30
Glu Thr Val Tyr Tyr Ser Val Glu Tyr Gln Gly Glu Tyr Glu Ser Leu
```

-continued

```
                35                  40                  45
Tyr Thr Ser His Ile Trp Ile Pro Ser Ser Trp Cys Ser Leu Thr Glu
 50                  55                  60
Gly Pro Glu Cys Asp Val Thr Asp Asp Ile Thr Ala Thr Val Pro Tyr
 65                  70                  75                  80
Asn Leu Arg Val Arg Ala Thr Leu Gly Ser Gln Thr Ser Ala Trp Ser
                 85                  90                  95
Ile Leu Lys His Pro Phe Asn Arg Asn Ser Thr Ile Leu Thr Arg Pro
                100                 105                 110
Gly Met Glu Ile Pro Lys His Gly Phe His Leu Val Ile Glu Leu Glu
                115                 120                 125
Asp Leu Gly Pro Gln Phe Glu Phe Leu Val Ala Tyr Trp Thr Arg Glu
130                 135                 140
Pro Gly Ala Glu Glu His Val Lys Met Val Arg Ser Gly Gly Ile Pro
145                 150                 155                 160
Val His Leu Glu Thr Met Glu Pro Gly Ala Ala Tyr Cys Val Lys Ala
                165                 170                 175
Gln Thr Phe Val Lys Ala Ile Gly Arg Tyr Ser Ala Phe Ser Gln Thr
                180                 185                 190
Glu Cys Val Glu Val Gln Gly Glu Ala Gly Gly Gly Ser Gly Gly
                195                 200                 205
Gly Gly Ser Gly Gly Gly Ser Arg Thr Val Ala Ala Pro Ser Val
                210                 215                 220
Phe Ile Phe Pro Pro Ser Asp Glu Gln Leu Lys Ser Gly Thr Ala Ser
225                 230                 235                 240
Val Val Cys Leu Leu Asn Asn Phe Tyr Pro Arg Glu Ala Lys Val Gln
                245                 250                 255
Trp Lys Val Asp Asn Ala Leu Gln Ser Gly Asn Ser Gln Glu Ser Val
                260                 265                 270
Thr Glu Gln Asp Ser Lys Asp Ser Thr Tyr Ser Leu Ser Ser Thr Leu
                275                 280                 285
Thr Leu Ser Lys Ala Asp Tyr Glu Lys His Lys Val Tyr Ala Cys Glu
                290                 295                 300
Val Thr His Gln Gly Leu Ser Ser Pro Val Thr Lys Ser Phe Asn Arg
305                 310                 315                 320
Gly Glu Cys

<210> SEQ ID NO 61
<211> LENGTH: 201
<212> TYPE: PRT
<213> ORGANISM: Homo sapiens

<400> SEQUENCE: 61

Asp Glu Val Ala Ile Leu Pro Ala Pro Gln Asn Leu Ser Val Leu Ser
 1               5                  10                  15
Thr Asn Met Lys His Leu Leu Met Trp Ser Pro Val Ile Ala Pro Gly
                 20                  25                  30
Glu Thr Val Tyr Tyr Ser Val Glu Tyr Gln Gly Glu Tyr Glu Ser Leu
                 35                  40                  45
Tyr Thr Ser His Ile Trp Ile Pro Ser Ser Trp Cys Ser Leu Thr Glu
 50                  55                  60
Gly Pro Glu Cys Asp Val Thr Asp Asp Ile Thr Ala Thr Val Pro Tyr
 65                  70                  75                  80
Asn Leu Arg Val Arg Ala Thr Leu Gly Ser Gln Thr Ser Ala Trp Ser
```

-continued

```
                    85                  90                  95
Ile Leu Lys His Pro Phe Asn Arg Asn Ser Thr Ile Leu Thr Arg Pro
            100                 105                 110

Gly Met Glu Ile Pro Lys His Gly Phe His Leu Val Ile Glu Leu Glu
            115                 120                 125

Asp Leu Gly Pro Gln Phe Glu Phe Leu Val Ala Tyr Trp Thr Arg Glu
130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala
            195                 200

<210> SEQ ID NO 62
<211> LENGTH: 559
<212> TYPE: PRT
<213> ORGANISM: Homo sapiens

<400> SEQUENCE: 62

Val Pro Cys Val Ser Gly Gly Leu Pro Lys Pro Ala Asn Ile Thr Phe
1               5                   10                  15

Leu Ser Ile Asn Met Lys Asn Val Leu Gln Trp Thr Pro Pro Glu Gly
            20                  25                  30

Leu Gln Gly Val Lys Val Thr Tyr Thr Val Gln Tyr Phe Ile Tyr Gly
            35                  40                  45

Gln Lys Lys Trp Leu Asn Lys Ser Glu Cys Arg Asn Ile Asn Arg Thr
    50                  55                  60

Tyr Cys Asp Leu Ser Ala Glu Thr Ser Asp Tyr Glu His Gln Tyr Tyr
65                  70                  75                  80

Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Val Leu Thr Ala
            115                 120                 125

Pro Glu Lys Trp Lys Arg Asn Pro Glu Asp Leu Pro Val Ser Met Gln
130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
            195                 200                 205

Arg Thr Leu Lys Asp Gln Gly Gly Gly Ser Gly Gly Gly Ser
210                 215                 220

Gly Gly Gly Gly Ser Ala Ser Thr Lys Gly Pro Ser Val Phe Pro Leu
225                 230                 235                 240

Ala Pro Ser Ser Lys Ser Thr Ser Gly Gly Thr Ala Ala Leu Gly Cys
            245                 250                 255
```

```
Leu Val Lys Asp Tyr Phe Pro Glu Pro Val Thr Val Ser Trp Asn Ser
            260                 265                 270

Gly Ala Leu Thr Ser Gly Val His Thr Phe Pro Ala Val Leu Gln Ser
        275                 280                 285

Ser Gly Leu Tyr Ser Leu Ser Ser Val Val Thr Val Pro Ser Ser Ser
        290                 295                 300

Leu Gly Thr Gln Thr Tyr Ile Cys Asn Val Asn His Lys Pro Ser Asn
305                 310                 315                 320

Thr Lys Val Asp Lys Lys Val Glu Pro Lys Ser Cys Asp Lys Thr His
                325                 330                 335

Thr Cys Pro Pro Cys Pro Ala Pro Glu Ala Gly Ala Pro Ser Val
                340                 345                 350

Phe Leu Phe Pro Pro Lys Pro Lys Asp Thr Leu Met Ile Ser Arg Thr
                355                 360                 365

Pro Glu Val Thr Cys Val Val Val Asp Val Ser His Glu Asp Pro Glu
            370                 375                 380

Val Lys Phe Asn Trp Tyr Val Asp Gly Val Glu Val His Asn Ala Lys
385                 390                 395                 400

Thr Lys Pro Arg Glu Glu Gln Tyr Asn Ser Thr Tyr Arg Val Val Ser
                405                 410                 415

Val Leu Thr Val Leu His Gln Asp Trp Leu Asn Gly Lys Glu Tyr Lys
            420                 425                 430

Cys Lys Val Ser Asn Lys Ala Leu Pro Ser Ser Ile Glu Lys Thr Ile
                435                 440                 445

Ser Lys Ala Lys Gly Gln Pro Arg Glu Pro Gln Val Tyr Thr Leu Pro
            450                 455                 460

Pro Ser Arg Asp Glu Leu Thr Lys Asn Gln Val Ser Leu Thr Cys Leu
465                 470                 475                 480

Val Lys Gly Phe Tyr Pro Ser Asp Ile Ala Val Glu Trp Glu Ser Asn
                485                 490                 495

Gly Gln Pro Glu Asn Asn Tyr Lys Thr Thr Pro Pro Val Leu Asp Ser
            500                 505                 510

Asp Gly Ser Phe Phe Leu Tyr Ser Lys Leu Thr Val Asp Lys Ser Arg
                515                 520                 525

Trp Gln Gln Gly Asn Val Phe Ser Cys Ser Val Met His Glu Ala Leu
            530                 535                 540

His Asn His Tyr Thr Gln Lys Ser Leu Ser Leu Ser Pro Gly Lys
545                 550                 555

<210> SEQ ID NO 63
<211> LENGTH: 214
<212> TYPE: PRT
<213> ORGANISM: Homo sapiens

<400> SEQUENCE: 63

Val Pro Cys Val Ser Gly Gly Leu Pro Lys Pro Ala Asn Ile Thr Phe
1               5                   10                  15

Leu Ser Ile Asn Met Lys Asn Val Leu Gln Trp Thr Pro Pro Glu Gly
                20                  25                  30

Leu Gln Gly Val Lys Val Thr Tyr Thr Val Gln Tyr Phe Ile Tyr Gly
                35                  40                  45

Gln Lys Lys Trp Leu Asn Lys Ser Glu Cys Arg Asn Ile Asn Arg Thr
            50                  55                  60

Tyr Cys Asp Leu Ser Ala Glu Thr Ser Asp Tyr Glu His Gln Tyr Tyr
65              70                  75                  80
```

```
Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Leu Thr Ala
        115                 120                 125

Pro Glu Lys Trp Lys Arg Asn Pro Glu Asp Leu Pro Val Ser Met Gln
    130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
        195                 200                 205

Arg Thr Leu Lys Asp Gln
    210

<210> SEQ ID NO 64
<211> LENGTH: 19
<212> TYPE: PRT
<213> ORGANISM: Homo sapiens

<400> SEQUENCE: 64

Glu Glu Ile His Ala Glu Leu Arg Arg Phe Arg Arg Val Pro Cys Val
1               5                   10                  15

Ser Gly Gly

<210> SEQ ID NO 65
<211> LENGTH: 207
<212> TYPE: PRT
<213> ORGANISM: Homo sapiens

<400> SEQUENCE: 65

Leu Pro Lys Pro Ala Asn Ile Thr Phe Leu Ser Ile Asn Met Lys Asn
1               5                   10                  15

Val Leu Gln Trp Thr Pro Pro Glu Gly Leu Gln Gly Val Lys Val Thr
                20                  25                  30

Tyr Thr Val Gln Tyr Phe Ile Tyr Gly Gln Lys Lys Trp Leu Asn Lys
            35                  40                  45

Ser Glu Cys Arg Asn Ile Asn Arg Thr Tyr Cys Asp Leu Ser Ala Glu
50                  55                  60

Thr Ser Asp Tyr Glu His Gln Tyr Tyr Ala Lys Val Lys Ala Ile Trp
65                  70                  75                  80

Gly Thr Lys Cys Ser Lys Trp Ala Glu Ser Gly Arg Phe Tyr Pro Phe
                85                  90                  95

Leu Glu Thr Gln Ile Gly Pro Pro Glu Val Ala Leu Thr Thr Asp Glu
            100                 105                 110

Lys Ser Ile Ser Val Val Leu Thr Ala Pro Glu Lys Trp Lys Arg Asn
        115                 120                 125

Pro Glu Asp Leu Pro Val Ser Met Gln Gln Ile Tyr Ser Asn Leu Lys
    130                 135                 140

Tyr Asn Val Ser Val Leu Asn Thr Lys Ser Asn Arg Thr Trp Ser Gln
145                 150                 155                 160
```

```
Cys Val Thr Asn His Thr Leu Val Leu Thr Trp Leu Glu Pro Asn Thr
                165                 170                 175

Leu Tyr Cys Val His Val Glu Ser Phe Val Pro Gly Pro Pro Arg Arg
            180                 185                 190

Ala Gln Pro Ser Glu Lys Gln Cys Ala Arg Thr Leu Lys Asp Gln
        195                 200                 205

<210> SEQ ID NO 66
<211> LENGTH: 150
<212> TYPE: PRT
<213> ORGANISM: Homo sapiens

<400> SEQUENCE: 66

Cys Arg Asn Ile Asn Arg Thr Tyr Cys Asp Leu Ser Ala Glu Thr Ser
  1               5                  10                  15

Asp Tyr Glu His Gln Tyr Tyr Ala Lys Val Lys Ala Ile Trp Gly Thr
                 20                  25                  30

Lys Cys Ser Lys Trp Ala Glu Ser Gly Arg Phe Tyr Pro Phe Leu Glu
             35                  40                  45

Thr Gln Ile Gly Pro Pro Glu Val Ala Leu Thr Thr Asp Glu Lys Ser
         50                  55                  60

Ile Ser Val Val Leu Thr Ala Pro Glu Lys Trp Lys Arg Asn Pro Glu
 65                  70                  75                  80

Asp Leu Pro Val Ser Met Gln Gln Ile Tyr Ser Asn Leu Lys Tyr Asn
                 85                  90                  95

Val Ser Val Leu Asn Thr Lys Ser Asn Arg Thr Trp Ser Gln Cys Val
            100                 105                 110

Thr Asn His Thr Leu Val Leu Thr Trp Leu Glu Pro Asn Thr Leu Tyr
            115                 120                 125

Cys Val His Val Glu Ser Phe Val Pro Gly Pro Pro Arg Arg Ala Gln
        130                 135                 140

Pro Ser Glu Lys Gln Cys
145                 150

<210> SEQ ID NO 67
<211> LENGTH: 196
<212> TYPE: PRT
<213> ORGANISM: Homo sapiens

<400> SEQUENCE: 67

Leu Pro Ala Pro Gln Asn Leu Ser Val Leu Ser Thr Asn Met Lys His
  1               5                  10                  15

Leu Leu Met Trp Ser Pro Val Ile Ala Pro Gly Glu Thr Val Tyr Tyr
                 20                  25                  30

Ser Val Glu Tyr Gln Gly Glu Tyr Glu Ser Leu Tyr Thr Ser His Ile
             35                  40                  45

Trp Ile Pro Ser Ser Trp Cys Ser Leu Thr Gly Pro Glu Cys Asp
         50                  55                  60

Val Thr Asp Asp Ile Thr Ala Thr Val Pro Tyr Asn Leu Arg Val Arg
 65                  70                  75                  80

Ala Thr Leu Gly Ser Gln Thr Ser Ala Trp Ser Ile Leu Lys His Pro
                 85                  90                  95

Phe Asn Arg Asn Ser Thr Ile Leu Thr Arg Pro Gly Met Glu Ile Thr
            100                 105                 110

Lys Asp Gly Phe His Leu Val Ile Glu Leu Glu Asp Leu Gly Pro Gln
            115                 120                 125
```

```
Phe Glu Phe Leu Val Ala Tyr Trp Arg Arg Glu Pro Gly Ala Glu Glu
    130                 135                 140

His Val Lys Met Val Arg Ser Gly Gly Ile Pro Val His Leu Glu Thr
145                 150                 155                 160

Met Glu Pro Gly Ala Ala Tyr Cys Val Lys Ala Gln Thr Phe Val Lys
                165                 170                 175

Ala Ile Gly Arg Tyr Ser Ala Phe Ser Gln Thr Glu Cys Val Glu Val
            180                 185                 190

Gln Gly Glu Ala
        195

<210> SEQ ID NO 68
<211> LENGTH: 203
<212> TYPE: PRT
<213> ORGANISM: Homo sapiens

<400> SEQUENCE: 68

Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
        35                  40                  45

Tyr Thr Ser His Ile Trp Ile Pro Ser Ser Trp Cys Ser Leu Thr Glu
    50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
            100                 105                 110

Gly Met Glu Ile Pro Lys His Gly Phe His Leu Val Ile Glu Leu Glu
        115                 120                 125

Asp Leu Gly Pro Gln Phe Glu Phe Leu Val Ala Tyr Trp Thr Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala Ile Pro
        195                 200

<210> SEQ ID NO 69
<211> LENGTH: 196
<212> TYPE: PRT
<213> ORGANISM: Homo sapiens

<400> SEQUENCE: 69

Leu Pro Ala Pro Gln Asn Leu Ser Val Leu Ser Thr Asn Met Lys His
1               5                   10                  15

Leu Leu Met Trp Ser Pro Val Ile Ala Pro Gly Glu Thr Val Tyr Tyr
            20                  25                  30

Ser Val Glu Tyr Gln Gly Glu Tyr Glu Ser Leu Tyr Thr Ser His Ile
        35                  40                  45
```

-continued

Trp Ile Pro Ser Ser Trp Cys Ser Leu Thr Glu Gly Pro Glu Cys Asp
 50                  55                  60

Val Thr Asp Asp Ile Thr Ala Thr Val Pro Tyr Asn Leu Arg Val Arg
 65                  70                  75                  80

Ala Thr Leu Gly Ser Gln Thr Ser Ala Trp Ser Ile Leu Lys His Pro
                 85                  90                  95

Phe Asn Arg Asn Ser Thr Ile Leu Thr Arg Pro Gly Met Glu Ile Pro
                100                 105                 110

Lys His Gly Phe His Leu Val Ile Glu Leu Glu Asp Leu Gly Pro Gln
                115                 120                 125

Phe Glu Phe Leu Val Ala Tyr Trp Thr Arg Glu Pro Gly Ala Glu Glu
130                 135                 140

His Val Lys Met Val Arg Ser Gly Gly Ile Pro Val His Leu Glu Thr
145                 150                 155                 160

Met Glu Pro Gly Ala Ala Tyr Cys Val Lys Ala Gln Thr Phe Val Lys
                165                 170                 175

Ala Ile Gly Arg Tyr Ser Ala Phe Ser Gln Thr Glu Cys Val Glu Val
                180                 185                 190

Gln Gly Glu Ala
                195

<210> SEQ ID NO 70
<211> LENGTH: 135
<212> TYPE: PRT
<213> ORGANISM: Homo sapiens

<400> SEQUENCE: 70

Cys Ser Leu Thr Glu Gly Pro Glu Cys Asp Val Thr Asp Asp Ile Thr
  1               5                  10                  15

Ala Thr Val Pro Tyr Asn Leu Arg Val Arg Ala Thr Leu Gly Ser Gln
                 20                  25                  30

Thr Ser Ala Trp Ser Ile Leu Lys His Pro Phe Asn Arg Asn Ser Thr
             35                  40                  45

Ile Leu Thr Arg Pro Gly Met Glu Ile Thr Lys Asp Gly Phe His Leu
 50                  55                  60

Val Ile Glu Leu Glu Asp Leu Gly Pro Gln Phe Glu Phe Leu Val Ala
 65                  70                  75                  80

Tyr Trp Arg Arg Glu Pro Gly Ala Glu Glu His Val Lys Met Val Arg
                 85                  90                  95

Ser Gly Gly Ile Pro Val His Leu Glu Thr Met Glu Pro Gly Ala Ala
                100                 105                 110

Tyr Cys Val Lys Ala Gln Thr Phe Val Lys Ala Ile Gly Arg Tyr Ser
                115                 120                 125

Ala Phe Ser Gln Thr Glu Cys
                130                 135

<210> SEQ ID NO 71
<211> LENGTH: 135
<212> TYPE: PRT
<213> ORGANISM: Homo sapiens

<400> SEQUENCE: 71

Cys Ser Leu Thr Glu Gly Pro Glu Cys Asp Val Thr Asp Asp Ile Thr
  1               5                  10                  15

Ala Thr Val Pro Tyr Asn Leu Arg Val Arg Ala Thr Leu Gly Ser Gln
                 20                  25                  30

```
Thr Ser Ala Trp Ser Ile Leu Lys His Pro Phe Asn Arg Asn Ser Thr
        35                  40                  45

Ile Leu Thr Arg Pro Gly Met Glu Ile Pro Lys His Gly Phe His Leu
    50                  55                  60

Val Ile Glu Leu Glu Asp Leu Gly Pro Gln Phe Glu Phe Leu Val Ala
65                  70                  75                  80

Tyr Trp Thr Arg Glu Pro Gly Ala Glu Glu His Val Lys Met Val Arg
            85                  90                  95

Ser Gly Gly Ile Pro Val His Leu Glu Thr Met Glu Pro Gly Ala Ala
            100                 105                 110

Tyr Cys Val Lys Ala Gln Thr Phe Val Lys Ala Ile Gly Arg Tyr Ser
        115                 120                 125

Ala Phe Ser Gln Thr Glu Cys
    130                 135

<210> SEQ ID NO 72
<211> LENGTH: 15
<212> TYPE: PRT
<213> ORGANISM: Homo sapiens

<400> SEQUENCE: 72

Gly Gly Gly Gly Ser Gly Gly Gly Gly Ser Gly Gly Gly Gly Ser
1               5                   10                  15
```

SOLUBLE INTERLEUKIN-20 RECEPTOR

This application is a continuation of U.S. application Ser. No. 09/745,792, now U.S. Pat. No. 7,122,632, filed Dec. 22, 2000, which claims the benefit of U.S. Provisional Application Ser. No. 60/171,966, filed Dec. 23, 1999, and U.S. Provisional Application Ser. No. 60/213,416, filed Jun. 22, 2000, all of which are herein incorporated by reference in their entirety.

BACKGROUND OF THE INVENTION

The teachings of all of the references cited herein are incorporated in their entirety herein by reference.

Cytokines are soluble proteins that influence the growth and differentiation of many cell types. Their receptors are composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons (IFNs) are members of the type II cytokine receptor family (CRF2), based upon a characteristic 200 residue extracellular domain. The demonstrated in vivo activities of these interferons illustrate the enormous clinical potential of, and need for, other cytokines, cytokine agonists, and cytokine antagonists. Some cytokines are involved in the inflammatory cascade and can promote such diseases as rheumatoid arthritis, Crohn's disease, psoriasis, heart disease etc. Thus, there is a need to discover cytokines and their receptors that are involved in inflammation. One can then use the isolated soluble receptors of the cytokine to inhibit the cytokine-mediated inflammation.

BRIEF DESCRIPTION OF THE DRAWINGS

FIG. 1 depicts the heterotetramer produced by example 5. The soluble receptor construct, designated 10, is comprised of two IL-20 binding site polypeptide chains designated 12 and 14. Each binding site is comprised of the extracellular domain of IL-20RA, designated 16, and the extracellular domain of IL-20RB designated 18. The extracellular domain, 16, of IL-20RA is linked to the constant heavy one (CH1) domain, 20, of the human immunoglobulin gamma 1 heavy chain constant region via linker 22, which is SEQ ID NO:72. The CH1 domain, 20, is then linked to the CH2 domain, 24, via hinge region 23. The CH2 domain, 24, is linked to the CH3 domain, 26, via hinge region 25. Chains 12 and 14 are disulfide-bonded together by means of disulfide bonds 28 and 30. Extracellular domain, 18, of IL-20RB is linked to the constant region of the human kappa light chain (CL), 34 of FIG. 1 via polypeptide linker 32. The constant light chain 34 forms a disulfide bonded, 36, with hinge region 23.

FIG. 2 depicts a construct of the present invention where the two IL-20 binding polypeptides, 12 and 14, are not disulfide bonded together, having hinge region, 27.

FIG. 3 shows a very simple soluble receptor 38 of the present invention wherein extracellular domain, 16, of IL-20RA is connected to the extracellular domain, 18, of IL-20RB by means of a polypeptide linker, 40. The polypeptide linker extends from the amino terminus of extracellular domain, 16, of IL-20RA and is connected to the carboxyl terminus of the extracellular domain, 18, of IL-20RB.

FIG. 4 shows an embodiment that has the extracellular domain, 16, of IL-20RA linked to the extracellular domain, 18, of IL-20RB by means of linker 40, as in FIG. 3. While the extracellular domain, 16, of IL-20RA is linked to the CH1 domain, 20, as in FIG. 1 by means of polypeptide linker 42.

FIG. 5 shows another possible embodiment of the present invention. In this embodiment, a polypeptide linker 44, links the carboxyl terminus of the extracellular domain, 18, of IL-20RB with the amino terminus of the extracellular domain, 16, of IL-20RA. A polypeptide linker 46, extends from the carboxy terminus of the extracellular domain, 16, of IL-20RA to the CH2 domain 24.

FIG. 6 shows another possible embodiment of the present invention. The soluble IL-20 receptor of FIG. 6 is identical to that of FIG. 1 except for the CH3 domain, 26 of FIG. 1, is not present on the embodiment of FIG. 6.

FIG. 7 shows a soluble IL-20 receptor construct that is identical to the construct of FIG. 1 except both the CH2, and CH3 domains are absent.

FIG. 8 shows a construct wherein both IL-20RA, 16, and IL-20RB have a polypeptide linker, 48, fused to their respective carboxyl termini. Each polypeptide linker has two cysteine residues such that when they are expressed the cysteines form two disulfide bonds, 50 and 52.

DESCRIPTION OF THE INVENTION

Figure 1:
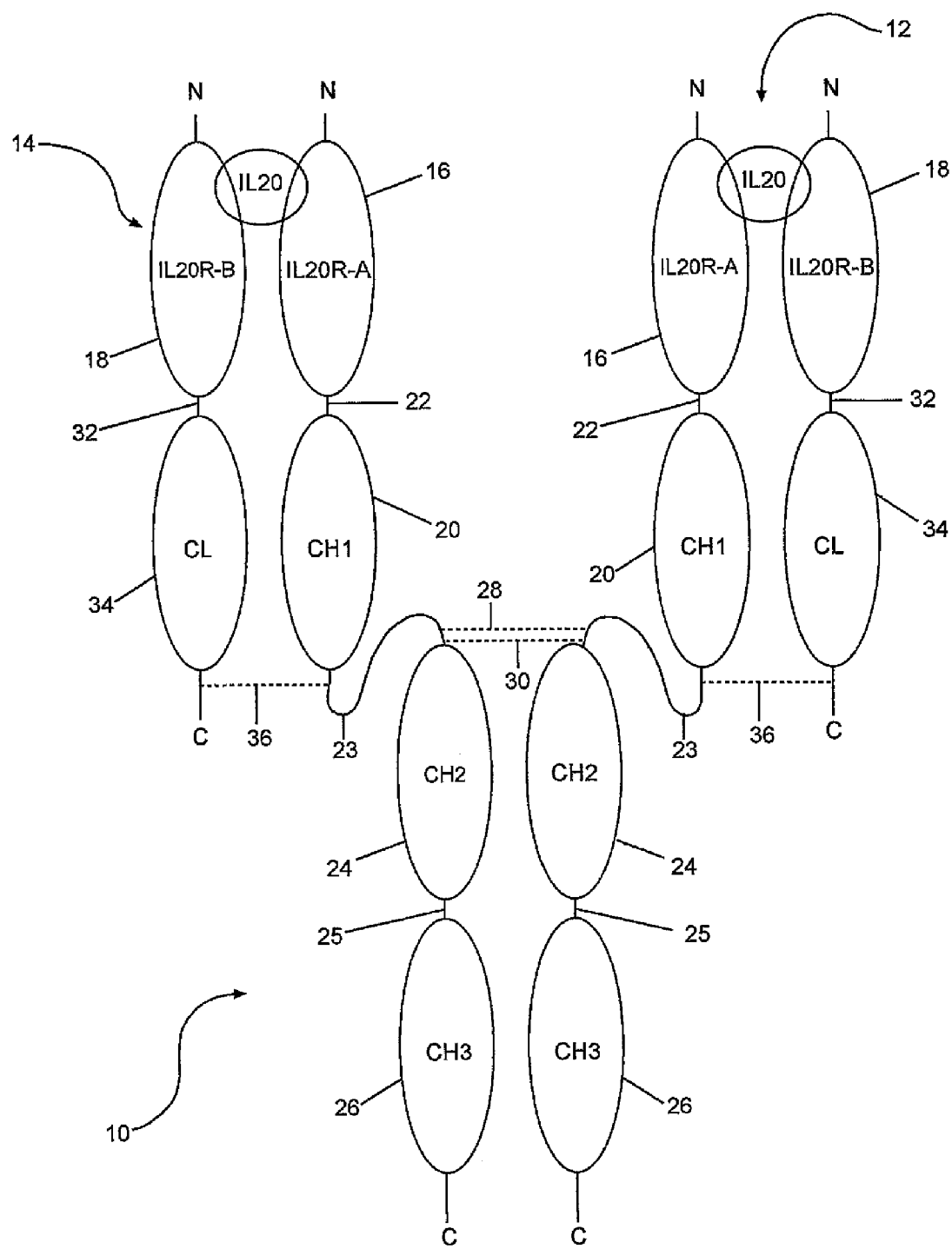
FIGS. 1-8 illustrate a representative number of embodiments of the present invention. Common elements in each of the drawings are given the same number.

The present invention fills this need by providing a newly discovered soluble receptor to Interleukin-20 (IL-20). The soluble receptor can be used to down-regulate IL-20 and thus treat inflammatory diseases such as psoriasis and inflammatory lung diseases.

IL-20 was formally called 'Zcyto10', (International Patent Publication No. WO 99/27103) and has the amino acid sequences of SEQ ID NOs: 1-9. The receptor to IL-20 is comprised of two chains, an alpha chain and a beta chain. The alpha chain, hereinafter referred to as IL-20RA, was formally called ZcytoR7. See U.S. Pat. No. 5,945,511. The beta chain, hereinafter referred to as IL-20RB, was formally called DIRS1. See International Patent Application No. PCT/US99/03735. The present invention is a soluble receptor comprised of the extracellular domain of IL-20RA and the extracellular domain of IL-20RB.

The present invention encompasses an isolated soluble receptor comprised of an 'IL-20RA' subunit and an 'IL-20RB' subunit, wherein the IL-20A subunit is comprised of a polypeptide having an amino acid sequence selected from the group consisting of SEQ ID NOs: 12, 38, 55, 63 and 65, and the IL-20RB subunit is comprised of a polypeptide having an amino acid sequence selected from the group consisting of SEQ ID NOs: 15, 59, 61, 67, 68 and 69. The IL-20RA and IL-20RB subunits are generally linked together by a polypeptide linker. The linking can be by any means but generally by a peptide bond or a disulfide bond between a polypeptide connected to the IL20RA subunit and a polypeptide connected to the IL-20RB subunit. The present invention is also directed towards isolated polynucleotides that encode the novel IL-20RA and IL-20RB polypeptides of the present invention.

In one embodiment the IL-20RA subunit is fused to the constant region of the heavy chain of an immunoglobulin (Ig) molecule or a portion thereof and the IL-20RB subunit is fused to the constant region of the light chain of an Ig molecule such that the constant region of the light chain is disulfide bonded to the constant region of the heavy chain, generally to a cysteine residue on the hinge region of the heavy chain. Also the opposite can occur, the IL-20RA subunit can be fused to the constant region of the light chain of an Ig molecule and the IL-20RB subunit can be fused to the constant region of the heavy chain of an Ig molecule.

In one embodiment of the soluble receptor of the present invention, the IL-20RA subunit fused to the constant region of the heavy chain is comprised of an amino acid sequence selected from the group consisting of SEQ ID NOs: 23, 53, 54 and 62, and the IL-20RB subunit fused to the constant region of the light chain of the Ig molecule is comprised of an amino acid sequence selected from the group consisting of SEQ ID NOs: 21, 57, 58, and 60.

Also claimed is a protein having a first polypeptide and a second polypeptide wherein the first polypeptide is comprised of an amino acid sequence of SEQ ID NO: 66 and the second polypeptide is comprised of an amino acid sequence selected from the group consisting of SEQ ID NOs: 70 and 71. The resultant protein can be used to generate antibodies to the IL-20RA subunit and the IL-20RB subunit.

Definitions

Prior to setting forth the invention in more detail, it may be helpful to the understanding thereof to define the following terms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

As used herein, the term "antibody fusion protein" refers to a recombinant molecule that comprises an antibody component and a therapeutic agent. Examples of therapeutic agents suitable for such fusion proteins include immunomodulators ("antibody-immunomodulator fusion protein") and toxins ("antibody-toxin fusion protein").

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCT-Tgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78 (1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nucleotides in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear, monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

As was stated above, IL-20 (formally called Zcyto10) is defined and methods for producing it and antibodies to IL-20 are contained in International Patent Application No. PCT/US98/25228, publication no. WO 99/27103, published Nov. 25, 1998 and U.S. patent application Ser. No. 09/313,458 filed May 17, 1999. The polynucleotide and polypeptide of human IL-20 are represented by SEQ ID NOs: 1-4, and mouse IL-20 by SEQ ID NOs: 5-9.

The receptor to IL-20 has been discovered and is a heterodimer comprised of the polypeptide termed 'IL-20RA' (formally called Zcytor7) and a polypeptide termed 'IL-20RB'. The IL-20RA polypeptide, nucleic acid that encodes it, antibodies to IL-20RA and methods for producing it are disclosed in U.S. Pat. No. 5,945,511 issued Aug. 31, 1999. SEQ ID NOs: 10-12 are the IL-20RA polynucleotides and polypeptides. The extracellular domain of the human IL-20RA is comprised of a polypeptide selected from the group consisting of SEQ ID NOs: 12, 55, 63 and 65, the full-length receptor subunit being comprised of SEQ ID NO: 11. The extracellular domain of mouse IL-20RA is SEQ ID NO: 38, SEQ ID NO: 37 being the entire mouse IL-20RA.

The extracellular domain of IL-20RB SEQ ID NOs: 13-14, and a variant SEQ ID NOs: 18 and 19) is comprised of a polypeptide selected from the group consisting of SEQ ID NOs: 15, 59, 61, 67, 68 and 69. Preferably, the extracellular domain of the IL-20RA polypeptide and the extracellular domain of the IL-20RB polypeptide are covalently linked together. In a preferred embodiment one extracellular subunit polypeptide has a constant region of a heavy chain of an immunoglobulin fused to its carboxy terminus and the other extracellular subunit has a constant light chain of an immunoglobulin (Ig) fused to its carboxy terminus such that the two polypeptides come together to form a soluble receptor and a disulfide bond is formed between the heavy and the light Ig chains. In another method, a peptide linker could be fused to the two carboxy-termini of the polypeptides to form a covalently bonded soluble receptor.

SEQ ID NOs: 22 and 23 are constructs of the extracellular domain of IL-20RA fused to a mutated human immunoglobulin gamma 1 constant region produced according to the procedure set forth in example 5. SEQ ID NO: 62 is the predicted mature sequence without the signal sequence. SEQ ID NOs: 20 and 21 are constructs of the extracellular domain of IL-20RB fused to wild type human immunoglobulin kappa light chain constant region produced according to the procedure of example 5. SEQ ID NO: 60 is the predicted mature sequence without the signal sequence. FIG. 1 depicts the heterotetramer produced by example 5.

SEQ ID NOs: 52 and 53 are constructs of the extracellular domain of IL-20RA fused to a mutated human immunoglobulin gamma 1 constant region produced according to the procedure set forth in example 12. SEQ ID NO: 54 is the predicted mature sequence without the signal sequence. SEQ ID NOs: 56 and 57 are constructs of the extracellular domain of IL-20RB fused to wild type human immunoglobulin kappa light chain constant region produced according to the procedure of example 12. SEQ ID NO: 58 is the predicted mature sequence without the signal sequence. The resultant heterotetramer is almost identical to that produced by example 5, the primary difference being the absence of a polypeptide linker between the extracellular domains and the beginning of the Ig constant regions, 22 in FIG. 1. Hereinafter, the term "extracellular domain of a receptor" means the extracellular domain of the receptor or a portion of the extracellular domain that is necessary for binding to its ligand, in this case the ligand being IL-20.

One can link together the extracellular domains of IL-20RA and IL-20RB in a number of ways such that the resultant soluble receptor can bind to IL-20. FIGS. 1-8 illustrate a representative number of embodiments of the present invention. Common elements in each of the drawings are given the same number. FIG. 1 represents the embodiment of the present invention produced according to example 5 below. The soluble receptor construct, designated 10, is comprised of two IL-20 binding site polypeptide chains designated 12 and 14. Each binding site is comprised of the extracellular domain of IL-20RA, designated 16, and the extracellular domain of IL-20RB designated 18.

The extracellular domain, 16, of IL-20RA is linked to the constant heavy one (CH1) domain, 20, of the human immunoglobulin gamma 1 heavy chain constant region via linker 22, which is SEQ ID NO:72. The CH1 domain, 20, is then linked to the CH2 domain, 24, via hinge region 23. The CH2 domain, 24, is linked to the CH3 domain, 26, via hinge region 25.

Comparing the construct of FIG. 1 with SEQ ID NO:22, the extracellular domain, 16, of IL-20RA extends from amino acid residues 36, a valine, to and including amino acid residue 249, a glutamine of SEQ ID NO:22. Polypeptide linker, 22, extends from amino acid residue 250, a glycine to and including amino acid residue 264, a serine, of SEQ ID NO:22. The CH1 domain, 22 of FIG. 1, extends from amino acid residue 265, an alanine, to and including amino acid residue 362, a valine, of SEQ ID NO:22. Hinge region 23 of FIG. 1 extends from amino acid residue 363, a glutamic acid to and including amino acid residue 377, a proline, of SEQ ID NO: 22. Chains 12 and 14 are disulfide-bonded together by means of disulfide bonds 28 and 30. The disulfide bonds are formed between the heavy chains by the cysteine residues at positions 373 and 376 of SEQ ID NO: 22 of each of the two heavy chains.

Extracellular domain, 18, of IL-20RB is linked to the constant region of the human kappa light chain (CL), 34 of FIG. 1 via polypeptide linker 32, which is the polypeptide SEQ ID NO: 72. The extracellular domain, 18, of IL-20RB extends from amino acid residue 30, a valine, to and including amino acid residue 230, an alanine, of SEQ ID NO: 20. Polypeptide linker, 32, extends from amino acid residue 231, a glycine, to and including amino acid residue 245, a serine, of SEQ ID NO:20. The kappa constant light region, 34, extends from amino acid residue 246, an arginine, to and including the final amino acid residue 352, a cysteine, of SEQ ID NO:20. The cysteine at position 352 of SEQ ID NO: 20 forms a disulfide bond, 36 in FIG. 1, with the cysteine at position 367 of SEQ ID NO: 22. The constant light chain 34 is thus linked to the hinge region, 23, by disulfide bond, 36. In this way, the extracellular domain, 16, of IL-20RA is linked to the extracellular domain, 18, of IL-20RB to form a soluble receptor.

Figure 2:
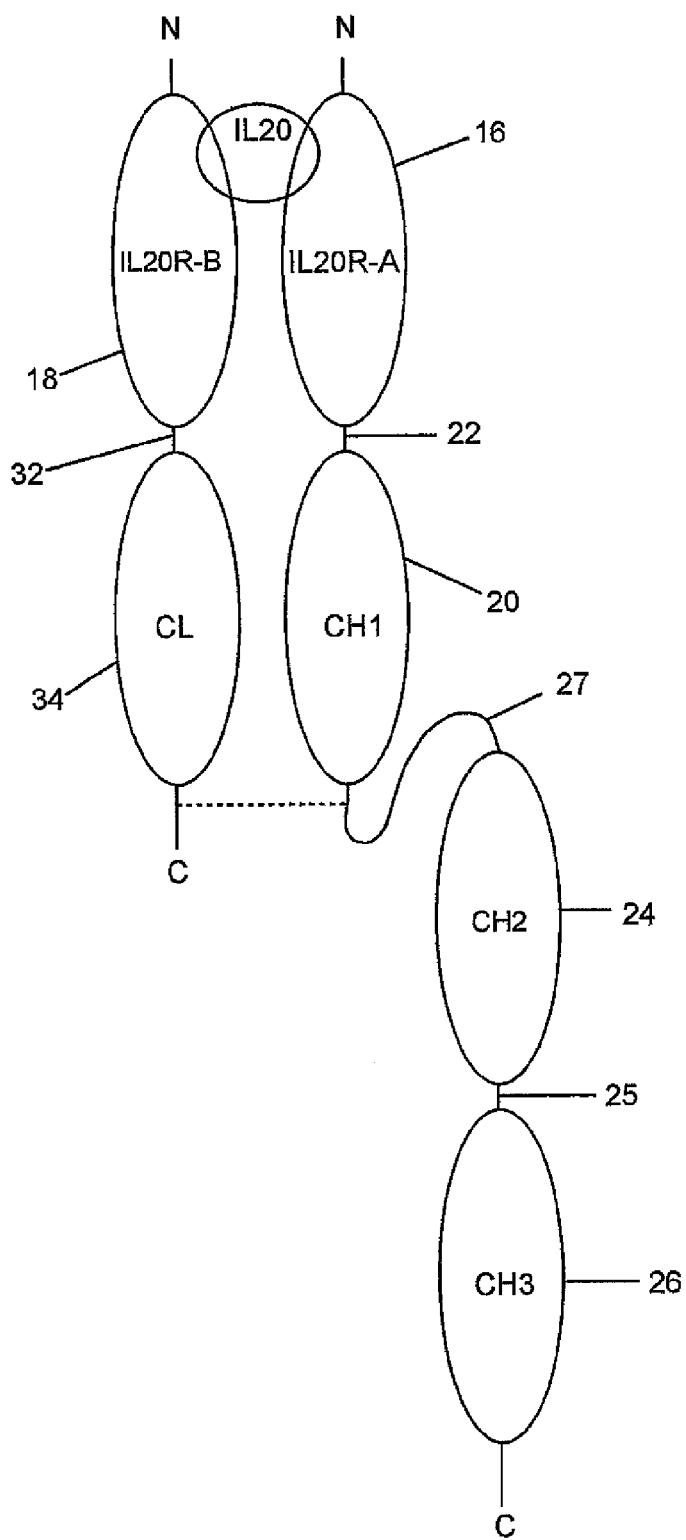

If the cysteine residues at positions 373 and 376 of SEQ ID NO:22 were changed to different amino acid residues, the two IL-20 binding polypeptides, 12 and 14, would not be disulfide bonded together and would form a construct shown in FIG. 2. having hinge region, 27.

Figure 3:
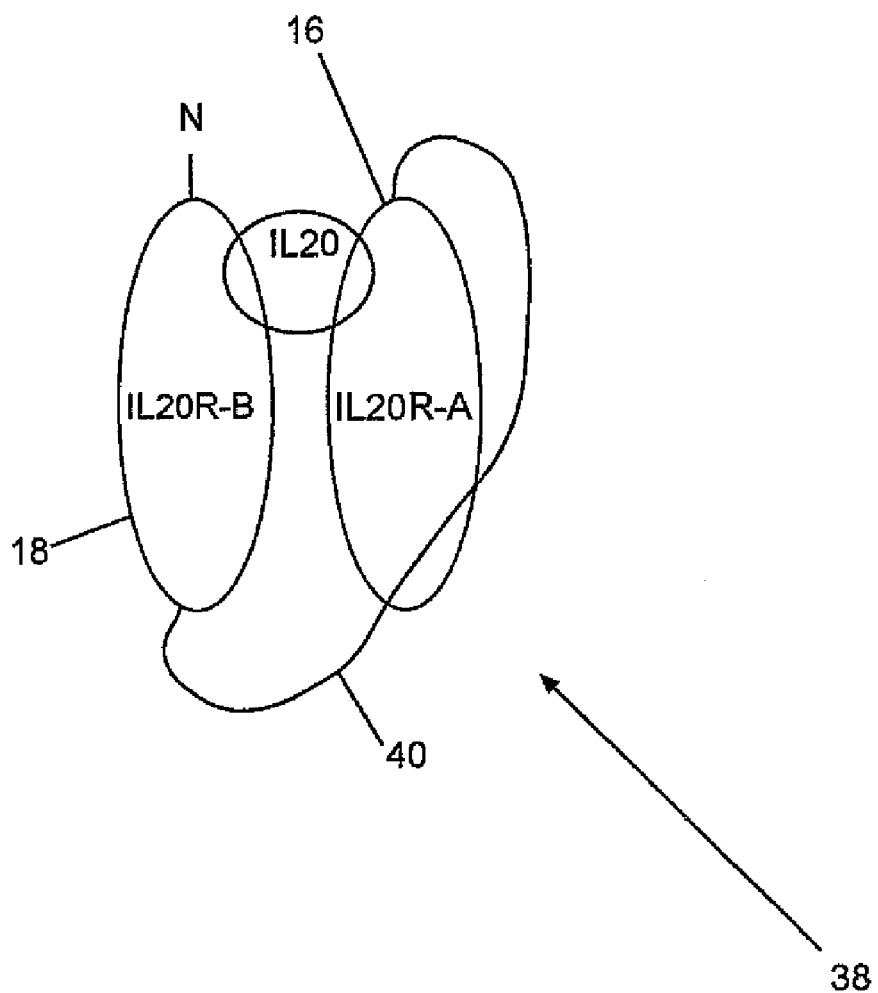

FIG. 3 shows a very simple soluble receptor 38 of the present invention wherein extracellular domain, 16, of IL-20RA is connected to the extracellular domain, 18, of IL-20RB by means of a polypeptide linker, 40. The polypeptide linker extends from the amino terminus of extracellular domain, 16, of IL-20RA and is connected to the carboxyl terminus of the extracellular domain, 18, of IL-20RB. The polypeptide linker should be between 100-240 amino acids in length, preferably about 170 amino acid residues in length. A suitable linker would be comprised of glycine and serine residues. A possible linker would be multiple units of SEQ ID NO: 72, preferably about 12.

Figure 4:
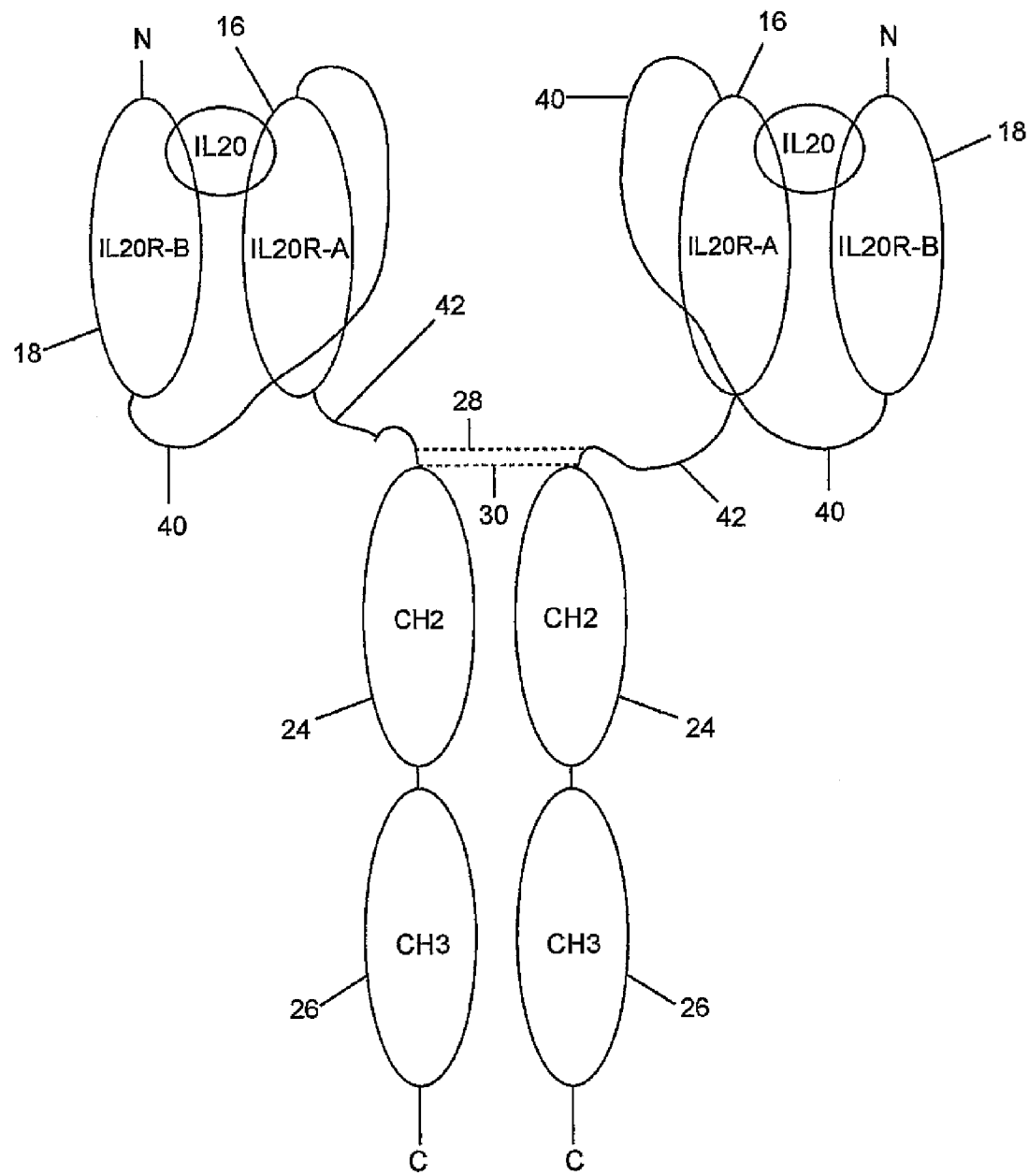

FIG. 4 shows an embodiment that has the extracellular domain, 16, of IL-20RA linked to the extracellular domain, 18, of IL-20RB by means of linker 40, as in FIG. 3. While the extracellular domain, 16, of IL-20RA is linked to the CH1 domain, 20, as in FIG. 1 by means of polypeptide linker 42, which should be about 30 amino acid residues in length. An ideal linker would be comprised of glycine and serine as in SEQ ID NO: 72, and the hinge sequence, 23 of FIG. 1.

Figure 5:
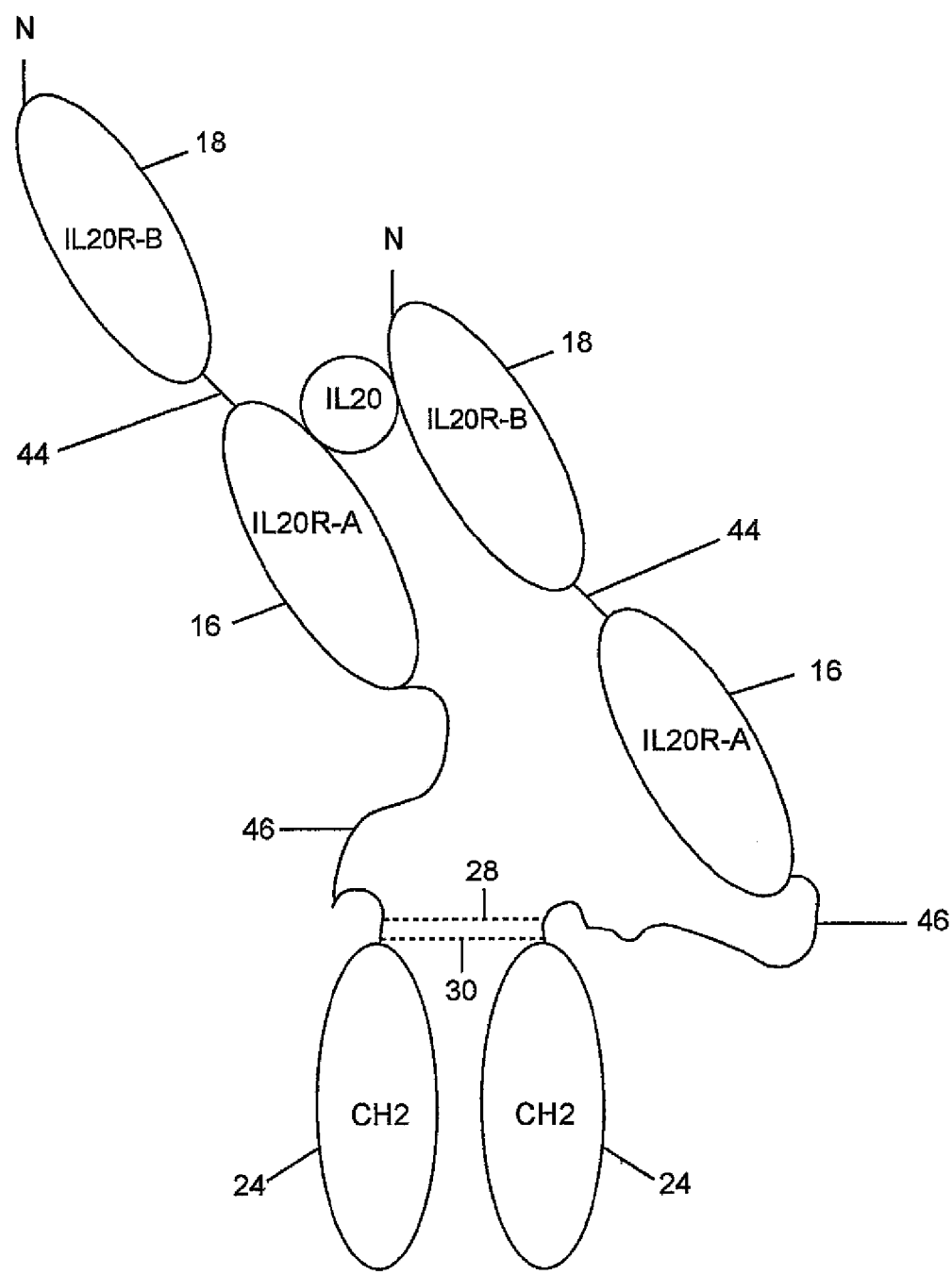

FIG. 5 shows another possible embodiment of the present invention. In this embodiment, a polypeptide linker 44 of about 15 amino acid residue, e.g. SEQ ID NO: 72, links the carboxyl terminus of the extracellular domain, 18, of IL-20RB with the amino terminus of the extracellular domain, 16, of IL-20RA. A polypeptide linker 46 of about 30 amino acid residues extends from the carboxy terminus of the extracellular domain, 16, of IL-20RA to the CH2 domain. The carboxyl terminus of linker 46 would preferably be comprised of the hinge region extending from amino acid residue 363, a glutamic acid to and including amino acid residue 377, a proline, of SEQ ID NO: 22. Nonetheless, polypeptide linker 46 would ideally have at least one cysteine residue at its carboxyl terminus so a disulfide bond could be formed.

Figure 6:
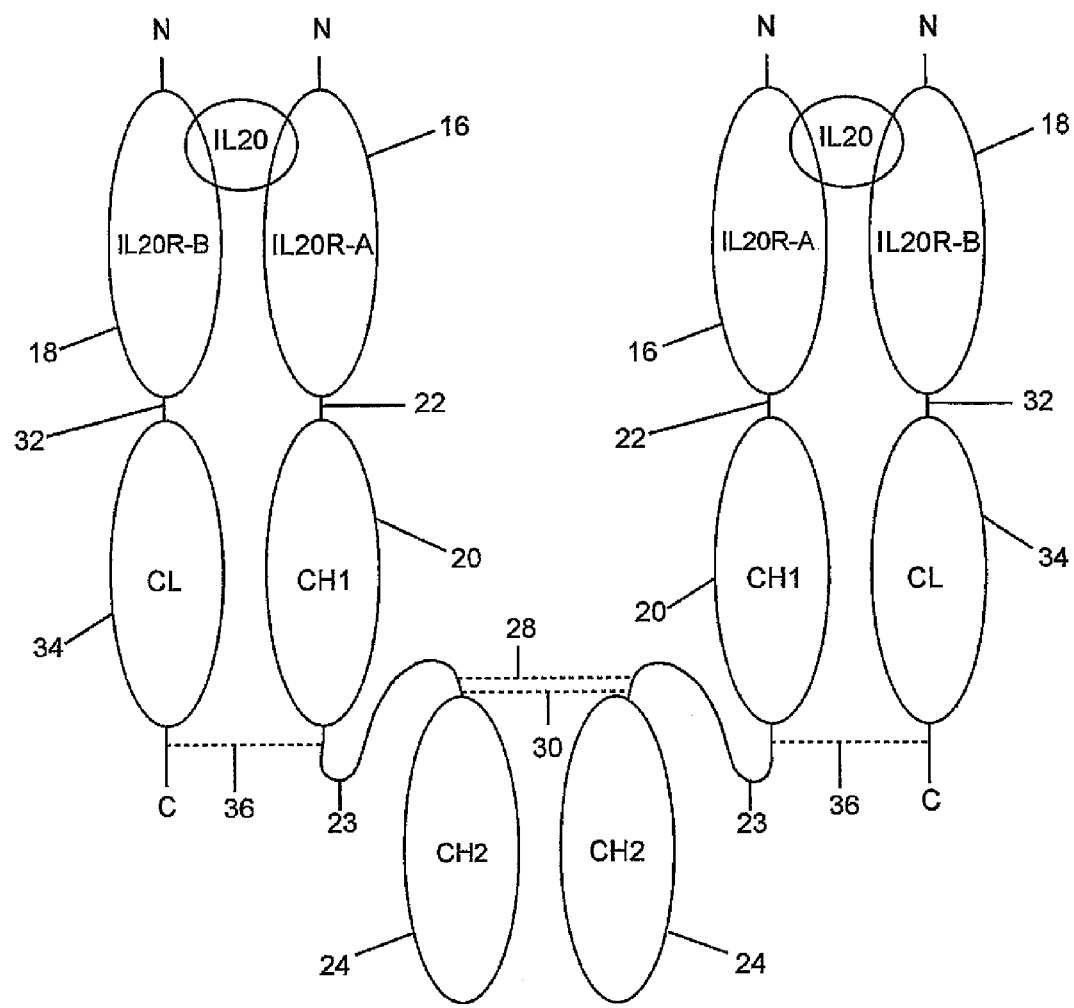

The soluble IL-20 receptor of FIG. 6 is identical to that of FIG. 1 except for the CH3 domain, 26 of FIG. 1, is not present on the embodiment of FIG. 6. The CH3 region begins at amino acid residue 488, a glycine, and extends to the last residue 594 of SEQ ID NO: 22.

Figure 7:
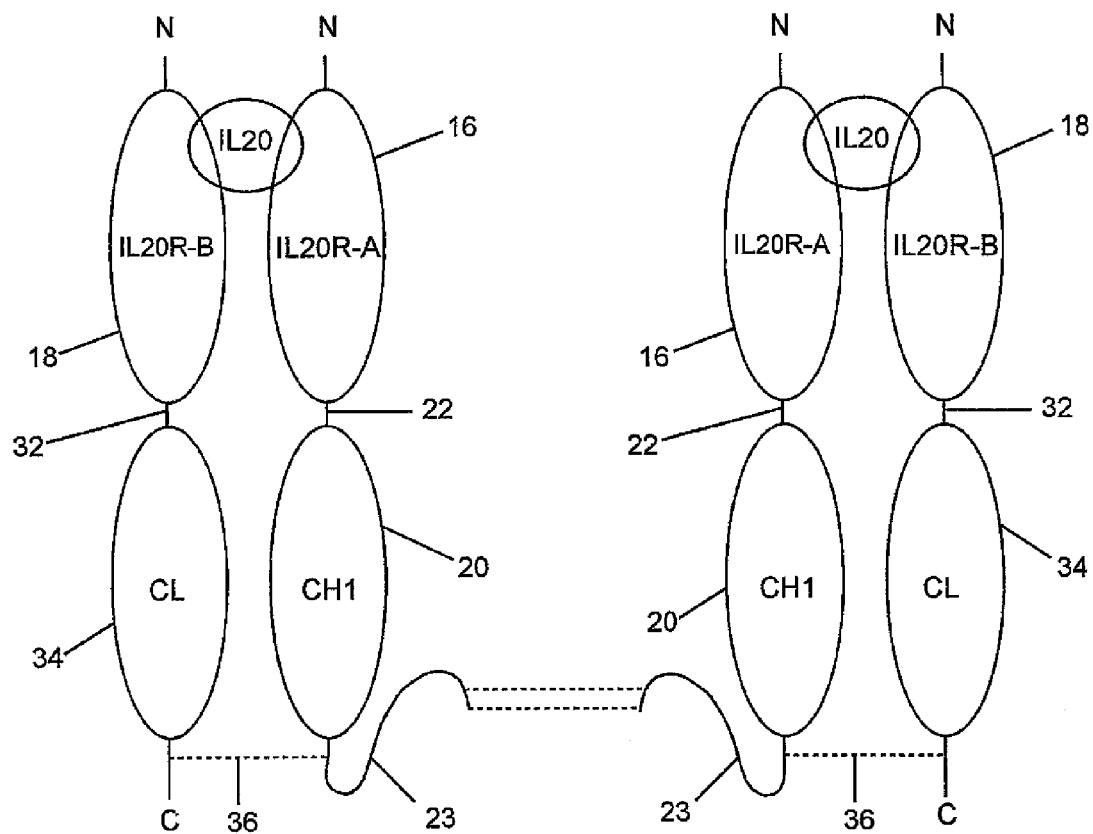

FIG. 7 shows a soluble IL-20 receptor construct that is identical to the construct of FIG. 1 except both the CH2, and CH3 domains are absent. The CH2 and CH3 domains run from amino acid residue 378, an alanine, to the end of the polypeptide sequence of SEQ ID NO: 22.

Figure 8:
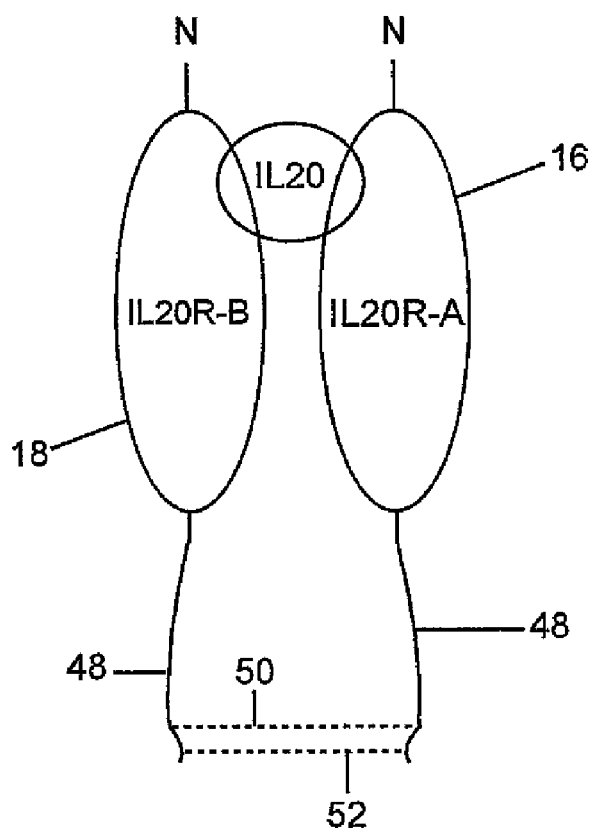

FIG. 8 shows a construct wherein both IL-20RA, 16, and IL-20RB have a polypeptide linker, 48, fused to their respective carboxyl termini. Each polypeptide linker has two cysteine residues such that when they are expressed the cysteines form two disulfide bonds, 50 and 52. In this case the polypeptide linker is comprised of the hinge region, 23 in FIG. 1. The hinge region is comprised of amino acid residues 363, a glutamine, to and including amino acid residue 377 of SEQ ID NO: 22.

In another aspect of the invention, a method is provided for producing a soluble receptor comprised of extracellular domains of IL-20RA and IL-20RB comprising (a) introducing into a host cell a first DNA sequence comprised of a transcriptional promoter operatively linked to a first secretory signal sequence followed downstream by and in proper reading frame the DNA that encodes the extracellular portion of IL-20RA and the DNA that encodes an immunoglobulin light chain constant region; (b) introducing into the host cell a second DNA construct comprised of a transcriptional promoter operatively linked to a second secretory signal followed downstream by and in proper reading frame a DNA sequence that encodes the extracellular portion of IL-20RB and a DNA sequence that encodes an immunoglobulin heavy chain constant region domain selected from the group consisting of $C_H1$, $C_H2$, $C_H3$ and $C_H4$; (c) growing the host cell in an appropriate growth medium under physiological conditions to allow the secretion of a fusion protein comprised of the extracellular domain of IL-20RA and IL-20RB; and (d) isolating the polypeptide from the host cell. In one embodiment, the second DNA sequence further encodes an immunoglobulin heavy chain hinge region wherein the hinge region is joined to the heavy chain constant region domain. In another embodiment, the second DNA sequence further encodes an immunoglobulin variable region joined upstream of and in proper reading frame with the immunoglobulin heavy chain constant region.

In an alternative embodiment, a method is provided for producing a soluble receptor comprised of the extracellular domains of IL-20RA and IL-20RB comprising (a) introducing into a host cell a first DNA sequence comprised of a transcriptional promoter operatively linked to a first secretory signal sequence followed downstream by and in proper reading frame the DNA that encodes the extracellular portion of IL-20RB and the DNA that encodes an immunoglobulin light chain constant region; (b) introducing into the host cell a second DNA construct comprised of a transcriptional promoter operatively linked to a second secretory signal followed downstream by and in proper reading frame a DNA sequence that encodes the extracellular portion of IL-20RA and a DNA sequence that encodes an immunoglobulin heavy chain constant region domain selected from the group consisting of $C_H1$, $C_H2$, $C_H3$ and $C_H4$; (c) growing the host cell in an appropriate growth medium under physiological conditions to allow the secretion of a dimerized heterodimeric fusion protein comprised of the extracellular domain of IL-20RA and IL-20RB; and (d) isolating the dimerized polypeptide from the host cell. In one embodiment, the second DNA sequence further encodes an immunoglobulin heavy chain hinge region wherein the hinge region is joined to the heavy chain constant region domain. In another embodiment, the second DNA sequence further encodes an immunoglobulin variable region joined upstream of and in proper reading frame with the immunoglobulin heavy chain constant region. (See U.S. Pat. No. 5,843,725.)

A polynucleotide, generally a cDNA sequence, encodes the described polypeptides herein. A cDNA sequence that encodes a polypeptide of the present invention is comprised of a series of codons, each amino acid residue of the polypeptide being encoded by a codon and each codon being comprised of three nucleotides. The amino acid residues are encoded by their respective codons as follows.

Alanine (Ala) is encoded by GCA, GCC, GCG or GCT.
Cysteine (Cys) is encoded by TGC or TGT.
Aspartic acid (Asp) is encoded by GAC or GAT.
Glutamic acid (Glu) is encoded by GAA or GAG.
Phenylalanine (Phe) is encoded by TTC or TTT.
Glycine (Gly) is encoded by GGA, GGC, GGG or GGT.
Histidine (His) is encoded by CAC or CAT.
Isoleucine (Ile) is encoded by ATA, ATC or ATT.
Lysine (Lys) is encoded by AAA, or AAG.
Leucine (Leu) is encoded by TTA, TTG, CTA, CTC, CTG or CTT.
Methionine (Met) is encoded by ATG.
Asparagine (Asn) is encoded by AAC or AAT.
Proline (Pro) is encoded by CCA, CCC, CCG or CCT.
Glutamine (Gln) is encoded by CAA or CAG.
Arginine (Arg) is encoded by AGA, AGG, CGA, CGC, CGG or CGT.
Serine (Ser) is encoded by AGC, AGT, TCA, TCC, TCG or TCT.
Threonine (Thr) is encoded by ACA, ACC, ACG or ACT.
Valine (Val) is encoded by GTA, GTC, GTG or GTT.
Tryptophan (Trp) is encoded by TGG.
Tyrosine (Tyr) is encoded by TAC or TAT.

It is to be recognized that according to the present invention, when a polynucleotide is claimed as described herein, it is understood that what is claimed are both the sense strand, the anti-sense strand, and the DNA as double-stranded having both the sense and anti-sense strand annealed together by their respective hydrogen bonds. Also claimed is the messenger RNA (mRNA) that encodes the polypeptides of the president invention, and which mRNA is encoded by the cDNA described herein. Messenger RNA (mRNA) will encode a polypeptide using the same codons as those defined herein, with the exception that each thymine nucleotide (T) is replaced by a uracil nucleotide (U).

One of ordinary skill in the art will also appreciate that different species can exhibit "preferential codon usage." In general, see, Grantham, et al., *Nuc. Acids Res.* 8:1893-1912 (1980); Haas, et al. *Curr. Biol.* 6:315-324 (1996); Wain-Hobson, et al., *Gene* 13:355-364 (1981); Grosjean and Fiers, *Gene* 18:199-209 (1982); Holm, *Nuc. Acids Res.* 14:3075-3087 (1986); Ikemura, *J. Mol. Biol.* 158:573-597 (1982). As used herein, the term "preferential codon usage" or "preferential codons" is a term of art referring to protein translation codons that are most frequently used in cells of a certain species, thus favoring one or a few representatives of the possible codons encoding each amino acid. For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Sequences containing preferential codons can be tested and optimized for expression in various species, and tested for functionality as disclosed herein.

Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722 (1991); Ellman et al., *Methods Enzymol.* 202:301 (1991; Chung et al., *Science* 259:806-809 (1993); and Chung et al., *Proc. Natl. Acad. Sci. USA* 90:10145-1019 (1993). In a second method, translation is carried out in *Xenopus* oocytes by microinjection of mutated mRNA and chemically aminoacylated suppressor tRNAs, Turcatti et al., *J. Biol. Chem.* 271:19991-19998 (1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476 (1994). Naturally occurring amino acid residues can be converted to non-naturally occurring species by in vitro chemical modification. Chemical modification can be combined with site-directed mutagenesis to further expand the range of substitutions, Wynn and Richards, *Protein Sci.* 2:395-403 (1993).

A limited number of non-conservative amino acids, amino acids that are not encoded by the genetic code, non-naturally occurring amino acids, and unnatural amino acids may be substituted for amino acid residues.

Essential amino acids in the polypeptides of the present invention can be identified according to procedures known in the art, such as site-directed mutagenesis or alanine-scanning mutagenesis, Cunningham and Wells, *Science* 244: 1081-1085 (1989); Bass et al., *Proc. Natl. Acad. Sci. USA* 88:4498-502 (1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699-708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-312 (1992); Smith et al., *J. Mol. Biol.* 224:899-904 (1992); Wlodaver et al., *FEBS Lett.* 309:59-64 (1992).

Multiple amino acid substitutions can be made and tested using known methods of mutagenesis and screening, such as those disclosed by Reidhaar-Olson and Sauer, *Science* 241: 53-57 (1988) or Bowie and Sauer, *Proc. Natl. Acad. Sci. USA* 86:2152-2156 (1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display, e.g., Lowman et al., *Biochem.* 30:10832-10837 (1991); Ladner et al., U.S. Pat. No. 5,223,409; Huse, WIPO Publication WO 92/06204) and region-directed mutagenesis, Derbyshire et al., *Gene* 46:145 (1986); Ner et al., *DNA* 7:127 (1988).

Variants of the disclosed IL-20, IL-20RA and IL-20RB DNA and polypeptide sequences can be generated through DNA shuffling as disclosed by Stemmer, *Nature* 370:389-391, (1994), Stemmer, *Proc. Natl. Acad. Sci. USA* 91:10747-10751 (1994) and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Protein Production

Polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., (Cold Spring Harbor Laboratory Press, Cold Spring Harbor, N.Y., 1989), and Ausubel et al., eds., *Current Protocols in Molecular Biology* (John Wiley and Sons, Inc., NY, 1987).

In general, a DNA sequence encoding a polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the native polypeptides, or may be derived from another secreted protein (e.g., t-PA) or synthesized de novo. The secretory signal sequence is operably linked to the DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection, Wigler et al., *Cell* 14:725 (1978), Corsaro and Pearson, *Somatic Cell Genetics* 7:603 (1981); Graham and Van der Eb, *Virology* 52:456 (1973), electroporation, Neumann et al., *EMBO J.* 1:841-845 (1982), DEAE-dextran mediated transfection (Ausubel et al., ibid., and liposome-mediated transfection, Hawley-Nelson et al., *Focus* 15:73 (1993); Ciccarone et al., *Focus* 15:80 (1993), and viral vectors, Miller and Rosman, *BioTechniques* 7:980 (1989); Wang and Finer, *Nature Med.* 2:714 (1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59 (1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47 (1987). Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding a polypeptide is inserted into the baculoviral genome in place of the AcNPV polyhedrin gene coding sequence by one of two methods. The first is the traditional method of homologous DNA recombination between wild-type AcNPV and a transfer vector containing the gene flanked by AcNPV sequences. Suitable insect cells, e.g. SF9 cells, are infected with wild-type AcNPV and transfected with a transfer vector comprising a polynucleotide operably linked to an AcNPV polyhedrin gene promoter, terminator, and flanking sequences. See, King, L. A. and Possee, R. D., *The Baculovirus Expression System: A Laboratory Guide*, (Chapman & Hall, London); O'Reilly, D. R. et al., *Baculovirus Expression Vectors: A Laboratory Manual* (Oxford University Press, New York, N.Y., 1994); and, Richardson, C. D., Ed., *Baculovirus Expression Protocols. Methods in Molecular Biology*, (Humana Press, Totowa, N.J. 1995). Natural recombination within an insect cell will result in a recombinant baculovirus that contains coding sequences driven by the polyhedrin promoter. Recombinant viral stocks are made by methods commonly used in the art.

The second method of making recombinant baculovirus utilizes a transposon-based system described by Luckow, V. A, et al., *J Virol* 67:4566 (1993). This system is sold in the Bac-to-Bac kit (Life Technologies, Rockville, Md.). This system utilizes a transfer vector, pFastBac1™ (Life Technologies) containing a Tn7 transposon to move the DNA encoding the polypeptide into a baculovirus genome maintained in *E. coli* as a large plasmid called a "bacmid." The pFastBac1™ transfer vector utilizes the AcNPV polyhedrin promoter to drive the expression of the gene of interest. However, pFastBac1™ can be modified to a considerable degree. The polyhedrin promoter can be removed and substituted with the baculovirus basic protein promoter (also known as Pcor, p6.9 or MP promoter), which is expressed earlier in the baculovirus infection, and has been shown to be advantageous for expressing secreted proteins. See, Hill-Perkins, M. S. and Possee, R. D., *J Gen Virol* 71:971 (1990); Bonning, B. C. et al., *J Gen Virol* 75:1551(1994); and, Chazenbalk, G. D., and Rapoport, B., *J Biol Chem* 270:1543 (1995). In such transfer vector constructs, a short or long version of the basic protein promoter can be used. Moreover, transfer vectors can be constructed that replace the native secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native secretory signal sequence. In addition, transfer vectors can include an in-frame fusion with DNA encoding an epitope tag at the C- or N-terminus of the expressed polypeptide, for example, a Glu-Glu epitope tag, Grussenmeyer, T. et al., *Proc Natl Acad Sci.* 82:7952 (1985). Using a technique known in the art, a transfer vector containing a recombinant gene is transformed into *E. coli*, and screened for bacmids that contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses the polypeptide is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA* (ASM Press, Washington, D.C., 1994). Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. The recombinant virus-infected cells typically produce the recombinant polypeptide at 12-72 hours post-infection and secrete it with varying efficiency into the medium. The culture is usually harvested 48 hours post-infection. Centrifugation is used to separate the cells from the medium (supernatant). The supernatant containing the polypeptide is filtered through micropore filters, usually 0.45 µm pore size. Procedures used are generally described in available laboratory manuals (King, L. A. and Possee, R. D., ibid., O'Reilly, D. R. et al., ibid.; Richardson, C. D., ibid.). Subsequent purification of the polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S.*

*cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., J. Gen. Microbiol. 132:3459 (1986) and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (τ) of from 1 to 40 milliseconds, most preferably about 20 milliseconds.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art; see, e.g., Sambrook et al., ibid.). When expressing a polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient, which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Protein Isolation

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant polypeptides (or chimeric polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods* (Pharmacia LKB Biotechnology, Uppsala, Sweden, 1988).

Polypeptides can be isolated by exploitation of their properties. For example, immobilized metal ion adsorption (IMAC) chromatography can be used to purify histidine-rich proteins, including those comprising polyhistidine tags. Briefly, a gel is first charged with divalent metal ions to form a chelate, Sulkowski, *Trends in Biochem*. 3:1 (1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography. A protein fused to the Fc portion of an immunoglobulin can be purified using a 'Protein A column'. *Methods in Enzymol.*, Vol. 182, "Guide to Protein Purification", M. Deutscher, (ed.), page 529-539 (Acad. Press, San Diego, 1990). Within additional embodiments of the invention, a fusion of the polypeptide of interest and an affinity tag (e.g., maltose-binding protein, an immunoglobulin domain) may be constructed to facilitate purification.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

A variety of assays known to those skilled in the art can be utilized to detect antibodies that bind to protein or peptide. Exemplary assays are described in detail in *Antibodies: A Laboratory Manual*, Harlow and Lane (Eds.) (Cold Spring Harbor Laboratory Press, 1988). Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay.

The soluble receptors of the present invention can be used to down-regulate IL-20, which has been shown to be involved in a number of inflammatory processes. Specifically, IL-20 has been shown to up-regulate IL-8. Inflammatory diseases in which IL-8 plays a significant role, and for which a decrease in IL-8 would be beneficial are, adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease. Thus, the soluble receptor to IL-20 of the present invention can be administered to a patient to treat these diseases.

Biology of IL-20, its Receptor and its Role in Psoriasis

Two orphan class II cytokine receptors, both of which are expressed in skin, were identified as IL-20 receptor subunits. Both IL-20 receptor subunits are required for ligand binding, distinguishing their role from that of subunits in the four other known class II cytokine receptors. IL-20RA and IL-20RB are also coexpressed in a number of human tissues besides skin, including ovary, adrenal gland, testis, salivary gland, muscle, lung, kidney, heart and to a lesser degree the small intestine suggesting additional target tissues for IL-20 action. We conclude that the IL-20 heterodimeric receptor is structurally similar to other class II cytokine receptors and is expressed in skin where we have demonstrated activity of the IL-20 ligand.

Two lines of evidence indicate that a role IL-20 and its receptor are involved in psoriasis. This multigenic skin disease is characterized by increased keratinocyte proliferation, altered keratinocyte differentiation, and infiltration of immune cells into the skin. The first line of evidence for a role of IL-20 in psoriasis is that the observed hyperkeratosis and thickened epidermis in the transgenic mice that resemble human psoriatic abnormalities. Decreased numbers of tonofilaments, thought to be related to defective keratinization, are a striking feature of human psoriasis. Intramitochondrial inclusions have been found in both chemically induced and naturally occurring hyperplastic skin conditions in mice. The cause of the inclusions and their effects on mitochondrial function, if any, are unknown. We conclude that IL-20 transgenic mice exhibit many of the characteristics observed in human psoriasis.

A second line of evidence that implicates the IL-20 receptor in psoriasis is that both IL-20RA and IL-20RB mRNA are markedly upregulated in human psoriatic skin compared to normal skin. Both IL-20 receptor subunits are expressed in keratinocytes throughout the epidermis and are also expressed in a subset of immune and endothelial cells. We propose that increased expression of an activated IL-20 receptor may alter the interactions between endothelial cells, immune cells and keratinocytes, leading to dysregulation of keratinocyte proliferation and differentiation.

A crucial step in understanding the function of a novel cytokine is the identification and characterization of its cognate receptor. We have successfully used a structure-based approach to isolate a novel interleukin that ultimately led to the isolation of its receptor. IL-20 stimulates signal transduction in the human keratinocyte HaCaT cell line, supporting a direct action of this novel ligand in skin. In addition, IL-1β, EGF and TNF-α, proteins known to be active in keratinocytes and to be involved with proliferative and pro-inflammatory signals in skin, enhance the response to IL-20. In both HaCaT and BHK cells expressing the IL-20 receptor, IL-20 signals through STAT3. Thus, IL-20 binds its receptor on keratinocytes and stimulates a STAT3-containing signal transduction pathway.

Use of Antagonist to IL-20 to Treat Psoriasis

As indicated in the discussion above and the examples below, IL-20 is involved in the pathology of psoriasis. Thus, the soluble receptors of the present invention can be administered to an individual to down-regulate IL-20 and thus treat psoriasis.

Psoriasis is one of the most common dermatologic diseases, affecting up to 1 to 2 percent of the world's population. It is a chronic inflammatory skin disorder characterized by erythematous, sharply demarcated papules and rounded plaques, covered by silvery micaceous scale. The skin lesions of psoriasis are variably pruritic. Traumatized areas often develop lesions of psoriasis. Additionally, other external factors may exacerbate psoriasis including infections, stress, and medications, e.g. lithium, beta blockers, and anti-malarials.

The most common variety of psoriasis is called plaque type. Patients with plaque-type psoriasis will have stable, slowly growing plaques, which remain basically unchanged for long periods of time. The most common areas for plaque psoriasis to occur are the elbows knees, gluteal cleft, and the scalp. Involvement tends to be symmetrical. Inverse psoriasis affects the intertriginous regions including the axilla, groin, submammary region, and navel, and it also tends to affect the scalp, palms, and soles. The individual lesions are sharply demarcated plaques but may be moist due to their location. Plaque-type psoriasis generally develops slowly and runs an indolent course. It rarely spontaneously remits.

Eruptive psoriasis (guttate psoriasis) is most common in children and young adults. It develops acutely in individuals without psoriasis or in those with chronic plaque psoriasis. Patients present with many small erythematous, scaling papules, frequently after upper respiratory tract infection with beta-hemolytic streptococci. Patients with psoriasis may also develop pustular lesions. These may be localized to the palms and soles or may be generalized and associated with fever, malaise, diarrhea, and arthralgias.

About half of all patients with psoriasis have fingernail involvement, appearing as punctate pitting, nail thickening or subungual hyperkeratosis. About 5 to 10 percent of patients with psoriasis have associated joint complaints, and these are most often found in patients with fingernail involvement. Although some have the coincident occurrence of classic Although some have the coincident occurrence of classic rheumatoid arthritis, many have joint disease that falls into one of five type associated with psoriasis: (1) disease limited to a single or a few small joints (70 percent of cases); (2) a seronegative rheumatoid arthritis-like disease; (3) involvement of the distal interphalangeal joints; (4) severe destructive arthritis with the development of "arthritis mutilans"; and (5) disease limited to the spine.

Psoriasis can be treated by administering antagonists to IL-20. The preferred antagonists are either a soluble receptor to IL-20 or antibodies, antibody fragments or single chain antibodies that bind to either the IL-20 receptor or to IL-20. The antagonists to IL-20 can be administered alone or in combination with other established therapies such as lubricants, keratolytics, topical corticosteroids, topical vitamin D derivatives, anthralin, systemic antimetabolites such as methotrexate, psoralen-ultraviolet-light therapy (PUVA), etretinate, isotretinoin, cyclosporine, and the topical vitamin D3 derivative calcipotriol. The antagonists, in particularly the soluble receptor or the antibodies that bind to IL-20 or the IL-20 receptor can be administered to individual subcutaneously, intravenously, or transdermally using a cream or transdermal patch that contains the antagonist of IL-20. If administered subcutaneously, the antagonist can be injected into one or more psoriatic plaques. If administered transdermally, the antagonists can be administered directly on the plaques using a cream containing the antagonist to IL-20.

Use of Antagonists to IL-20 to Treat Inflammatory Conditions of the Lung.

The soluble receptor of IL-20 of the present invention can be administered to a person who has asthma, bronchitis or cystic fibrosis or other inflammatory lung disease to treat the disease. The antagonists can be administered by any suitable method including intravenous, subcutaneous, bronchial lavage, and the use of inhalant containing an antagonist to IL-20.

Administration of the IL-20 Soluble Receptor

The quantities of the IL-20 soluble necessary for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in vivo administration of these reagents. Animal testing of effective doses for treatment of particular disorders will provide further predictive indication of human dosage. Methods for administration include oral, intravenous, peritoneal, intramuscular, transdermal or administration into the lung or trachea in spray form by means or a nebulizer or atomizer. Pharmaceutically acceptable carriers will include water, saline, buffers to name just a few. Dosage ranges would ordinarily be expected from 1 μg to 1000 μg per kilogram of body weight per day. A dosage for an average adult of the IL-20 soluble receptor would be about 25 mg given twice weekly as a subcutaneous injection. Injections could be given at the site of psoriatic lesions for the treatment of psoriasis. For subcutaneous or intravenous administration of the antagonist to IL-20, the antibody or soluble receptor can be in phosphate buffered saline. Also in skin diseases such as psoriasis, the antagonist to IL-20 can be administered via an ointment or transdermal patch. The doses by may be higher or lower as can be determined by a medical doctor with ordinary skill in the art. For a complete discussion of drug formulations and dosage ranges see *Remington's Pharmaceutical Sciences,* $18^{th}$ Ed., (Mack Publishing Co., Easton, Pa., 1996), and *Goodman and Gilman's: The Pharmacological Bases of Therapeutics,* $9^{th}$ Ed. (Pergamon Press 1996).

The invention is further illustrated by the following non-limiting examples.

EXAMPLE 1

Up-Regulation of IL-8 by IL-20

Methods:

Normal Human Epidermal neonatal keratinocytes (NHEK) (from Clonetics) at passage 2 were plated and grown to confluency in 12 well tissue culture plates. KGM (Keratinocyte growth media) was purchased from Clonetics. When cells reached confluency, they were washed with KGM media minus growth factors=KBM (keratinocyte basal media). Cells were serum starved in KBM for 72 hours prior to the addition of test compounds. Thrombin at 1 I.U./mL and trypsin at 25 nM were used as positive controls. One mL of media/well was added. KBM only was used as the negative control.

IL-20 was made up in KBM media and added at varying concentrations, from 2.5 µg/ml down to 618 ng/mL in a first experiment and from 2.5 µg/mL down to 3 ng/mL in a second experiment.

Cells were incubated at 37° C., 5% $CO_2$ for 48 hours. Supernatants were removed and frozen at −80° C. for several days prior to assaying for IL-8 and GM-CSF levels. Human IL-8 Immunoassay kit # D8050 (Rand D Systems, Inc.) and human GM-CSF Immunoassay kit # HSGMO (Rand D Systems, Inc.) were used to determine cytokine production following manufacturer's instructions.

Results

The results indicated that the expression of IL-8 and GM-CSF were induced by IL-20.

EXAMPLE 2

Cloning of IL-20RB

Cloning of IL-20RB Coding Region

Two PCR primers were designed based on the sequence from International Patent Application No. PCT/US99/03735 (publication no. WO 99/46379) filed on Mar. 8, 1999. SEQ ID NO: 16 contains the ATG (Met1) codon with an EcoRI restriction site, SEQ ID NO: 17 contains the stop codon (TAG) with an XhoI restriction site. The PCR amplification was carried out using a human keratinocyte (HaCaT) cDNA library DNA as a template and SEQ ID NO: 16 and SEQ ID NO: 17 as primers. The PCR reaction was performed as follows: incubation at 94° C. for 1 min followed by 30 cycles of 94° C. for 30 sec and 68° C. for 2 min, after additional 68° C. for 4 min, the reaction was stored at 4° C. The PCR products were run on 1% Agarose gel, and a 1 kb DNA band was observed. The PCR products were cut from the gel and the DNA was purified using a QIAquick Gel Extraction Kit (Qiagen). The purified DNA was digested with EcoRI and XhoI, and cloned into a pZP vector that was called pZP7N. A pZP plasmid is a mammalian expression vector containing an expression cassette having the mouse metallothionein-1 promoter, human tPA leader peptide, multiple restriction sites for insertion of coding sequences, a Glu-Glu tag, and a human growth hormone terminator. The plasmid also has an E. coli origin of replication, a mammalian selectable marker expression unit having an SV40 promoter, an enhancer and an origin of replication, as well as a DHFR gene, and the SV40 terminator. Several IL-20RB-pZP7N clones were sequenced. They all contain three non-conservative mutations compared with the sequence of IL-20RB in PCT/US99/03735: (sequence IL-20RB-pZP7N), 146 Pro (CCC)—Thr (ACC), 148 His (CAT)—Asp (GAT), and 171 Thr (ACG)—Arg (AGG).

To verify the three substitutions in IL-20RB-pZP7N clone, PCR amplification was carried out using three difference cDNA sources—fetal skin marathon cDNA, HaCaT cDNA library DNA, and prostate smooth muscle cDNA library DNA—as templates. The PCR products were gel purified and sequenced. The sequence of each of the three PCR products was consistent with that of the IL-20RB-pZP7N clone. IL-20RB is SEQ ID NO: 13 and 14, and the mature extracellular domain is SEQ ID NO: 15.

EXAMPLE 3

Binding of IL-20 to IL-20RB/IL-20RA Heterodimer

A cell-based binding assay was used to verify IL-20 binds to IL-20RA-IL-20RB heterodimer.

Expression vectors containing known and orphan Class II cytokine receptors (including IL-20RA and IL-20RB) were transiently transfected into COS cells in various combinations, which were then assayed for their ability to bind biotin-labeled IL-20 protein. The results show IL-20RB-IL-20RA heterodimer is a receptor for IL-20. The procedure used is described below.

The COS cell transfection was performed in a 12-well tissue culture plate as follows: 0.5 µg DNA was mixed with medium containing 5 µl lipofectamine in 92 µl serum free Dulbecco's modified Eagle's medium (DMEM) (55 mg sodium pyruvate, 146 mg L-glutamine, 5 mg transferrin, 2.5 mg insulin, 1 µg selenium and 5 mg fetuin in 500 ml DMEM), incubated at room temperature for 30 minutes and then added to 400 µl serum free DMEM media. This 500 µl mixture was then added to $1.5 \times 10^5$ COS cells/well and incubated for 5 hours at 37° C. 500 µl 20% fetal bovine serum (FBS) DMEM media was added and incubated overnight.

The assay, a modification of the "secretion trap" (Davis, S., et al., Cell 87: 1161-1169 (1996), was performed as follows: cells were rinsed with PBS/1% bovine serum albumin (BSA) and blocked for 1 hour with TNB (0.1 M Tris-HCl, 0.15 M NaCl and 0.5% Blocking Reagent (NEN Renaissance TSA-Direct Kit Cat# NEL701) in water). This was followed by a one-hour incubation with 3 µg/ml biotinylated IL-20 protein in TNB. Cells were washed with PBS/1% BSA and incubated for another hour with 1:300 diluted streptavidin-HRP (NEN kit) in TNB. Following another wash, cells were fixed for 15 minutes with 1.8% Formaldehyde in phosphate-buffered saline (PBS). Cells were then washed with TNT (0.1 M Tris-HCL, 0.15 M NaCl, and 0.05% Tween-20 in water). Positive binding signals were detected following a five-minute incubation with fluorescein tyramide reagent diluted 1:50 in dilution buffer (NEN kit). Cells were washed with TNT, preserved with Vectashield Mounting Media (Vector Labs) diluted 1:5 in TNT, and visualized using an FITC filter on an inverted fluorescent microscope.

EXAMPLE 4

Up-Regulation of Inflammatory Cytokines by IL-20

Cell Treatment

The human keratinocyte cell line, HaCaT was grown at 37° C. to several days post-confluence in T-75 tissue culture flasks. At this point, normal growth media (DMEM+10% FBS) was removed and replaced with serum-free media. Cells were then incubated for two days at 37° C. DMEM was then removed and four flasks of cells per treatment were treated with one of each of the following conditions for four hours at 37° C.: recombinant human (rh) IL-1 alpha at 5 ng/mL, rh IL-1 alpha at 20 ng/mL, rh IL-1 alpha at 5 ng/mL+IL-20 at 1 µg/mL, IL-20 at 1 µg/mL, or rh IL-10 at 10 ng/mL.

RNA Isolation

Following cytokine treatment, media was removed and cells were lysed using a guanidium thiocyanate solution. Total RNA was isolated from the cell lysate by an overnight spin on a cesium chloride gradient. The following day, the RNA pellet was resuspended in a TE/SDS solution and ethanol precipitated. RNA was then quantitated using a spectrophotometer, followed by a DNase treatment as per Section V.B. of Clontech's Atlas™ cDNA Expression Arrays User Manual (version PT3140-1/PR9×390, published Nov. 5, 1999). Quality of RNA samples was verified by purity calculations based on spec readings, and by visualization on agarose gel. Genomic contamination of the RNA samples was ruled out by PCR analysis of the beta-actin gene.

Probe Synthesis

Clontech's protocols for polyA+ enrichment, probe synthesis and hybridization to Atlas™ arrays were followed (see above, plus Atlas™ Pure Total RNA Labeling System User Manual, PT3231-1/PR96157, published Jun. 22, 1999). Briefly, polyA+ RNA was isolated from 50 mg of total RNA using streptavidin coated magnetic beads (by Clontech, Paolo Alto, Calif.) and a magnetic particle separator. PolyA+ RNA was then labeled with $^{alpha32}$P-dATP via RT-PCR. Clontech CDS primers specific to the 268 genes on the Atlas™ human cytokine/receptor array (Cat. #7744-1) were used in the reaction. Labeled probe was isolated using column chromatography and counted in scintillation fluid.

Array Membrane Hybridization

Atlas™ arrays were pre-hybridized with Clontech ExpressHyb plus 100 mg/mL heat denatured salmon sperm DNA for at least thirty minutes at 68° C. with continuous agitation. Membranes were then hybridized with $1.9 \times 10^6$ CPM/mL (a total of $1.14 \times 10^7$ CPM) overnight at 68° C. with continuous agitation. The following day, membranes were washed for thirty minutes×4 in 2×SSC, 1% SDS at 68° C., plus for thirty minutes×1 in 0.1×SSC, 0.5% SDS at 68° C., followed by one final room temperature wash for five minutes in 2×SSC. Array membranes were then placed in Kodak plastic pouches sealed and exposed to a phosphor imager screen overnight at room temperature. The next day, phosphor screens were scanned on a phosphor imager and analyzed using Clontech's AtlasImage™ 1.0 software.

Results

Genes Up-Regulated by IL-20
1. Tumor necrosis factor (TNF) was up-regulated 1.9-2.4 fold by IL-20.
2. Placental growth factors 1 & 2 (PLGF) were up-regulated 1.9-2.0 fold by IL-20.
3. Coagulating factor II receptor was up-regulated 2.0-2.5 fold by IL-20.
4. Calcitonin receptor was up-regulated 2.2-2.3 fold by IL-20.
5. TNF-inducible hyaluronate-binding protein TSG-6 was up-regulated 2.1-2.2 fold by IL-20.
6. Vascular endothelial growth factor (VEGF) receptor-1 precursor, tyrosine-protein kinase receptor (FLT-1) (SFLT) was up-regulated 2.1-2.7 fold by IL-20.
7. MRP-8 (calcium binding protein in macrophages MIF-related) was up-regulated 2.9-4.1 fold by IL-20.
8. MRP-14 (calcium binding protein in macrophages MIF-related) was up-regulated 3.0-3.8 fold by IL-20.
9. Relaxin H2 was up-regulated 3.14 fold by IL-20.
10. Transforming growth factor beta (TGFβ) receptor III 300 kDa was up-regulated 2.4-3.6 fold by IL-20.

Genes Showing Synergy with IL-20+IL-1 Treatment
1. Bone morphogenic protein 2a was up-regulated 1.8 fold with IL-20 treatment alone, 2.5 fold with IL-1 treatment alone, and 8.2 fold with both IL-20 and IL-1 treatment together.
2. MRP-8 was up-regulated 2.9 fold with IL-20 treatment alone, 10.7 fold with IL-1 treatment alone and 18.0 fold with both IL-20 and IL-1 treatment together.
3. Erythroid differentiation protein (EDF) was up-regulated 1.9 fold with IL-20 treatment alone, 9.7 fold with IL-1 treatment alone and 19.0 fold with both IL-20 and IL-1 treatment together.
4. MRP-14 (calcium binding protein in macrophages, MIF related) was up-regulated 3.0 fold with IL-20 treatment alone, 12.2 fold with IL-1 treatment alone and 20.3 fold with both IL-20 and IL-1 treatment together.
5. Heparin-binding EGF-like growth factor was up-regulated 2.0 fold with IL-20 treatment alone, 14 fold with IL-1 treatment alone and 25.0 fold with both IL-20 and IL-1 treatment together.
6. Beta-thromboglobulin-like protein was up-regulated 1.5 fold with IL-20 treatment alone, 15 fold with IL-1 treatment alone and 27 fold with both IL-20 and IL-1 treatment together.
7. Brain-derived neurotrophic factor (BDNF) was up-regulated 1.7 fold with IL-20 treatment alone, 25 fold with IL-1 treatment alone and 48 fold with both IL-20 and IL-1 treatment together.
8. Monocyte chemotactic and activating factor MCAF was up-regulated 1.3 fold with IL-20 treatment alone, 32 fold with IL-1 treatment alone and 56 fold with both IL-20 and IL-1 treatment together.

EXAMPLE 5

IL-20RA/RB Receptor-Ig Fusion Heterotetramer

The expression vector pEZE3 was used to express the recombinant IL-20 receptor-Ig fusion protein. The plasmid pEZE3 is derived from pDC312. pDC312 was obtained through license from Immunex Corporation. The plasmids pDC312 and pEZE3 contain an EASE segment as described in WO 97/25420. The presence of the EASE segment in an expression vector can improve expression of recombinant proteins two to eight fold in stable cell pools.

The plasmid pEZE3 is a tricistronic expression vector that may be used to express up to three different proteins in mammalian cells, preferably Chinese Hamster Ovary (CHO) cells. The pEZE3 expression unit contains the cytomegalovirus (CMV) enhancer/promoter, the adenovirus tripartite leader sequence, a multiple cloning site for insertion of the coding region for the first recombinant protein, the poliovirus type 2 internal ribosome entry site, a second multiple cloning site for insertion of the coding region for the second recombinant protein, an encephalomyocarditis virus internal ribosome entry site, a coding segment for mouse dihydrofolate reductase, and the SV40 transcription terminator. In addition, pEZE3 contains an *E. coli* origin of replication and the bacterial beta lactamase gene.

The IL-20 receptor-Ig fusion protein is a disulfide linked heterotetramer consisting of two chains of the extracellular domain of the human IL-20RB fused to the wild type human immunoglobulin kappa light chain constant region and two chains of the human IL-20RA protein extracellular domain fused to a mutated human immunoglobulin gamma 1 constant region. The human immunoglobulin gamma 1 constant region contains amino acid substitutions to reduce FcγRI binding and C1q complement fixation.

The human IL-20RB extracellular domain human immunoglobulin kappa light chain constant region fusion construct was generated by overlap PCR. The IL-20RB coding segment consists of amino acids 1 to 230. The template used for the PCR amplification of the IL-20R segment was generated IL-20RB human kappa light chain constant region expression construct as described below in Example 12. Oligonucleotide primers SEQ ID NO: 24 and SEQ ID NO: 25 were used to amplify the IL-20RB segment. The entire wild type human immunoglobulin kappa light chain constant region was used. The template used for the PCR amplification of the wild type human immunoglobulin kappa light chain constant region segment was generated IL-20RB human kappa light chain constant region expression construct as described in Example 12. Oligonucleotide primers SEQ ID NO: 26 and SEQ ID NO: 27 were used to amplify the wild type human immunoglobulin kappa light chain constant region. The two protein coding domains were linked by overlap PCR using oligonucleotides SEQ ID NO: 24 and SEQ ID NO: 27. A $(Gly_4Ser)_3$ (SEQ ID NO: 72) peptide linker was inserted between the two protein domains. The $(Gly_4Ser)_3$ peptide linker was encoded on the PCR primers SEQ ID NO: 26 and SEQ ID NO:25. The resultant IL-20RB extracellular domain/kappa light chain constant region fusion construct is shown by SEQ ID NOs: 20 and 21. The predicted mature polypeptide, minus the signal sequence, is SEQ ID NO: 60. The portion of the extracellular domain of IL-20RB that was actually used was comprised of the amino acid sequence of SEQ ID NO: 61. N-terminal sequencing resulted in the predicted amino acid sequence.

The human IL-20RA extracellular domain human immunoglobulin gamma 1 heavy chain constant region fusion construct was generated by overlap PCR of four separate DNA fragments, each generated by separate PCR amplification reactions. The first fragment contained an optimized tPA (tissue plasminogen activator) signal sequence. The tPA signal sequence was amplified using oligonucleotide primers SEQ ID NO: 28 and SEQ ID NO: 29 using an in-house previously generated expression vector as the template. The second fragment contained the IL-20RA extracellular domain-coding region consisting of amino acids 30 to 243 of SEQ ID NO: 11. Oligonucleotide primers SEQ ID NO: 30 and SEQ ID NO: 31 were used to amplify this IL-20RA segment using a previously generated clone of IL-20RA as the template.

The human gamma 1 heavy chain constant region was generated from 2 segments. The first segment containing the $C_H1$ domain was amplified using oligonucleotide primers SEQ ID NO: 32 and SEQ ID NO: 33 using a clone of the wild type human gamma 1 heavy chain constant region as the template. The second segment containing the remaining hinge, $C_H2$, and $C_H3$ domains of the human immunoglobulin gamma 1 heavy chain constant region was generated by PCR amplification using oligonucleotide primers SEQ ID NO: 34 and SEQ ID NO: 35. The template used for this PCR amplification was from a previously generated human gamma 1 Fc construct that contained codons for amino acid substitutions to reduce FcγRI binding and C1q complement fixation as described in Example 12.

The four protein coding domains were linked by overlap PCR using oligonucleotides SEQ ID NO: 28 and SEQ ID NO: 35. A $(Gly_4Ser)_3$ peptide linker was inserted between the IL-20RA and CH1 protein domains. The $(Gly_4Ser)_3$ peptide linker was encoded on the PCR primers SEQ ID NO: 32 and SEQ ID NO: 31. The IL-20RA extracellular domain/domain human immunoglobulin gamma 1 heavy constant region fusion protein and DNA sequence are shown in SEQ ID NOs: 22 and 23. The predicted mature polypeptide sequence, minus the signal sequence, is SEQ ID NO: 62. The portion of extracellular domain of IL-20RA that was actually used was comprised of SEQ ID NO: 63.

The IL-20RB extracellular domain human immunoglobulin kappa light chain constant region fusion coding segment was cloned into the second MCS while the human IL-20RA extracellular domain human immunoglobulin gamma 1 heavy chain constant region fusion coding segment was cloned into the first MCS of pEZE3. The plasmid was used to transfect CHO cells. The cells were selected in medium without hypoxanthine or thymidine and the transgene was amplified using methotrexate. The presence of protein was assayed by Western blotting using anti human gamma 1 heavy chain constant region and anti human kappa light chain antibodies. N-terminal sequencing revealed that the optimized tPA leader was not completely cleaved. The observed mass indicated that the first residue of the polypeptide sequence to be pyroglutamic acid, and the N-terminal sequence appears to be pyroEEIHAELRRFRRVPCVSGG (SEQ ID NO: 64), the underlined portion being remnants of the tPA leader.

EXAMPLE 6

IL-20 Transgenic Phenotype

Both human and mouse IL-20 were overexpressed in transgenic mice using a variety of promoters. The liver-specific mouse albumin promoter, directing expression of human IL-20, was used initially in an attempt to achieve circulating levels of protein. Subsequent studies were conducted using the keratin 14 (K14) promoter, which primarily targets expression to the epidermis and other stratified squamous epithelia; the mouse metallothionein-1 promoter, which gives a broad expression pattern; and the E□LCK promoter, which drives expression in cells of the lymphoid lineage. Similar results were obtained in all four cases, possibly because these promoters all give rise to circulating levels of IL-20.

In all cases, transgenic pups expressing the IL-20 transgene were smaller than non-transgenic littermates, had a shiny appearance with tight, wrinkled skin and died within the first few days after birth. Pups had milk in their stomachs indicating that they were able to suckle. These mice had swollen extremities, tail, nostril and mouth regions and had difficulty moving. In addition, the mice were frail, lacked visible adipose tissue and had delayed ear and toe development. Low expression levels in liver (less than 100 mRNA molecules/cell) were sufficient for both the neonatal lethality and skin abnormalities. Transgenic mice without a visible phenotype either did not express the transgene, did not express it at detectable levels, or were mosaic.

Histologic analysis of the skin of the IL-20 transgenic mice showed a thickened epidermis, hyperkeratosis and a compact stratum corneum compared to non-transgenic littermates. Serocellular crusts (scabs) were observed occasionally. Electron microscopic (EM) analysis of skin from transgenic mice showed intramitochondrial lipid inclusions, mottled keratohyaline granules, and relatively few tonofilaments similar to that observed in human psoriatic skin and in mouse skin disease models. In addition, many of the transgenic mice had apoptotic thymic lymphocytes. No other abnormalities were detected by histopathological analysis. These histological and EM results support and extend the observed gross skin alterations.

EXAMPLE 7

Specificity and Affinity of IL-20 for its Receptor

The specificity and affinity of IL-20 for its receptor was determined using BHK cells stably transfected with IL-20RA, IL-20RB or both receptor subunits. Binding assays using radiolabeled ligand demonstrated that IL-20 bound to BHK transfectants expressing both IL-20RA and IL-20RB but not to untransfected cells nor to transfectants expressing either receptor subunit alone. Binding of $^{125}$I-labeled IL-20 was eliminated in the presence of 100-fold excess of unlabeled IL-20 but not with 100-fold excess of the unrelated cytokine, IL-21. The binding affinity (kD) of IL-20 to the IL-20RA/IL-20RB heterodimeric receptor was determined to be approximately 1.5 nM.

EXAMPLE 8

IL-20 Receptor Activation

To determine if IL-20 binding leads to receptor activation, the factor-dependent pre-B cell line BaF3 was co-transfected with IL-20RA and IL-20RB and treated with IL-20 at various concentrations. IL-20 stimulated proliferation in a dose-dependent manner and gave a detectable signal at 1.1 pM, with a half maximal response at 3.4 pM. We note that the IL-20 concentration for the half maximal proliferative response in BaF3 cells is 1000× lower than that for half maximal binding affinity in BHK cells. Possible explanations for this large difference include the use of different cell lines, different receptor expression levels and different assay outputs. IL-20 also stimulated signal transduction in the biologically relevant human keratinocyte cell line HaCaT, which naturally expresses IL-20RA and IL-20RB. Therefore, IL-20 binds and activates the heterodimeric IL-20RA/IL-20RB receptor at concentrations expected for a cytokine. While the negative controls containing untransfected BaF3

EXAMPLE 9

Expression Analysis of IL-20RA and IL-20RB

RT-PCR analysis was performed on a variety of human tissues to determine the expression pattern of IL-20RA and IL-20RB. Both receptor subunits are most highly expressed in skin and testis. The significant result is that IL-20RA and IL-20RB are both expressed in skin, where they have been shown to mediate the IL-20-induced response. Both IL-20RA and IL-20RB are also both expressed in monocytes, lung, ovary, muscle, testis, adrenal gland, heart, salivary gland and placenta. IL-20RA is also in brain, kidney, liver, colon, small intestine, stomach, thyroid, pancreas, uterus and prostate while IL-20RB is not.

EXAMPLE 10

IL-20RA and IL-20RB mRNA are Up-Regulated in Psoriasis

In situ hybridization was used to determine whether IL-20 receptor expression is altered in psoriasis. Skin samples from four psoriasis patients and three unaffected patients were assayed with probes specific for the two-receptor subunit mRNAs. All four psoriatic skin samples had high levels of IL-20RA and IL-20RB mRNA in keratinocytes whereas normal skin samples did not have detectable levels of either receptor subunit mRNA. Positive signals in psoriatic skin were also observed in mononuclear immune cells and in endothelial cells in a subset of vessels. Therefore, both IL-20RA and IL-20RB are expressed in keratinocytes, immune cells and endothelial cells, the major cell types thought to interact in psoriasis.

EXAMPLE 11

Cloning of Mouse IL-20RA

A cross-species hybridization probe was generated which contained the full-length cDNA fragment encoding human IL-20RA. A Southern blot of mouse genomic DNA and Northern blots of mouse RNA were performed to demonstrate that the human IL-20RA cDNA could specifically hybridize to mouse sequences. The Northern blot results indicated that mouse IL-20RA RNA was present in mouse embryo day 15 and 17 as well as heart, brain, lung, liver, kidney, testes, spleen, thymus, liver, stomach, and small intestine.

The human IL-20RA full length DNA hybridization probe was used to screen a mouse genomic library. The library, which was obtained from Clontech (Palo Alto, Calif.), was generated from an MboI partial digest of mouse genomic DNA and cloned into the BamHI site of Lambda bacteriophage EMBL3 SP6/T7. Positive bacteriophage was plaque purified and bacteriophage DNA was prepared using Promega's Wizard Lambda Preps DNA Purification System. Two genomic restriction enzyme fragments, a 5.7 kb EcoRI fragment and an 8.0 kb Sac fragment, were generated from the positive bacteriophage and subcloned into pBluescript. DNA sequence analysis revealed the presence of 3 exons from the mouse ortholog to human IL-20RA.

PCR primers from the 5' UTR, SEQ ID NO: 40, and 3' UTR, SEQ ID NO: 41, were designed to generate a full-length mouse IL-20RA sequence by PCR amplification. Mouse embryo 15 day plus 17 day cDNA was used as the template for the PCR amplification. PCR products were subcloned and sequenced for confirmation. The mouse sequences are SEQ ID NOs: 36 and 37. The mature extracellular domain is comprised of SEQ ID NO: 38.

EXAMPLE 12

Construction of an IL-20 Receptor Heterotetramer

A vector expressing a secreted hIL-20RA/hIL-20B heterodimer was constructed. In this construct, the extracellular domain of hIL-20RA was fused to the heavy chain of IgG gamma 1 (IgGγ1), while the extracellular portion of IL-20RB was fused to human kappa light chain (human κ light chain).

Construction of IgG Gamma 1 and Human κ Light Fusion Vectors

The heavy chain of IgGγ1 was cloned into the Zem229R mammalian expression vector (ATCC deposit No. 69447) such that any extracellular portion of a receptor having a 5' EcoRI and 3' NheI site can be cloned in, resulting in an N-terminal extracellular domain-C-terminal IgGγ1 fusion. The IgGγ1 fragment used in this construct was made by using PCR to isolate the IgGγ1 sequence from a Clontech human fetal liver cDNA library as template. A PCR reaction using oligos SEQ ID NO: 42 and SEQ ID NO: 43 was run as follows: 40 cycles of 94° for 60 sec., 53° C. for 60 sec., and 72° for 120 sec.; and 72° C. for 7 minutes. PCR products were separated by agarose gel electrophoresis and purified using a QiaQuick™ (Qiagen Inc., Valencia, Calif.) gel extraction kit. The isolated, 990 bp, DNA fragment was digested with MluI and EcoRI (Boerhinger-Mannheim), extracted with QiaQuick™ gel extraction kit and ligated with oligos SEQ ID NO: 44 and SEQ ID NO: 45, which comprise an MluI/EcoRI linker, into Zem229R previously digested with MluI and EcoRI using standard molecular biology techniques disclosed herein. This generic cloning vector was called Vector#76 hIgGgamma1 w/Ch1 #786 Zem229R (Vector #76). The polynucleotide sequence of the extracellular domain of hIL-20RA fused to the heavy chain of IgG gamma 1 is show in SEQ ID NO: 52 and the corresponding polypeptide sequence shown in SEQ ID NO: 53, the mature polypeptide, minus the signal sequence being comprised of SEQ ID NO: 54. The portion of the extracellular domain of IL-20RA used was comprised of SEQ ID NO: 55.

The human κ light chain was cloned in the Zem228R mammalian expression vector (ATCC deposit No. 69446) such that any extracellular portion of a receptor having a 5' EcoRI site and a 3' KpnI site can be cloned in, resulting in an N-terminal extracellular domain-C-terminal human κ light chain fusion. The human κ light chain fragment used in this construct was made by using PCR to isolate the human κ light chain sequence from the same Clontech hFetal Liver cDNA library used above. A PCR reaction was run using oligos SEQ ID NO: 46 and SEQ ID NO: 47. PCR products were separated by agarose gel electrophoresis and purified using a QiaQuick™ (Qiagen) gel extraction kit. The isolated, 315 bp, DNA fragment was digested with MluI and EcoRI (Boerhinger-Mannheim), extracted with QiaQuick™ gel extraction kit and ligated with the MluI/EcoRI linker described above, into Zem228R previously digested with MluI and EcoRI using standard molecular biology techniques disclosed herein. This generic cloning vector was called Vector #77 hKlight #774 Zem228R (Vector #77). The polynucleotide sequence of the extracellular portion of IL-20RB fused to human kappa light chain is shown in SEQ ID NO: 56 and the corresponding polypeptide sequence shown in SEQ ID NO: 57, the mature polypeptide, minus the signal sequence, is comprised of SEQ ID NO: 58. The portion of the extracellular domain of IL-20RB actually used was comprised of SEQ ID NO: 59.

Insertion of hIL-20RA and IL-20RB Extracellular Domains into Fusion Vector Constructs Using the construction vectors above, a construct having human IL-20RA fused to IgGγ1 was made. This construction was done by using PCR to obtain human IL-20RA receptor from hIL-20RA/IgG Vector #102 with oligos SEQ ID NO: 48 and SEQ ID NO: 49 under conditions described as follows: 30 cycles of 94° C. for 60 sec., 57° C. for 60 sec., and 72° C. for 120 sec.; and 72° C. for 7 min. The resulting PCR product was digested with EcoRI and NheI, gel purified, as described herein, and ligated into a previously EcoRI and NheI digested and band-purified Vector #76 (above). The resulting vector was sequenced to confirm that the human IL-20Rα/IgG gamma 1 fusion (hIL-20RA/Ch1 IgG) was correct. The hIL-20RA/Ch1 IgG gamma 1 #1825 Zem229R vector was called vector #195. The IL-20RA/Ch1 IgGγ1 sequence thus obtained is depicted by SEQ ID NOs: 52 and 53. N-terminal sequencing indicated the presence of the predicted mature polypeptide sequence of SEQ ID NO: 54.

A separate construct having IL-20RB fused to K light was also constructed. The IL-20RB/human K light chain construction was performed as above by PCRing from DR1/7N-4 with oligos SEQ ID NO: 50 and SEQ ID NO: 51, digesting the resulting band with EcoRI and KpnI and then ligating this product into a previously EcoRI and KpnI digested and band-purified Vec#77 (above). The resulting vector was sequenced to confirm that the IL-20RB/human κ light chain fusion (IL-20RB/Klight) was correct. This IL-20RB//κlight construct is shown by SEQ ID NOs: 56 and 57. N-terminal sequencing of the resultant polypeptide indicated the presence of the predicted mature amino acid sequence comprised of SEQ ID NO: 58. SEQ ID NO:59 is the mature portion of the extracellular domain of IL-20RB used.

Co-Expression of the Human IL-20RA and Human IL-20RB Receptors

Approximately 16 μg of each of vectors #194 and #195, above, were co-transfected into BHK-570 cells (ATCC No. CRL-10314) using Lipofectamine™ reagent (Gibco/BRL), as per manufacturer's instructions. The transfected cells were selected for 10 days in DMEM+5% FBS (Gibco/BRL) containing 1 μM of methotrexate (MTX) (Sigma, St. Louis, Mo.) and 0.5 mg/ml G418 (Gibco/BRL) for 10 days. The resulting pool of transfectants was selected again in 10 μM MTX and 0.5 mg/ml G418 for 10 days.

The resulting pool of doubly selected cells was used to generate protein. Three factories (Nunc, Denmark) of this pool were used to generate 8 L of serum free conditioned medium. This conditioned media was passed over a 1 ml protein-A column and eluted in (10) 750 microliter fractions. 4 of these fractions found to have the highest concentration were pooled and dialyzed (10 kD MW cutoff) against PBS. Finally, the dialyzed material was analyzed by BCA (Pierce) and found to have a concentration of 317 μg/ml. A total of 951 μg was obtained from this 8 L purification.

EXAMPLE 13

IL-20 Binding Activates STAT3 in the HaCaT Keratinocyte Cell Line

IL-20 binds cell lines transfected with both subunits of its receptor. However, these cell lines overexpress the IL-20 receptor relative to its normal level and their relevance to the physiological role of IL-20 is unclear. The human HaCaT keratinocyte cell line, which expresses endogenous IL-20RA and IL-20RB was used to examine IL-20 signal transduction in a biologically relevant cell type. HaCaT cells were infected with recombinant adenovirus containing a reporter construct to allow detection of intracellular signaling. The construct consists of the firefly luciferase gene driven by promoter/enhancer sequences comprised of the serum response element (SRE) and signal transducers and activators of transduction elements (STATs). This assay system detects productive ligand-receptor interactions and indicates possible downstream signal transduction components involved in receptor activation. Treatment with IL-20 alone resulted in a dose-dependent increase in luciferase activity with a half maximal response occurring at approximately 2.3 nM. Subsequent luciferase reporter assays using adenovirus vectors containing only the SRE element or only the STAT elements produced detectable reporter activation only through STATs.

To determine if other cytokines act in concert with IL-20, HaCaT cells were treated with IL-20 alone or in combination with a single submaximal dose of EGF, IL-1β, or TNFα. In the presence of each of these three proteins, IL-20 treatment resulted in a dose-dependent increase in luciferase activity. IL-20 in combination with IL-1β results in a half-maximal response at approximately 0.5 nM, about five-fold lower than with IL-20 alone. In addition, activation of the reporter gene is detectable at 0.1 nM IL-20, a dose that is at least tenfold lower than the IL-20 dose required alone.

BHK cells transfected with IL-20RA, IL-20RB or both receptor subunits were used to determine whether receptor pairing was required for IL-20 stimulation of STAT-luciferase. As was the case with binding assays, only cells transfected with both receptor subunits responded to IL-20 and did so with a half-maximal response of 5.7 pM. We note that the IL-20 concentration for the half-maximal response in BHK cells is 400-fold lower than that for half-maximal response in HaCaT cells. It is likely that a lower concentration of IL-20 is needed for half-maximal response in BHK cells, as compared to HaCaT cells, due to higher receptor levels in the BHK IL-20 receptor transfectants.

A nuclear translocation assay was used to identify STAT proteins involved in IL-20 action. Both HaCaT cells, with endogenous IL-20 receptors, and BHK cells transfected with IL-20RA and IL-20RB, were treated with IL-20 protein and translocation of STAT3 and STAT1 transcription factors from the cytoplasm to the nucleus was assayed by immunofluorescence.

In unstimulated HaCaT cells, STAT3 staining was predominantly in the cytosol. Treatment of HaCaT cells with IL-20 resulted in a distinct accumulation of STAT3 in the nucleus. Nuclear translocation of STAT3 in response to increasing concentrations of IL-20 occurred with a half-maximal IL-20 concentration of 7 nM. In contrast to STAT3 translocation, HaCaT cells treated with IL-20 did not show any detectable nuclear accumulation of STAT1.

BHK cells transfected with IL-20RA and IL-20RB were used to confirm that the IL-20 receptor was required for IL-20 stimulation of STAT3 nuclear translocation. In BHK cells lacking the IL-20 receptor, STAT3 remained cytosolic following treatment with IL-20. In contrast, in BHK cells transfected with the IL-20 receptor, STAT3 translocated to the nucleus in response to IL-20. Again, STAT1 remained cytosolic regardless of IL-20 treatment or IL-20 receptor expression. We conclude that the IL-20 receptor is required for IL-20-mediated STAT3 activation.

What is claimed is:

1. An isolated soluble receptor comprising an IL-20RA subunit and an IL-20RB subunit, wherein the IL-20RA subunit comprises the polypeptide of SEQ ID NO: 12, and the IL-20RB subunit comprises the polypeptide of SEQ ID NO: 15.

2. The soluble receptor of claim 1 wherein the IL-20RA subunit and the IL-20RB subunit are linked together by a polypeptide linker.

3. The soluble receptor of claim 2 wherein the polypeptide linker has about 100 to 240 amino acid residues.

4. The soluble receptor of claim 3 wherein the polypeptide linker has about 170 amino acid residues.

5. The soluble receptor of claim 1 wherein the IL-20RA subunit further comprises a polypeptide linker having at least one cysteine residue and the IL-20RB subunit further comprises a polypeptide linker having at least one cysteine residue, wherein at least one disulfide bond forms with a cysteine residue from the polypeptide linker of the IL-20RA subunit and with a cysteine residue from the polypeptide linker of the IL-20RB subunit.

6. The soluble receptor of claim 5 wherein the IL-20RA subunit is fUsed to all or a portion of the constant region of a heavy chain of an immunoglobulin (Ig) molecule, and the IL-20RB subunit is fused to all or a portion of the constant region of a light chain of an immunoglobulin molecule, wherein the light chain and the heavy chain are connected by a disulfide bond.

7. The soluble receptor of claim 6 wherein the constant region of the heavy chain comprises a CH1 domain, a CH2 domain and a hinge sequence that connects the CH1 domain with the CH2 domain.

* * * * *